US009603877B2

(12) United States Patent
Chang et al.

(10) Patent No.: US 9,603,877 B2
(45) Date of Patent: *Mar. 28, 2017

(54) ISOLATED NUCLEOTIDE MOLECULE AND METHOD OF SENSING AND KILLING OF PATHOGENIC MICROORGANISM

(71) Applicant: Nanyang Technological University, Singapore (SG)

(72) Inventors: Matthew Wook Chang, Singapore (SG); In Young Hwang, Singapore (SG); Mui Hua Tan, Singapore (SG); Elvin Koh, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 14/644,698

(22) Filed: Mar. 11, 2015

(65) Prior Publication Data
US 2015/0209393 A1  Jul. 30, 2015

Related U.S. Application Data

(63) Continuation-in-part of application No. 13/586,657, filed on Aug. 15, 2012, now Pat. No. 9,044,020.

(60) Provisional application No. 61/529,417, filed on Aug. 31, 2011.

(51) Int. Cl.
| | |
|---|---|
| A61K 35/74 | (2015.01) |
| C12N 15/70 | (2006.01) |
| A01N 37/46 | (2006.01) |
| A01N 63/02 | (2006.01) |
| A61K 38/16 | (2006.01) |
| A01N 43/08 | (2006.01) |
| A61K 35/00 | (2006.01) |

(52) U.S. Cl.
CPC .............. *A61K 35/74* (2013.01); *A01N 37/46* (2013.01); *A01N 43/08* (2013.01); *A01N 63/02* (2013.01); *A61K 38/164* (2013.01); *C12N 15/70* (2013.01); *A61K 2035/11* (2013.01)

(58) Field of Classification Search
None
See application file for complete search history.

(56) References Cited

U.S. PATENT DOCUMENTS

2012/0027786 A1* 2/2012 Gupta ................ C07K 14/21
424/184.1

OTHER PUBLICATIONS

Saeidi et al., Molecular Systems Biology 2011, EPub date Aug. 16, 2011, 7:521-531.*

Zhang et al., Nature Biotech. p. 24(1)100-104.*
Anderson et al., "Environmentally Controlled Invasion of Cancer Cells by Engineered Bacteria," *J Mol Biol* 355:619-627, 2006.
Asad et al., "Bench-to-bedside review: Quorum sensing and the role of cell-to-cell communication during invasive bacterial infection," *Crit Care* 12:236, 2008, 11 pages.
Baba et al., "Instruments of microbial warfare: bacteriocin synthesis, toxicity and immunity," *Trends Microbiol* 6(2):66-71, Feb. 1998.
Bradford, "A Rapid and Sensitive Method for the Quantitation of Microgram Quantities of Protein Utilizing the Principle of Protein-Dye Binding." *Anal Biochem* 72:248-254, 1976.
Canton et al., "Refinement and standardization of synthetic biological parts and devices," *Nat Biotechnol* 26(7):787-793, 2008.
Chak et al., "Cloning and characterization of the ColE7 plasmid," *J Gen Microbiol* 137:91-100, 1991.
Chang et al., "Microarray analysis of *Pseudomonas aeruginosa* reveals induction of pyocin genes in response to hydrogen peroxide," *BMC Genomics* 6:115, 2005, 14 pages.
Chang et al., "Microarray Analysis of Toxicogenomic Effects of Peracetic Acid on *Pseudomonas aeruginosa*," *Environ Sci Technol* 39(15):5893-5899, 2005.
Charlson et al., "Disordered Microbial Communities in the Upper Respiratory Tract of Cigarette Smokers," *PLoS ONE* 5(12):e15216, Dec. 2010, 10 pages.
Charlton et al., "A novel and sensitive method for the quantification of *N*-3-oxoacyl homoserine lactones using gas chromatography-mass spectrometry: application to a model bacterial biofilm," *Environ Microbiol* 2(5):530-541, 2000.
Chen et al., "Adsorptive refolding of a highly disulfide-bonded inclusion body protein using anion-exchange chromatography," *J Chromatogr A* 1216:4877-4886, 2009.

(Continued)

*Primary Examiner* — Doug Schultz
(74) *Attorney, Agent, or Firm* — Seed IP Law Group LLP

(57) ABSTRACT

The present invention relates to an isolated nucleic acid molecule comprising (a) a first nucleotide sequence encoding a protein that detects the presence, amount or both of a pathogenic microorganism by forming a complex with a quorum sensing molecule produced by said pathogenic microorganism, (b) one or more second nucleotide sequence said one or more second nucleotide sequence being under control of a promoter that is induced by the complex of the protein encoded by the first nucleotide sequence and the quorum sensing molecule produced by said pathogenic microorganism and encoding (i) an antimicrobial peptide, wherein the antimicrobial peptide is effective against the pathogenic microorganism detected by the protein encoded by the first nucleotide sequence; and/or an antibiofilm enzyme wherein the antibiofilm enzyme is effective against the pathogenic microorganism detected by the protein encoded by the first nucleotide sequence; and (c) optionally a third nucleotide sequence encoding a protein that controls the motility of the host organism, wherein the protein that controls the motility of the host organism directs the motility of the host organism towards said pathogenic microorganism. A recombinant microorganism comprising the isolated nucleic acid molecule and a method of sensing and killing pathogenic microorganisms is also described.

24 Claims, 32 Drawing Sheets

(56) References Cited

OTHER PUBLICATIONS

Choi et al., "A 10-min method for preparation of highly electrocompetent *Pseudomonas aeruginosa* cells: application for DNA fragment transfer between chromosomes and plasmid transformation," *J Microbiol Methods* 64:391-397, 2006.

Choudhary et al., "Applications of quorum sensing in biotechnology," *Appl Microbiol Biotechnol*. 86:1267-1279, 2010.

Endy, "Foundations for engineering biology," *Nature* 438:449-453, Nov. 24, 2005.

Gray et al., "Interchangeability and Specificity of Components from the Quorum-Sensing Regulatory Systems of *Vibrio fischeri* and *Pseudomonas aeruginosa*," *J Bacteriol* 176(10):3076-3080, May 1994.

Huang et al., "Soluble fusion expression and characterization of bioactive human beta-defensin 26 and 27," *Appl Microbiol Biotechnol* 84: 301-308, 2009.

Lin et al., "Induction of membrane permeability in *Escherichia coli* mediated by lysis protein of the ColE7 operon," *FEMS Microbiol Lett* 298:85-92, 2009.

Ling et al., "A predicted S-type pyocin shows a bactericidal activity against clinical *Pseudomonas aeruginosa* isolates through membrane damage," *FEBS Lett* 584:3354-3358, 2010.

Pearson et al., "A second N-acylhomoserine lactone signal produced by *Pseudomonas aeruginosa*," *Proc Natl Acad Sci USA* 92:1490-1494, Feb. 1995.

Ro et al., "Production of the antimalarial drug precursor artemisinic acid in engineered yeast," *Nature* 440:940-943, Apr. 13, 2006.

Scholl et al., "Antibacterial Efficacy of R-Type Pyocins towards *Pseudomonas aeruginosa* in a Murine Peritonitis Model," *Antimicrob Agents Chemother* 52(5):1647-1652, May 2008.

Schuster et al., "Promoter specificity in *Pseudomonas aeruginosa* quorum sensing revealed by DNA binding of purified LasR," *Proc Natl Acad Sci USA* 101(45): 15833-15839, Nov. 9, 2004.

Seo et al., "Purification of the pyocin S2 complex from *Pseudomonas aeruginosa* PAO1: analysis of DNase activity," *Biochem Biophys Res Commun* 172(2):455-461, 1990.

Sinha et al., "Reprogramming bacteria to seek and destroy an herbicide," *Nat Chem Biol* 6:464- 470, Jun. 2010.

Small et al., "Comparative global transcription analysis of sodium hypochlorite, peracetic acid, and hydrogen peroxide on *Pseudomonas aeruginosa*," *Appl Microbiol Biotechnol* 76:1093-1105, 2007.

Smith et al., "The pyocin Sa Receptor of *Pseudomonas aeruginosa* Is Associated with Ferripyoverdin Uptake," *J Bacteriol* 174(14):4847-4849, Jul. 1992.

Smith et al., "Signal Discrimination by Differential Regulation of Protein Stability in Quorum Sensing," *J Mol Biol* 382:1290-1297, 2008.

Steen et al., "Microbial production of fatty-acid-derived fuels and chemicals from plant biomass," *Nature* 463:559-563, Jan. 2010.

Wright et al., "A controlled clinical trial of a therapeutic bacteriophage preparation in chronic otitis due to antibiotic-resistant *Pseudomonas aeruginosa*; a preliminary report of efficacy," *Clin Otolaryngol* 34:349-357, 2009.

\* cited by examiner

Sensing with S5 and E7
(ptetR-LasR-pluxR-ss-pluxR-E7)

| Part Abbreviation | Description | Symbol |
|---|---|---|
| pTetR | tetR constitutive promoter | pTetR |
| pLuxR | luxR quorum sensing promoter | pLuxR |
| rbs3 | Ribosome binding site (medium) | rbs3 |
| rbs5 | Ribosome binding site (strong) | rbs5 |
| T15 | Double terminator | T15 |
| LasR | LasR coding gene | LasR |
| GFP | GFP coding gene | GFP |
| E7 | E7 lysis coding gene | E7 |
| S5 | Pyocin S5 coding gene | S5 |
| pTetR-LasR-pLuxR | Sensing device | pTetR rbs5 LasR T15 pLuxR |
| pTetR-LasR-pLuxR-GFP | Sensing device with GFP reporter | pTetR rbs5 LasR T15 pLuxR rbs3 GFP T15 |
| pTetR-LasR-pLuxR-S5 | Sensing device with pyocin S5 gene | pTetR rbs5 LasR T15 pLuxR rbs5 S5 T15 |
| pTetR-LasR-pLuxR-E7 | Sensing device with E7 lysis gene | pTetR rbs5 LasR T15 pLuxR rbs3 E7 T15 |
| pTetR-LasR-pLuxR-S5-pLux-E7 | Sensing/Killing system construct | pTetR rbs5 LasR T15 pLuxR rbs5 S5 T15 / pLuxR rbs3 E7 T15 |

*FIG 7E*

ISOLATED NUCLEOTIDE MOLECULE AND METHOD OF SENSING AND KILLING OF PATHOGENIC MICROORGANISM

CROSS-REFERENCE TO RELATED APPLICATION

This application is a continuation-in-part application of U.S. application Ser. No. 13/586,657 entitled "An Isolated Nucleotide Molecule And Method Of Sensing And Killing Of Pathogenic Microorganism" filed on Aug. 15, 2012; which claims the benefit of U.S. provisional patent application No. 61/529,417, filed Aug. 31, 2011, the contents of it being hereby incorporated by reference in its entirety for all purposes.

TECHNICAL FIELD

Various embodiments relate to the field of an engineered microbe that can sense and eradicate a pathogenic microorganism, in particular, *Pseudomonas aeruginosa*.

BACKGROUND

Synthetic biology aims to engineer genetically modified biological systems that perform novel functions that do not exist in nature, with reusable, standard interchangeable biological parts. The use of these standard biological parts enables the exploitation of common engineering principles such as standardization, decoupling, and abstraction for synthetic biology. With this engineering framework in place, synthetic biology has the potential to make the construction of novel biological systems a predictable, reliable, systematic process. While the development of most synthetic biological systems remains largely ad hoc, recent efforts to implement an engineering framework in synthetic biology have provided long-awaited evidences that engineering principles can facilitate the construction of novel biological systems. Synthetic biology has demonstrated that its framework can be applied to a wide range of areas such as energy, environment, and health care. For example, biological systems have been constructed to produce drugs and biofuels, to degrade contaminants in water, and to kill cancer cells.

Despite these advances, synthetic biology has not yet been exploited to develop new strategies for tackling infectious disease, a leading cause of death worldwide, especially in poor countries. Given the stalled development of new antibiotics and the increasing emergence of multidrug-resistant pathogens, using synthetic biology to design new treatment regimens for infectious disease could address an urgent need.

*Pseudomonas aeruginosa* (or often referred to as *P. aeruginosa*) colonizes the respiratory and gastrointestinal tract, and causes life-threatening infections to patients with immunodeficiency such as cystic fibrosis and cancer. Despite a wide range of antibiotics available in the market, *P. aeruginosa* is still among the leading causes of nosocomial infection primarily because it is intrinsically resistant to many antibiotics and antimicrobials, in part because of its effective efflux systems. Contemporary treatments against *P. aeruginosa* infection include antibiotic chemotherapy and bacteriophage therapy. In antibiotic chemotherapy, a combinatorial treatment involving multiple antimicrobial agents is usually preferred over monotherapy due to the rapid acquisition of drug tolerance in *P. aeruginosa*. This approach, however, promotes unspecific killing of bacteria and upsets a healthy human microbiome. Phage therapy involves strain-specific bacteriophages that invade and destroy the cellular integrity of pathogens. The therapeutic potential of employing virus in bacterial infection, however, is limited, as a directed treatment cannot be re-employed after the infected host develops specific antibodies against the introduced virus.

Thus, there is need in the art for novel, unconventional antimicrobial strategies that do not entirely rely on current antibiotics that address the problems mentioned above, especially in combating *P. aeruginosa* infections.

SUMMARY OF THE INVENTION

In a first aspect of the present invention, an isolated nucleic acid molecule is provided. The isolated nucleic acid molecule comprises (a) a first nucleotide sequence encoding a protein that detects the presence, amount or both of a pathogenic microorganism by forming a complex with a quorum sensing molecule produced by said pathogenic microorganism, (b) one or more second nucleotide sequence said one or more second nucleotide sequence being under control of a promoter that is induced by the complex of the protein encoded by the first nucleotide sequence and the quorum sensing molecule produced by said pathogenic microorganism and encoding (i) an antimicrobial peptide, wherein the antimicrobial peptide is effective against the pathogenic microorganism detected by the protein encoded by the first nucleotide sequence; and/or (ii) an antibiofilm enzyme, wherein the antibiofilm enzyme is effective against the pathogenic microorganism detected by the protein encoded by the first nucleotide sequence; and (c) optionally a third nucleotide sequence encoding a protein that controls the motility of the host organism, wherein the protein that controls the motility of the host organism directs the motility of the host organism towards said pathogenic microorganism.

In a second aspect, a recombinant microorganism is provided. The recombinant microorganism comprises the isolated nucleic acid molecule comprising (a) a first nucleotide sequence encoding a protein that detects the presence, amount or both of a pathogenic microorganism by forming a complex with a quorum sensing molecule produced by said pathogenic microorganism, (b) one or more second nucleotide sequence said one or more second nucleotide sequence being under control of a promoter that is induced by the complex of the protein encoded by the first nucleotide sequence and the quorum sensing molecule produced by said pathogenic microorganism and encoding (i) an antimicrobial peptide, wherein the antimicrobial peptide is effective against the pathogenic microorganism detected by the protein encoded by the first nucleotide sequence; and/or (ii) an antibiofilm enzyme, wherein the antibiofilm enzyme is effective against the pathogenic microorganism detected by the protein encoded by the first nucleotide sequence; and (c) optionally a third nucleotide sequence encoding a protein that controls the motility of the host organism, wherein the protein that controls the motility of the host organism directs the motility of the host organism towards said pathogenic microorganism.

In one embodiment, the isolated nucleic acid is comprised in a vector.

In a further aspect, the present invention relates to a method of sensing and killing pathogenic microorganisms. The method comprises contacting a recombinant microorganism with the pathogenic microorganism. The recombinant microorganism comprises an isolated nucleic acid molecule including (a) a first nucleotide sequence encoding a protein that detects the presence, amount or both of a pathogenic microorganism by forming a complex with a quorum sensing molecule produced by said pathogenic microorganism, (b) one or more second nucleotide sequence said one or more second nucleotide sequence being under control of a promoter that is induced by the complex of the protein encoded by the first nucleotide sequence and the quorum sensing molecule produced by said pathogenic microorganism and encoding (i) an antimicrobial peptide, wherein the antimicrobial peptide is effective against the pathogenic microorganism detected by the protein encoded by the first nucleotide sequence; and/or (ii) an antibiofilm enzyme, wherein the antibiofilm enzyme is effective against the pathogenic microorganism detected by the protein encoded by the first nucleotide sequence; and (c) optionally a third nucleotide sequence encoding a protein that controls the motility of the host organism, wherein the protein that controls the motility of the host organism directs the motility of the host organism towards said pathogenic microorganism.

BRIEF DESCRIPTION OF THE DRAWINGS

The invention will be better understood with reference to the detailed description when considered in conjunction with non-limiting examples and the accompanying drawings, in which:

In FIG. 1B the production of pyocin S5 and lysis E7 proteins within the *Escherichia coli* chassis occurs after induction. Upon reaching a threshold concentration, the lysis E7 protein perforates membrane of the *E. coli* host and releases the accumulated pyocin S5. Pyocin S5, which is a soluble protein, then diffuses toward the target pathogen and damages its cellular integrity, thereby killing it.

FIG. 2A shows GFP production rate per cell over time at different $3OC_{12}HSL$ inducer concentrations. FIG. 2B shows time-averaged GFP production rate per cell at different input $3OC_{12}HSL$ concentrations, showing that the optimal operating concentrations for the sensing device range from 1.0E-7 to 1.0E-6M $3OC_{12}HSL$. Error bar represents the standard deviation of statistical means between 20 and 80 mins after induction, performed with six replicates.

FIG. 3A shows the growth curve of *E. coli* expressing E7 lysis protein after induction with different concentrations of $3OC_{12}HSL$. FIG. 3B and FIG. 3C show the effects of lysis protein on *E. coli* surface morphology as observed using a Field Emission Scanning Electron Microscope (FESEM). It was observed that the surface of the *E. coli* was damaged when *E. coli* carrying pTetR-LasR-pLuxR-E7 and *E. coli* carrying pTetR-LasR-pLuxR-S5-pLuxR-E7 (the final system) were induced with $3OC_{12}HSL$. Scale bar: 1 mm. Error bar represents the standard deviation of four replicates.

FIG. 4A shows sodium dodecyl sulfate polyacrylamide gel electrophoresis (SDS-PAGE) of (i, ii) total extracellular proteins and (iii-viii) IMAC purified His-tagged S5 protein sampled from the extracellular supernatant. Total extracellular proteins exported from (i) *E. coli* carrying pTetR-LasR-pLuxR-S5 (without lysis device) was significantly lesser than that exported from (ii) *E. coli* carrying pTetR-LasR-pLuxR-S5-pLuxR-E7 (the final system) as indicated in darker lanes of (ii) relative to (i). (iii-v): *E. coli* carrying pTetR-LasR-pLuxR-S5 (without lysis device) at 0, 2, and 4 hrs after induction. (vi-viii) *E. coli* carrying pTetR-LasR-pLuxR-S5-pLuxR-E7 (the final system) at 0, 2, and 4 hrs after induction. It can be seen that pyocin S5 (57 kDa; arrowed) was only detectable in lanes that corresponded to *E. coli* carrying the final system and not in lanes of *E. coli* without the lysis device. Ladder used was Bio-Rad's Precision Plus Protein standards. FIG. 4B shows the characterization of lysis device in the final system by optical density (bar graphs) and concentration of pyocin released (lines) after induction. An impulse release of pyocin S5 was observed at 2 hrs after induction, followed by a sustained steady-state release in the final system (dotted lines). Optical density of the final system was characterized by an initial decrease at 2 hrs after induction, indicative of the onset of lysis, after which the regrowth of engineered *E. coli* occurs (shaded bar). Correspondingly, the concentration of pyocin released in *E. coli* without the lysis device (solid line) was ⅛ that of the final system with a continually increasing optical density (unshaded bar). Error bar represents the standard deviation of two replicates.

FIG. 5A shows agar overlay assay of *P. aeruginosa* after exposure to supernatant of four different cultures. First, *P. aeruginosa* exposed to supernatant of wild-type *E. coli* showed no bactericidal activity. Second, *P. aeruginosa* exposed to supernatant of wild-type *E. coli* mixed with *P. aeruginosa* produced no inhibition zones. Third, exposure to supernatant of *E. coli* carrying pTetR-LasR-pLuxRS5-pLuxR-E7 (final system) did not produce any inhibition as well. Fourth, only *P. aeruginosa* exposed to supernatant of *E. coli* carrying final system with *P. aeruginosa* displayed clear inhibition zones, which suggested that the system produced sufficient pyocin S5 to exhibit bactericidal activity. FIG. 5B shows *P. aeruginosa* cells stained using the LIVE/DEAD cell viability assay. Many *P. aeruginosa* cells were stained with PI dye, which indicate dead cells, when exposed to supernatant of engineered *E. coli* carrying the final system that was induced by native $3OC_{12}HSL$ produced by *P. aeruginosa*. FIG. 5C shows fluorescence measurement of *P. aeruginosa* that constitutively expresses GFP in mixed culture with engineered *E. coli*. Analysis of the mixed culture with the engineered *E. coli* carrying pTetR-LasR-pLuxR-E7 and pTet-LasRpLuxR-S5 shows an exponential increase in the fluorescence readings, whereas the mixed culture with *E. coli* carrying pTetR-LasR-pLuxR-S5-pLuxR-E7 (the final system) exhibited no increase in the readings. This may suggest that the growth of *P. aeruginosa* was significantly inhibited in the mixed culture with engineered *E. coli* carrying the final system. PAO1, which pyocin S5 was derived from, was included as a negative control. Error bar represents the standard deviation of six replicates. FIG. 5D shows the percentage survival of *P. aeruginosa* carrying chloramphenicol-resistant plasmid in mixed culture with the engineered *E. coli*. *Pseudomonas* in the mixed culture was quantified by viable cell count using chloramphenicol selection. It was observed that the engineered *E. coli* according to various embodiments inhibited the growth of *Pseudomonas* by 99%. In contrast, inhibition was less observed in *Pseudomonas* co-cultured with incomplete *E. coli* systems missing either the pyocin S5 killing device or E7 lysis device. Error bar represents the standard deviation of three replicates.

FIG. 6A shows the percentage survival of *P. aeruginosa* biofilm carrying chloramphenicol-resistant plasmid. *Pseudomonas* biofilm was grown in a polystyrene 24-well plate in the presence of the engineered *E. coli* for 18 hrs and quantified by viable cell count using chloramphenicol selection. The formation of *Pseudomonas* biofilm was inhibited by close to 90% with the engineered *E. coli* carrying the final system (pTetR-LasR-pLuxR-S5-pLuxRE7) as compared with biofilm grown with wild-type *E. coli* or incomplete *E. coli* system missing either pyocin S5 or E7 lysis genes. *P. aeruginosa* PAO1, which pyocin S5 was derived from, was included as a negative control. Error bar represents the standard deviation of six replicates. FIG. 6B shows biofilm inhibition observed under CLSM (confocal laser scanning microscopy). *Pseudomonas* biofilm with green fluorescence was grown on glass slide in the presence of the engineered *E. coli* and visualized under CLSM microscope after 18 hrs. Images reconstructed from biofilm Z-stacks using Zeiss 2.5D software implied that the initialization and progression of biofilm cells into multilayers were strongly inhibited for *Pseudomonas* grown with *E. coli* carrying the final system as opposed to lush and elaborated biofilm formation observed in *Pseudomonas* grown alone or with incomplete *E. coli* system missing either pyocin S5 or E7 lysis genes. Scale bar: 50 mm. Z-stack: 40 mm.

FIGS. 7A-7E show the plasmid map of the engineered system/devices in pSB1A2 vector. FIG. 7A shows the final engineered system, pTetR-LasR-pLuxR-S5-pLuxR-E7. The system recognizes input chemical signals from *P. aeruginosa* and produces S5 pyocin and E7 lysis proteins. FIG. 7B shows a sensing device coupled to GFP, pTetR-LasR-pLuxR-GFP. This construct was used as a measurement tool for characterization of the sensor (pTetR-LasR-pLuxR). FIG. 7C shows a sensing device with E7 lysis, pTetR-LasR-pLuxR-E7. This construct was used for the characterization of E7 lysis protein whose function is to disrupt cell membrane for the release of pyocin. FIG. 7D shows a sensing device with pyocin S5, pTetR-LasR-pLuxR-S5. This construct was used as a control to compare the efficiency of lysis device in mediating protein release. FIG. 7E summarizes plasmids, Biobrick parts, and devices used in some examples.

FIG. 8A shows agar overlay assay of *P. aeruginosa* after exposure to supernatant of the *E. coli* carrying pTetR-LasR-pLuxR-S5-pLuxR-E7 (the final system) at different $3OC_{12}HSL$ concentrations. Faint inhibition areas were observed with 0M and 1.0E-8M $3OC_{12}HSL$. It is shown that supernatant of engineered *E. coli* culture induced by 1.0E-6M $3OC_{12}HSL$ produced wider and clearer inhibition zones relative to other inducer concentrations. FIG. 8B shows *P. aeruginosa* cells stained using the LIVE/DEAD cell viability assay. It is shows that more PI-stained *P. aeruginosa* cells were present when *P. aeruginosa* was exposed to supernatant of the *E. coli* carrying the final system that was induced by $3OC_{12}HSL$, whereas all *P. aeruginosa* cells exposed to supernatant of wild-type *E. coli* (control) were stained with SYTO 9 (green). Scale bar: 5 µm. FIG. 8C shows CFU count of *P. aeruginosa* (carrying chloramphenicol-resistant plasmid pAWG1-1) in a mixed culture with engineered *E. coli*. To study whether the engineered *E. coli* carrying the final system can inhibit growth of *P. aeruginosa* in mixed culture, clinical isolate ln 7 and pyocin resistant control strain PAO1 was co-cultured with engineered *E. coli* in the ratio 1:4 and quantified by viable cell count of *Pseudomonas*. Additionally, ln 7 was also co-cultured with control *E. coli* missing either the pyocin S5 or E7 lysis devices. It is shown that only the final system (i.e. pTetR-LasR-pLuxR-S5-pLuxR-E7), complete with sensing, killing and lysis devices are capable of inhibiting the growth of *P. aeruginosa* for 15 hours. Error bar represents the standard deviation of 3 independent replicates.

DETAILED DESCRIPTION OF THE INVENTION

Figure 1A:
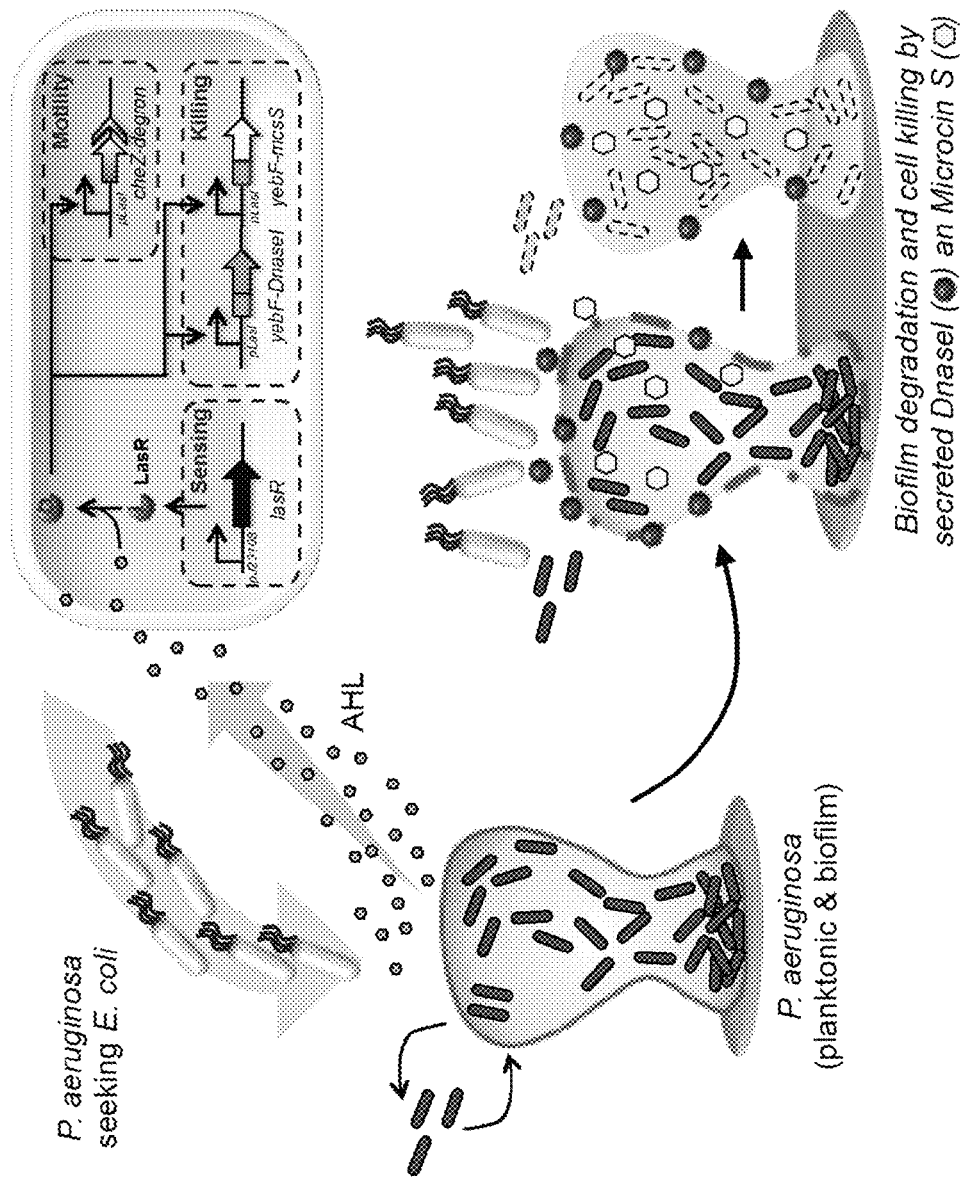
FIGS. 1A and 1B show a schematic overview of 'Pathogen Sensing and Killing' system, according to various embodiments. The 'Seek and kill' system (FIG. 1A) and the 'sense and kill' system (FIG. 1B) in *E. coli* The sensing device was designed based on the Type I quorum sensing mechanism of *P. aeruginosa*. The tetR promoter ($P_{tetR}$), which is constitutively on, produces a transcriptional factor, LasR, that binds to AHL $3OC_{12}HSL$. The luxR promoter ($P_{luxR}$), to which LasR-$3OC_{12}HSL$ activator complex reportedly binds, was adopted as the inducible promoter in the sensing device. Next, the formation of the LasR-$3OC_{12}HSL$ complex, which binds to the luxR promoter, activates the seeking and killing or the killing and lysing devices.

The following detailed description refers to the accompanying drawings that show, by way of illustration, specific details and embodiments in which the invention may be practiced. These embodiments are described in sufficient detail to enable those skilled in the art to practise the invention.

Various embodiments provide a novel antimicrobial strategy based on an engineered microbial system using the synthetic biology framework.

Various embodiments may provide a genetic system that was designed and constructed based on standardization, decoupling, and abstraction that allows sensing and killing of *P. aeruginosa*, a human pathogen, in a non-pathogenic chassis, *E. coli*.

Various embodiments may also provide an engineering microbe to sense and eradicate *P. aeruginosa*, a human pathogen.

The biological parts of the devices may be designed and synthesized in compliance with the BioBrick assembly standards. Each of the biological devices may be characterized to understand its behaviour, and the correlation between the input and output of the biological device may be studied in detail.

In a first aspect, an isolated nucleic acid molecule is provided. The isolated nucleic acid molecule comprises (a) a first nucleotide sequence encoding a protein that detects the presence, amount or both of a pathogenic microorganism by forming a complex with a quorum sensing molecule produced by said pathogenic microorganism, (b) one or more second nucleotide sequence said one or more second nucleotide sequence being under control of a promoter that is induced by the complex of the protein encoded by the first nucleotide sequence and the quorum sensing molecule produced by said pathogenic microorganism and encoding (i) an antimicrobial peptide, wherein the antimicrobial peptide is effective against the pathogenic microorganism detected by the protein encoded by the first nucleotide sequence; and/or an antibiofilm enzyme wherein the antibiofilm enzyme is effective against the pathogenic microorganism detected by the protein encoded by the first nucleotide sequence; and (c) optionally a third nucleotide sequence encoding a protein that controls the motility of the host organism, wherein the protein that controls the motility of the host organism directs the motility of the host organism towards said pathogenic microorganism As used herein in connection with a nucleic acid molecule, the term "isolated" refers to a nucleic acid molecule that is substantially free of other cellular material or components or culture medium, in particular when produced by recombinant techniques, or substantially free of chemical precursors and/or other chemical agents when chemically synthesized.

The term "nucleic acid molecule", as used herein, includes all forms of nucleic acids and includes DNA and RNA, in particular DNA, and may be single or double-stranded. Besides the nucleotide sequence encoding the protein for detection of the pathogenic microorganism, the nucleic acid molecule may comprise non-coding regions, such as sequences that control its expression, including, but not limited to promoters, enhancers, transcription factor binding sites, restriction enzyme binding sites, methylation sites, and the like.

The term "peptide" generally refers to polymers of amino acids and includes dipeptides, oligopeptides and polypeptides. In various embodiments of the invention, the antimicrobial peptides consist of 10 to 100 amino acids. In this context, "antimicrobial" means that the peptide inhibits the growth of or kills microorganisms, as defined below.

The term "pathogenic microorganism" includes bacteria, viruses, protozoa and fungi that can cause diseases or disorders in other, preferably eukaryotic, organisms, such as mammals, including humans.

For example, the pathogenic microorganism may be *P. aeruginosa*. In other examples, pathogenic microorganism may include but is not limited to *Clostridium difficile*, *E. coli*, *Helicobacter pylori*, *Salmonella* spec., *Vibrio cholera* and *Yersinia* spec.

The term "promoter" relates to transcriptional regulatory sequences that promote expression of a gene. Generally, numerous promoters as well as their use in recombinant systems are known to those skilled in the art. A promoter is usually but not necessarily, positioned upstream, or 5', of a structural gene to be expressed.

The term "complex", as used herein, relates to a complex of a signal triggering molecule (a ligand) with a biomolecule such as a proteins that are, usually non-covalently bound to each other. The binding between the molecules is usually by reversible intermolecular forces such as ionic bonds, hydrogen bonds and Van de Waals forces. The complex may be a specific complex, i.e. the molecules of the complex specifically bind to each other, meaning that they preferentially bind to each other over other molecules that may be present in a cellular environment. The affinity of the complex molecules to each other should be high enough to allow complex formation. In various embodiments, the dissociation constant of the complex, $K_d$, is at least $10^{-6}$M. In this context, specific binding may mean that the complex partners bind to each other with an at least 10 fold, at least 100-fold, or at least 1000-fold higher affinity compared to other molecules. Formation of the complex alters the chemical conformation of the biomolecule such as the first protein, to a second conformation of the complex. In the second conformation the complex can bind to the second or the third promoter to induce expression of the second or third nucleic acid molecule. The first nucleotide sequence encoding the protein that detects the presence, amount or both of a pathogenic microorganism is able to do this by forming a complex with a quorum sensing molecule produced by a pathogenic microorganism. The first nucleotide sequence encodes a protein that forms a complex with a quorum sensing molecule produced by a pathogenic microorganism in the presence, amount or both of the pathogenic microorganism.

In one embodiment, the first nucleotide sequence may be under control of a constitutively active promoter. In various embodiments, the constitutive promoters which regulate the first nucleotide sequence may include any synthetic $\sigma^{70}$ or $\sigma^S$ promoters (e.g., synthetic $\sigma^{70}$ promoters with define −10 box TATAAT and −35 box TTGACA).

As used herein, by "constitutively active promoter" it is meant that a promoter that is continuously active, i.e. an operably linked nucleic acid sequence is continuously expressed, without being subject to regulation by external signals or inducer molecules. The term "promoter" is as defined above.

The term 'quorum sensing molecule' as used herein refers to various diffusible, chemical signals known as autoinducers that are produced by the synthase genes of the bacteria. The extracellular concentration of signaling molecules increases as a function of cell density and is permeable to cell membranes. Upon attaining a threshold concentration of the chemical signals, the quorum sensing cascade is activated to elicit expressions or repressions of multiple genes, including those that are functional for production of autoinducers such as acyl homoserine lactones (AHLs). This organic signaling cascade therefore regulates a number of physiological activities such as cell motility, virulence, biofilm formation and growth. Although similar production mechanisms are present in some Gram-negative bacteria, each synthase homolog producing AHLs differs in either length or functional groups (e.g., hydroxyl and carbonyl groups) on the acyl side chain. Thus, with each bacterium possessing disparate synthase sequence, a high level of specificity can be achieved during intercellular quorum communication.

In various embodiments, the quorum sensing molecule includes acyl homoserine lactones (AHL).

The term "acyl homoserine lactones (AHL)" refers to intracellular signal molecules produced by different microorganisms, including *P. aeruginosa*, and may be released outside of the bacterial cell, involved in quorum-sensing. For example, in the context of *P. aeruginosa*, the quorum-sensing molecule released may include AHL-dependent signalling molecules, such as N-butanoyl-1-homoserine lactone ($C_4$HSL) and N-3-oxododecanoyl homoserine lactone ($3OC_{12}$HSL) and/or AHL-independent quinolone-signalling molecule, e.g., 2-heptyl-3-hydroxy-4(1H)-quinolone.

In various embodiments, the protein encoded by the first nucleotide sequence may be a transcription factor.

In various embodiments, the transcription factor may be the protein LasR produced by the transcription and subsequent translation of the $P_{tetR}$ gene. Said LasR protein specifically interacts with microbial AHLs by forming a non-covalent complex therewith. Upon forming a complex with the AHL, e.g. those produced by *P. aeruginosa*, the complex then may bind to the transcription initiation site, i.e., the promoter, for example $P_{luxR}$ or $P_{lacI}$, controlling expression of the antimicrobial peptide, and/or the antibiofilm enzyme and optionally the lysis protein or the protein that controls the motility of the host organism. The genes encoding the antimicrobial peptide may be the pyocin or Microcin. The genes encoding the antibiofilm enzyme may be a nuclease such as a DNase. The genes encoding the protein that controls the motility of the host organism may be a the chemotaxis signal. The genes encoding the lysis protein may be lysis E7 genes.

In various embodiments, the protein encoded by the first nucleotide sequence may be the transcription factor LasR that binds to the AHL N-3-oxododecanoyl homoserine lactone ($3OC_{12}$HSL). In an example, another combination of quorum sensing system that may be applied to detect *P.*

*aeruginosa* may include the transcription factor RhlR that recognizes and binds the AHL N-butanoyl-1-homoserine lactone ($C_4HSL$).

In various embodiments, the first nucleotide sequence may have the nucleotide sequence set forth in SEQ ID NO: 1. For example, SEQ ID NO: 1 may be based on LasR gene (UniProt: PSPA7_3898).

In some examples, the first nucleotide sequence may include $P_{tetR}$-LasR (SEQ ID NO: 5). For example, the $P_{tetR}$ may be obtained from an *E. coli* plasmid cloning vector containing the p15A origin of replication (1-4) (GenBank: pACYC184).

In various embodiments, the inducible promoter of the second nucleotide sequence may be the luxR promoter that is bound and induced by a complex of LasR and $3OC_{12}HSL$. In various embodiments, the inducible promoter of the second nucleotide sequence may be the lasI promoter that is bound and induced by a complex of LasR and $3OC_{12}HSL$.

In the context of various embodiments, the term "inducible promoter" means a promoter that is not constitutively active, but rather is activated by external factors, such as binding partners, and thus able to regulate the amount and the timing of protein expression. The term "promoter" is as defined above. Besides the luxR promoter mentioned above, other inducible promoters that may be used to regulate the expression of the second nucleotide sequence include natural or synthetic luxR promoter analogues e.g., promoters of aprA, rhlI, rhlR, lasA, lasB, lasI and toxA. Herein, the phrase "synthetic promoter" refers to promoter variants generated by mutagenesis of the luxR promoter or its analogues, all of which are activated when bound to a complex of LasR and $3OC_{12}HSL$.

In various embodiments, the protein encoded by the second nucleotide sequence may be a bacteriocin.

The term "bacteriocin" refers to proteinaceous toxins produced by bacteria to inhibit the growth of similar or closely related bacterial strain(s). Various embodiments of the invention employ bacteriocins, ribosomally synthesized antimicrobial peptides. Bacteriocins are specific and effective against closely related species, and thus have garnered attention as a new generation antibacterial agent. For example, the bacteriocin may be a pyocin or the bacteriocin may be a microcin. Other examples of bacteriocins include colicin (e.g., against *E. coli*), lacticin 3147 (e.g., against *Clostridium difficile*) and vibriocin (e.g., against *Vibrio cholera*).

Microcins are ribosomally synthesized antimicrobial peptides with a low molecular mass. They are generally produced by enterobacteria, in particular *Escherichia coli*. Microcins exert potent antibacterial activity against both closely related species and more distant species of bacteria. There are 14 microcin peptides documented. Microcin S (MccS) was originally isolated from probiotic *E. coli* G3/10. Pyocins are narrow-spectrum bacteriocins produced by *P. aeruginosa*. Contrary to traditional antibiotics, the acquisition of pyocin resistance by lateral gene transfer between bacteria has not yet been encountered, supporting the use of pyocins in targeting *P. aeruginosa* infection. Pyocins are classified into three types: R, F, and S. R and F type pyocins may be synthesized by 90% of all *P. aeruginosa* strains and S type by 70%. More specifically, examples of pyocin may include S-type pyocins (e.g., S1, S2, S3, S4, AP41), R-type pyocins (e.g., R1, R2, R3) and F type pyocins (e.g., F1, F2, F3). The soluble S type pyocin, hereby named as Pyocin S5 (which may be interchangeably referred to "S5 pyocin") exhibits strong bactericidal activity against *P. aeruginosa* clinical isolates through membrane damage but is ineffective against *E. coli*.

In one embodiment, the pyocin may be pyocin S5.

In various embodiments the bacteriocin may be a microcin such as microcin S (MccS).

In various embodiments, the inducible promoter of the second nucleotide sequence may be the luxR promoter that may be bound and induced by a complex of LasR and $3OC_{12}HSL$. In various embodiments, the inducible promoter of the second nucleotide sequence may be the lasI promoter that is bound and induced by a complex of LasR and $3OC_{12}HSL$.

The second nucleotide sequence together with the inducible promoter may have the nucleotide sequence set forth in SEQ ID NO: 2. For example, SEQ ID NO: 2 may be $P_{luxR}$-pyocin S5. Alternatively, the second nucleotide sequence together with the inducible promoter may have the nucleotide sequence set forth in SEQ ID NO: 7. For example, SEQ ID NO: 7 may be or $P_{LasI}$-microcin S (modified from genbank accession No. AFH37358.1). The inducible promoter may be obtained from a *Vibrio fischeri* regulatory protein LuxR (luxR) gene (GenBank: AF170104.1) and the second nucleotide sequence may be pyocin S5 obtained from *P. aeruginosa* (strain ATCC 15692/PAO1/1C/PRS 101/LMG 12228) (UniProtKB/TrEMBL: Q9I4Y4_PSEAE).

In some embodiments the inducible promoter, pLasI, comprises of a truncated sequence found in the LasI-RsaL intergenic region. This region contains a las-rhl box-like element, which serves in the bidirectional LasR-3OC12HSL-dependent activation. The generated variant provides optimal expression level.

In various embodiments, the protein encoded by the first nucleotide sequence, the protein encoded by the second nucleotide sequence or both may be specific for a pathogenic microorganism.

In various embodiments the one or more second nucleotide sequence includes a antibiofilm enzyme. The antibiofilm enzyme may be a nuclease protein that is capable of degrading a biofilm produced by said pathogenic microorganism. In such an embodiment the antibiofilm enzyme is preferably a DNaseI enzyme. In this embodiment the one or more second nucleotide sequence together with the inducible promoter may have the nucleotide sequence set forth in SEQ ID NO: 8. For example, SEQ ID NO: 8 may be $P_{LasI}$-DNaseI. (modified from genbank accession No. NM_174534).

In various embodiments the antimicrobial peptide, the antibiofilm enzyme or both are fused to a secretion tag. As used herein 'secretion tag' refers to any expression system including a protein able to export a protein fused thereto into the growth medium of the host organism ("secretion") without affecting outer cell membrane integrity. The secretion tag may be linked to the N- or C-terminus of the one or more second nucleotide sequence. Preferably the secretion tag is linked to the N-terminus of the one or more second nucleotide sequence. The secretion tag may be an outer membrane protein F (OmpF), an osmotically inducible protein Y (OsmY) or a YebF protein. In various embodiments the secretion tag is YebF. The YebF secretion tag may have the nucleotide sequence set forth in SEQ ID NO: 10. (genbank accession No. NC_000913.3).

In various embodiments, the nucleic acid molecule may optionally comprise a third nucleotide sequence encoding a protein that controls the motility of the host organism. In such an embodiment the third nucleotide sequence encoding the protein that controls the motility of the host organism may be a Che chemotaxis signal, preferably CheZ. In this embodiment the third nucleotide sequence together with the inducible promoter may have the nucleotide sequence set forth in SEQ ID NO: 9. For example, SEQ ID NO: 9 may be $P_{LasI}$-CheZ. Alternatively CheA, or CheY may also work in controlling the motility of the host organism.

In various embodiments the amount of the protein that controls the motility of the host organism may be required to be maintained within a certain range. To achieve this expression level, the third nucleotide sequence may include a degron to decrease the stability of the protein that controls the motility of the host organism. As used herein 'degron' refers to a sequence encoding amino acids within a protein that directs the starting place of degradation of that protein. In various embodiments the degron is SsrA or YbaQ.

In various embodiments, the nucleic acid molecule may further comprise a third nucleotide sequence encoding a protein that may be capable of lysing a cell hosting the isolated nucleic acid molecule, wherein said third nucleotide sequence may be under control of a promoter that may be induced by the complex of the protein encoded by the first nucleotide sequence and the quorum sensing molecule produced by said pathogenic microorganism.

In the context of various embodiments, the term "lysing" refers to the perforation of the cell membrane and the subsequent release of the cytoplasmic components (i.e. components within the cell).

The protein encoded by the third nucleotide sequence may be a lysis protein that lyses the cell membrane of a cell hosting the nucleic acid molecule, for example an *E. coli* host cell.

The protein encoded by the third nucleotide sequence may be the E7 lysis protein. In other embodiments, *E. coli* host lysis may be mediated by any lytic systems utilizing phage holin and endolysin lysis proteins, or bacteriocin release proteins of cloacin DF13, colicin E1, E3, A and D.

In various embodiments, the third nucleotide sequence together with the inducible promoter may have the nucleotide sequence set forth in SEQ ID NO:3.

For example, SEQ ID NO:3 may be $P_{luxR}$-E7 lysis. The inducible promoter may be as defined above. The third nucleotide sequence may be E7 lysis obtained from Human papillomavirus type 16 (VE7 HPV16) (UniProtKB/Swiss-Prot: Q03709).

Various embodiments may provide a cellular system designed to (i) detect AHLs produced by *P. aeruginosa*; (ii) produce microcin S and/or DNaseI upon the detection; and (iii) move towards the *P. aeruginosa* so that the produced microcin S and/or DNaseI is released near the *P. aeruginosa*, leading to the killing of *P. aeruginosa*. The system may be comprised in a host cell, in particular an engineered *E. coli* cell, that may effectively seek and kill a *P. aeruginosa* producing AHL; thereby providing a novel synthetic biology-based antimicrobial strategy that may be applied to eradicate infectious pathogens.

Various embodiments may provide a system designed to (i) detect AHLs produced by *P. aeruginosa*; (ii) produce pyocin S5 upon the detection; and (iii) lyse the *E. coli* cells by E7 lysis protein so that the produced pyocin S5 is released from the cells, leading to the killing of *P. aeruginosa*. The engineered *E. coli* may effectively sense and kill *P. aeruginosa*; thereby providing a novel synthetic biology-based antimicrobial strategy that may be applied to eradicating other infectious pathogens.

The quorum sensing mechanisms of *P. aeruginosa* may enable the engineered microbes to produce pyocin S5 only in response to the presence of *P. aeruginosa*. The term "quorum sensing" as used herein refers to the intercellular communication between bacteria. This sensing mechanism is mediated by various diffusible, chemical signals known as autoinducers that are produced by the synthase genes of the bacteria. The extracellular concentration of signaling molecules increases as a function of cell density and is permeable to cell membrane. Upon attaining a threshold concentration of the chemical signals, the quorum sensing cascade is activated to elicit expressions or repressions of multiple genes, including those that are functional for production of autoinducers such as acyl homoserine lactones (AHLs). This organic signaling cascade therefore regulates a myriad of physiological activities such as cell motility, virulence, biofilm formation and growth. Although similar production mechanisms are present in some Gram-negative bacteria, each synthase homolog producing AHLs differs in either length or functional groups (e.g., hydroxyl and carbonyl groups) on the acyl side chain. Thus, with each bacterium possessing disparate synthase sequence, a high level of specificity can be achieved during intercellular quorum communication.

In various embodiments, the E7 lysis protein may be utilised to lyse the *E. coli* chassis to enable an effective release of pyocin S5. The E7 lysis protein is a key component of the SOS response system in colicin-producing cells and functions to export bacteriocins into the extracellular space under stressful environmental conditions. The E7 lysis protein may be effective in causing inner membrane damage and maybe associated with the activation of outer membrane phospholipase A for outer membrane modification. In addition to being specific to *E. coli*, the E7 lysis protein is small at 47 amino acids and may be easily utilized as a modular part in the assembly of novel genetic circuits.

Based on the above mentioned system, the isolated nucleic acid molecule in accordance to various embodiments may comprise the nucleotide sequence set forth in SEQ ID NO:4. For example, SEQ ID NO:4 may be LasR-$P_{luxR}$-pyocin S5-$P_{luxR}$-E7 lysis.

In some examples, the isolated nucleic acid molecule may include $P_{tetR}$-LasR-$P_{luxR}$-pyocin S5-$P_{luxR}$-E7 lysis (SEQ ID NO:6).

In various embodiments, the isolated nucleic acid molecule may be comprised in a vector.

As used herein, the term "vector" relates to any means by which a nucleic acid can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and the like, that are "episomes", that is, that replicate autonomously or may integrate into a chromosome of a host cell. For example, a vector may also be a naked RNA polynucleotide, a naked DNA polynucleotide, a polynucleotide composing both DNA and RNA, a liposome-conjugated DNA, or the like, that are not episomal in nature, or it may be an organism which comprises one or more of the above polynucleotide constructs such as an *agrobacterium*.

In a second aspect, a recombinant microorganism is provided. The recombinant microorganism comprises the isolated nucleic acid molecule as defined above.

The term "recombinant microorganism" refers to a microorganism that has been genetically modified to express or over-express endogenous polynucleotides, or to express non-endogenous sequences, such as those included in a vector, or which have a reduction in expression of an endogenous gene. The polynucleotide generally encodes a target enzyme involved in a metabolic pathway for producing a desired metabolite.

The recombinant microorganism may be interchangeably referred to as a microbe, an engineered microbe, an engineering microbe, a sensing device or an engineered biological system.

In various embodiments, the recombinant microorganism may be *E. coli*.

In another aspect, a method of sensing and killing pathogenic microorganisms is provided. The method comprises contacting the recombinant microorganism as defined above with the pathogenic microorganism.

In various embodiments, the method may be a method of sensing and killing pathogenic microorganisms in a subject. The method may comprise administering the recombinant microorganism as defined above to the subject.

In various embodiments, the pathogenic microorganism may be a human pathogen. The term "human pathogen" may generally refer to any pathogenic microorganism that may cause disease in or death to a human being.

For example, the pathogenic microorganism may be selected from the group consisting of *Pseudomonas aeruginosa, Clostridium difficile, Escherichia coli, Helicobacter pylori, Salmonella, Vibrio cholera* and *Yersinia*. Preferably, *P. aeruginosa*. The term "pathogenic microorganism" may be as defined above.

In order that the invention may be readily understood and put into practical effect, particular embodiments will now be described by way of the following non-limiting examples.

EXAMPLES

Materials and Methods

Strains and Media

Figure 7A:
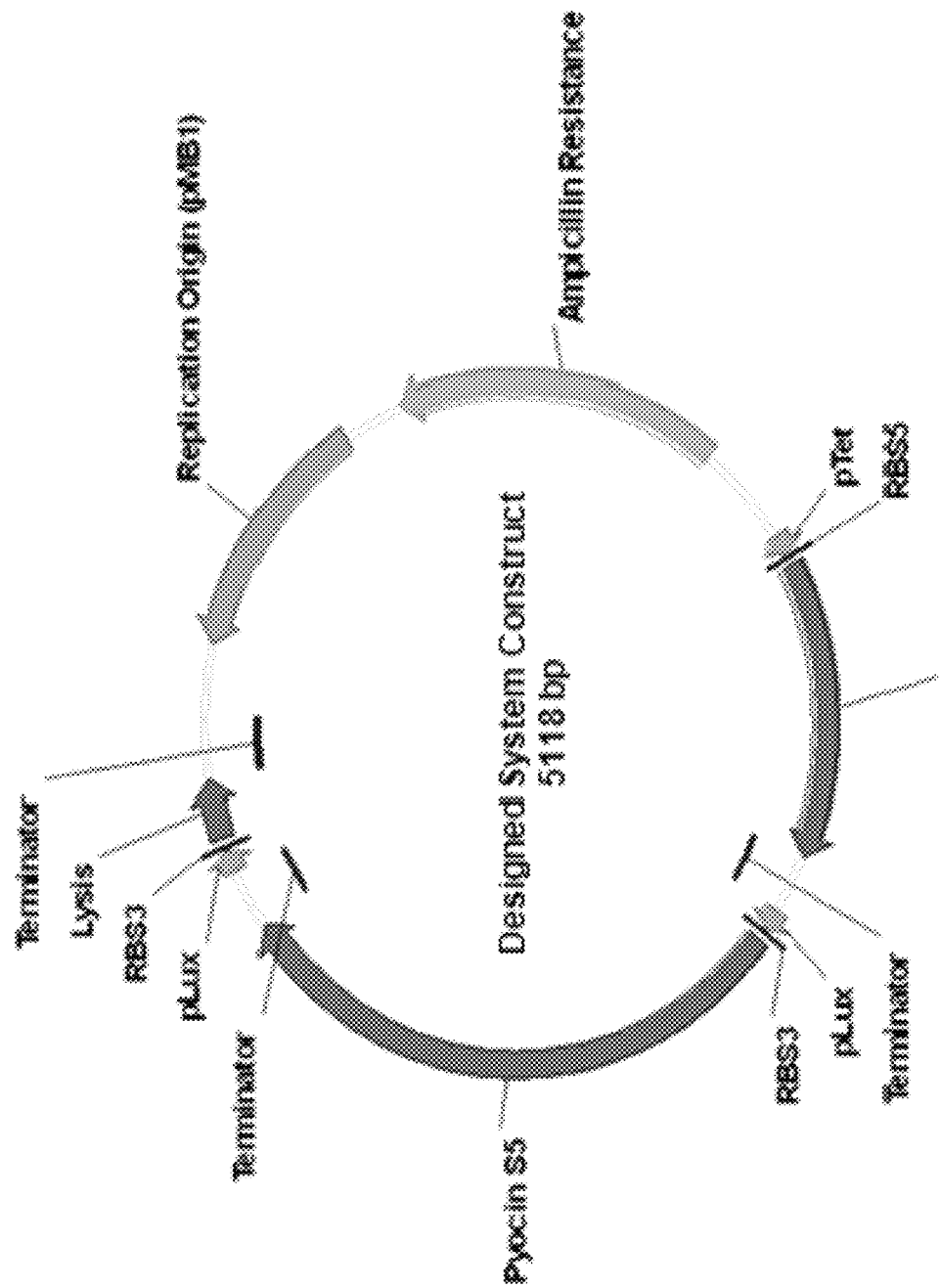

All cells involved in cloning and characterization are *E. coli* TOP10 (Invitrogen) unless otherwise stated. Commercial Luria-Bertani (LB) and Muller Hinton (MHB) were used as the medium for cloning and inhibition studies unless otherwise stated. Supplemented M9 (M9 salts, 1 mM thiamine hydrochloride, 0.4% glycerol, 0.2% casamino acids, 0.1M $MgSO_4$, 0.5M $CaCl_2$) was used as the medium for the characterization. Ampicillin (100 µg/ml) was added to the culture media for antibiotic selection where appropriate. Homoserine lactone ($3OC_{12}HSL$; Sigma Aldrich) was used for characterization experiments. All restriction and ligation enzymes were purchased from New England Biolabs (NEB). FIG. 7E summarizes all plasmids, Biobrick parts, and devices used in this example. The part number, functional description and symbol used are listed for each component. Descriptions of all BBa parts may be found in the Registry of Standard Biological Parts while the rest are explained herein.

Genetic mapping of representative engineered constructs is illustrated in FIGS. 7A-7D.

System Assembly

The genetic constructs developed in this example were assembled using standard synthetic biology protocols. Briefly, for front insertion of Biobrick parts, purified insert and vector plasmids were digested with EcoRI/SpeI and EcoRI/XbaI respectively. For back insertion to upstream vector, the insert and vector plasmids were digested with XbaI/PstI and SpeI/PstI in that order. Digested fragments were separated by DNA gel electrophoresis and ligated with NEB Quick Ligase in accordance with the manufacturer's instructions. Plasmids from chemically transformed cells were purified by affinity columns and verified by DNA sequencing.

Characterization of pTetR-LasR pLuxR-GFP with $3OC_{12}HSL$

Single colonies of pTetR-LasR-pLuxR-GFP (Top10) were each inoculated into 5 ml of pre-warmed supplemented M9 ampicillin for overnight culture in a shaking incubator at 37° C. After overnight growth, the cultures were diluted to $OD_{600}$ of 0.002 and allowed to incubate further to $OD_{600}$ of 0.5 or 5.0E7 cfu/ml under the same condition. Cultures were then transferred into a transparent, flat-bottom 96-well plate in triplicate aliquots of 200 µl for induction with $3OC_{12}HSL$ at varying molar concentrations (0, 5.0E-10, 1.0E-9, 5.0E-9, 1.0E-8, 5.0E-8, 1.0E-7, 2.5E 7, 5.0E-7, 1.0E-6, 5.0E-6, 1.0E-6, 5.0E-5, and 1.0E-4M). The plate was incubated at 37° C. with rapid shaking in a microplate reader (Biotek) and assayed for green fluorescence. Time-series fluorescence and $OD_{600}$ data were obtained at intervals of 10 mins for a total run time of 3 hrs. The measurement was zeroed with supplemented M9 to remove background fluorescence and $OD_{600}$. A relative GFP production rate was derived as a ratio of background subtracted green fluorescence to $OD_{600}$ value. A time-averaged GFP synthesis rate was obtained by averaging the relative GFP production rates between 20 and 80 mins after induction with $3OC_{12}HSL$. The measured data were fitted using an empirical mathematical model (Hill equation) as seen in Equation (1):

$$Y=A+(B[C_{12}]^n/(C^n+[C_{12}]^n)) \quad (1)$$

Equation (1) models GFP synthesis rate (y) as a function of input concentration of $3OC_{12}HSL$ ([C12]). The four parameters (A, B, C, n) were estimated to obtain the best fit curve by performing a non-linear curve fitting using the experimental results. This curve fitting was performed using MATLAB Curve Fitting Toolbox (The Mathworks, Natwick, Mass., USA).

Detection of the Native Autoinducer Produced by *P. Aeruginosa*

GFP production rates induced by $3OC_{12}HSL$ natively produced from *P. aeruginosa* were measured with pTetR-LasR-pLuxR quorum sensor as described above. Briefly, overnight cultures of pTetR-LasR-pLuxR-GFP (Top10) were diluted in Supplemented M9. Diluted *Pseudomonas* cultures were grown to a late logarithmic phase and filtered with a filter membrane (0.22 µm). Sterile filtrates containing $3OC_{12}HSL$ were mixed with pTetR-LasR-pLuxR-GFP culture to activate GFP production. The resultant mixtures were transferred into a transparent, flat-bottom 96-well plate in triplicate aliquots of 200 µl to be assayed for GFP production rates in a microplate reader (Biotek) at 37° C. with rapid shaking. The rates obtained were then compared with the Hill function mathematical model as in Equation (1) using $3OC_{12}HSL$ to estimate the native $3OC_{12}HSL$ concentration from *P. aeruginosa ln* 7.

Characterization of Lysis Device with $3OC_{12}HSL$

Overnight cultures of pTetR-LasR-pLuxR-E7 (Top10) were diluted in supplemented M9 and harvested at an $OD_{600}$ of 0.5. The resultant cultures were transferred into a transparent, flat-bottom 96-well plate in triplicate aliquots of 200 µl for induction with $3OC_{12}HSL$ at varying concentrations (i.e., 0, 1.0E-8, 1.0E-6, and 1.0E-4M). The plate was incubated at 37° C. with rapid shaking in a microplate reader (Biotek) and assayed for cell turbidity. Time-series absorbance at $OD_{600}$ was obtained at intervals of 10 mins for a total run time of 6 hrs. The result was zeroed with supplemented M9 to remove background absorbance.

FESEM Assay

To examine the effect of E7 lysis protein on cell morphology, reinoculated cultures of pTetR-LasR-pLuxR-E7 (Top10) and pTetR-LasR-pLuxR-S5-pLuxR-E7 (Top10) were induced with 1.0E-6M $3OC_{12}HSL$ at $OD_{600}$ of 0.5 and cultured for 2 hrs. Cell pellets collected after centrifugation at 4000 rpm for 15 mins were washed with 0.1M sodium cacodylate (pH 7.4) three times before fixation with 2.5% glutaraldehyde in 0.1M sodium cacodylate for 2 hrs of incubation at 4° C. Cell pellets were further washed three times with sodium cacodylate after fixation and resuspended in 0.1M sodium cacodylate (volume depends on cell amount). In all, 2 µl of sample was loaded onto PEI-coated silicon slide followed by incubation at 25° C. for 30 mins. The loaded silicon slide was fixed in 1% osmium tetraoxide in 0.1M sodium cacodylate at 25° C. for 90 mins. Silicon slide was then dehydrated in serial concentrations of absolute ethanol (37, 67, 95% and three times of 100%) for 15 mins each before drying in a vacuum evaporator overnight. Coating of silicon slide was performed with 20 nm of gold-palladium alloy (60:40) and examined using a field-emission scanning electron microscope (JSM-6700F FESEM) at 10 kV.

Characterization of Lysis Device by Protein Release in Engineered E. Coli

To characterize the efficiency of the lysis device in mediating pyocin release, pTetR-LasR-pLuxR-S5-pLuxR-E7 and pTetR-LasR-pLuxR-S5 plasmids were first labeled with hexa-histidine tags on the 3' terminus of S5 gene with pfu polymerase (Promega) and transformed into E. coli Top10. Overnight cultures of the His-tag version of pTetR-LasR-pLuxR-S5-pLuxR-E7 and pTetR-LasR-pLuxR-S5 were then diluted in LB and harvested at an $OD_{600}$ of 0.7. The collected cultures were induced with 1.0E-6M $3OC_{12}HSL$ and incubated for 6 hrs in a shaking flask culture set at 37° C. and 170 rpm. At regular intervals of 2 hrs, cell cultures were drawn and filter sterilized (0.22 µm). The filtered cultures were mixed with 1/10 volume of 100% (w/v) trichloroacetic acid (Sigma-Aldrich) and incubated on ice for 1 hr to allow protein precipitation, before being washed with an equal volume of acetone. Precipitated proteins were reconstituted in 1 ml of reconstitution solvent (1×PBS, 30 mM imidazole and 4M urea; pH 6.0) and purified by immobilized metal affinity chromatography using Vivapure miniprep MC (Sartorius Stedim Biotech GmbH) in accordance to the manufacturer's instruction. Finally, purified pyocin proteins were analyzed by SDS-PAGE and Bradford assay.

Overlay Inhibition Assay with $3OC_{12}HSL$ and the Final System

Overnight cultures of pTetR-LasR-pLuxR-S5-pLuxR-E7 (Top10), P. aeruginosa ln 7 and PAO1 were diluted in LB and harvested at $OD_{600}$ of 0.7 and 0.2 separately. Collected cultures of pTetR-LasRpLuxR-S5-pLuxR-E7 (Top10) were induced with varying molar concentrations of $3OC_{12}HSL$ (0, 1.0E-8, 1.0E-6, and 1.0E-4M) and incubated for 2 hrs before being filtered with a filter membrane (0.22 µm). In all, 30 µl of sterile filtrate from each induced sample containing soluble S5 was spotted onto trypticase soy agar (TSA) plate in triplicates. Upon drying of spots, 0.1 ml of ln 7 at $OD_{600}$ of 0.2 in soft agar (1% peptone, 0.5% agar) pre-warmed at 55° C. was thinly filmed over the spotted TSA and allowed to dry completely. Resultant TSA plate was then incubated for 6 hrs at 37° C. before image analysis with Bio-Rad ChemiDoc XRS. To evaluate the effectiveness of the engineered system coupled with the sensing function, overnight culture of P. aeruginosa ln 7 was also harvested at $OD_{600}$ of 1.0 after redilution. The culture was filtered with a filter membrane (0.22 µm) and the sterile filtrate obtained, containing planktonic $3OC_{12}HSL$ was used to induce pTetR-LasR-pLuxR-S5-pLuxR-E7 (Top10). These procedures were repeated to capture inhibitory images for the engineered system that was activated by $3OC_{12}HSL$ natively produced from P. aeruginosa.

Co-Culturing of the Engineered E. Coli and P. Aeruginosa

GFP reporter plasmid pMRP9-1 and chloramphenicol-resistant plasmid pAWG1.1 were transformed into P. aeruginosa ln 7 and PAO1 using a method described hereinabove. Overnight cultures of P. aeruginosa (ln 7/PAO1 with pMRP9-1), pTetR-LasR-pLuxR-S5 (Top10), pTetR-LasR-pLuxR-E7 (Top10), and pTetR-LasR-pLuxR-S5-pLuxR-E7 (Top10) were diluted and harvested at an $OD_{600}$ of 1.0. pTetR-LasR-pLuxR-S5-pLuxR-E7 (Top10) was added to ln 7 or PAO1 in the ratio 4:1 to obtain a mixed culture with an overall cell density of 1.0E8 cfu/ml in 25 ml of MHB. The resultant mixture was grown for 15 hrs in a shaking flask culture set at 37° C. and 170 rpm. For fluorescence assays, the mixed culture was transferred into a transparent, flat-bottom 96-well plate in aliquots of 200 µl and assayed for background subtracted green fluorescence in a microplate reader (Biotek) at regular intervals of 3 hrs. The same procedures were repeated for pTetR-LasR-pLuxR-S5 (Top10) and pTetR-LasR-pLuxR-E7 (Top10) as negative controls. For cell viability assays, aliquots of P. aeruginosa in the mixed culture were quantified by CFU count on chloromphenicol selective agar plates at regular intervals of 5 hrs. The same procedures were repeated for pTetRLasR-pLuxR-S5 (Top10) and pTetR-LasR-pLuxR-E7 (Top10) as negative controls.

Percentage survival of planktonic P. aeruginosa was determined as follows in Equation (2):

$$\text{Percentage cell survival} = \frac{CFU \text{ of } P.aeruginosa \text{ in treated sample at time } t \times 100}{CFU \text{ of } P.aeruginosa \text{ treated with WT } E.coli \text{ at time } t} \quad (2)$$

Live and Dead Fluorescent Microscopy

Overnight cultures of ln 7 and pTetR-LasR-pLuxR-S5-pLuxR-E7 (Top10) were diluted in LB and harvested at an $OD_{600}$ of 0.5 and 1.0, respectively. $3OC_{12}HSL$ from ln 7 was obtained after passing ln 7 culture through a filter membrane (0.22 µm) and the sterile filtrate was used to induce expression of engineered system by mixing it with pTetR-LasR-pLuxR-S5-pLuxR-E7 (Top10) in 1:1 mixing ratio to a total volume of 2 ml. The resultant culture was grown for 3 hrs and filtered with a similar membrane to obtain sterile S5 filtrate. The filtrate was mixed with ln 7 at $OD_{600}$ of 1.0 in 1:1 mixing ratio to a total volume of 2 ml and incubated for 3 hrs. One microliter of the final culture was stained with bacterial viability kit (Invitrogen) according to the manufacturer's instruction and analyzed with a fluorescent microscope (Zeiss Axio Scope A1).

Biofilm Inhibition Assay

P. aeruginosa (ln 7/PAO1 with pAWG1-1) conferred with chloramphenicol resistance was mixed with pTetR-LasR-pLuxR-S5-pLuxR-E7 (Top10) in the ratio 1:4 to obtain a mixed culture with an overall cell density of 1.0E8 cfu/ml in 6 ml of MHB. The resultant mixture was transferred to the wells of a polystyrene microtiter plate (Iwaki) in aliquots of 1 ml each and grown at 37° C. and 150 rpm. After 18 hrs of growth, biofilm on the microtiter plate was rinsed and recovered in fresh MHB by sonication and quantified by CFU count on chloramphenicol-selective plate (100 mg/ml). The same procedures were repeated for ln 7 treated with pTetR-LasR-pLuxR-S5 (Top10) and pTetR-LasR-pLuxR-E7 (Top10), and PAO1 treated with pTetR-LasR-pLuxR-S5-pLuxR-E7 as negative controls. Percentage survival of *P. aeruginosa* biofilm was determined as follows in Equation (3):

$$\text{Percentage biofilm survival} = \frac{\text{CFU of } P.aeruginosa \text{ biofilm in treated sample} \times 100}{\text{CFU of } P.aeruginosa \text{ biofilm in treated with WT } E.coli} \quad (3)$$

Confocal Microscopy of Biofilm

Mixed bacteria cultures of *P. aeruginosa* (ln 7 with pMRP9-1) and engineered *E. coli* systems were grown in MHB in 50 ml tubes containing sterile glass slide. Biofilm developed on the glass slides after 18 hrs of growth was rinsed in PBS, dried, and visualized by confocal laser scanning microscopy (Zeiss LSM 510). Collected Z-stack biofilm images were reconstructed using Zeiss 2.5D software.

Example 1

Detection of Naturally Secreted Quorum Sensing Molecules by the *P. Aeruginosa* Cells and Biofilm as Determined by the GFP Reporter Protein To verify the response of QS device against the natively expressed quorum sensing molecule (N-Acyl homoserine lactone; AHL), pE8k-pLasI-GFP transformed *E. coli* was co-cultured with synthetic AHL, culture supernatant or mature biofilm of *P. aeruginosa* cells and assayed for GFP expression. The resulting GFP fluorescence in response to 1000-fold diluted supernatant (OD 1.0) was equivalent to ~10-8M AHL (FIGS. 9A-9D). Therefore, it can be estimated that the concentration of AHL present in supernatant is as high as 10-5M. This validated the sensitivity of the QS device for activating and responding (downstream expression) to the presence of *P. aeruginosa* (PAO1) cells at even low density.

Example 2

Expression and Secretion of Antimicrobial Peptide Microcin S Upon the Detection of Quorum Sensing Molecules Naturally Secreted by *P. Aeruginosa*

Figure 10:
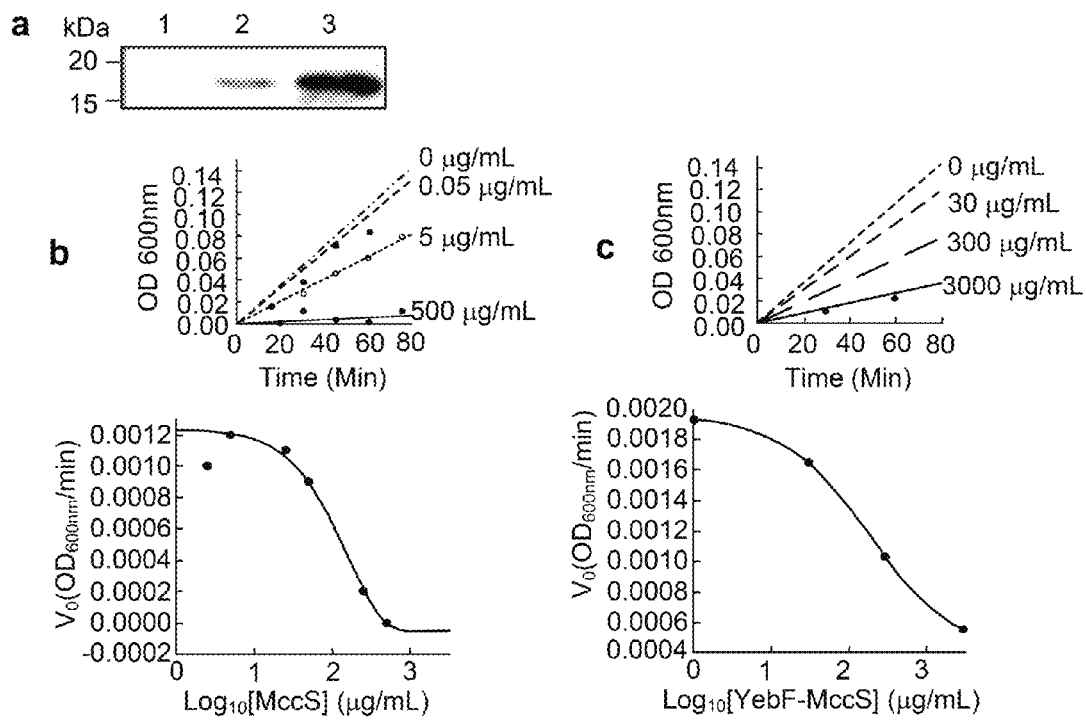
FIG. 10: Analysis of antimicrobial activity of Microcin S (MccS) against *P. aeruginosa* (a) Expression and purification of MccS. Lanes (1) Untreated *E. coli* (ΔcheZ mutant) harboring pBbE8k-pLasI-MccSH6 plasmid, (2) transformed *E. coli* (ΔcheZ mutant) with AHL induction, and (3) purified MccS. (b) Various concentrations of purified MccS were tested against *P. aeruginosa* (PAO1) and the effect on growth rate was compared. *Inset graph: OD value was normalized to the start of the exponential phase. (c) Extracellular expression of YebF-MccS fusion protein after 3 h of induction with 1 µM AHL. The YebF-MccS fusion protein was concentrated using molecular weight cut-off centrifuge filtration and assayed for its activity against *P. aeruginosa* (PAO1). Resulting protein concentration of extracellular medium containing secreted YebF-MccS was quantified using the Bradford assay and corresponding effect on cell growth was assayed. Half maximal inhibitory concentration (IC50) of YebF-MccS against *P. aeruginosa* (PAO1) cells was determined. Control (0 µg/mL) is extracellular medium without AHL induction.

Microcin S (MccS) is antimicrobial peptide that has shown a killing efficiency against a wide range of Gram-negative microbes (Zschüttig et al, 2012). Its expression in *E. coli* was first characterized (FIG. 10a). The bactericidal activity of MccS against *P. aeruginosa* (PAO1) was demonstrated by incubating *P. aeruginosa* (PAO1) with a range of concentrations of purified MccS (FIGS. 10a and 10b). For each growth assay, the change in $OD_{600}$ during exponential growth phase was compared to the corresponding change in the control. Although the MccS was identified in other study (Zschüttig et al, 2012), its highly effective bactericidal activity against *P. aeruginosa* (PAO1) is demonstrated in this study for the first time, exhibiting an $IC_{50}$ of 14.7 µg/mL.

Figure 11:
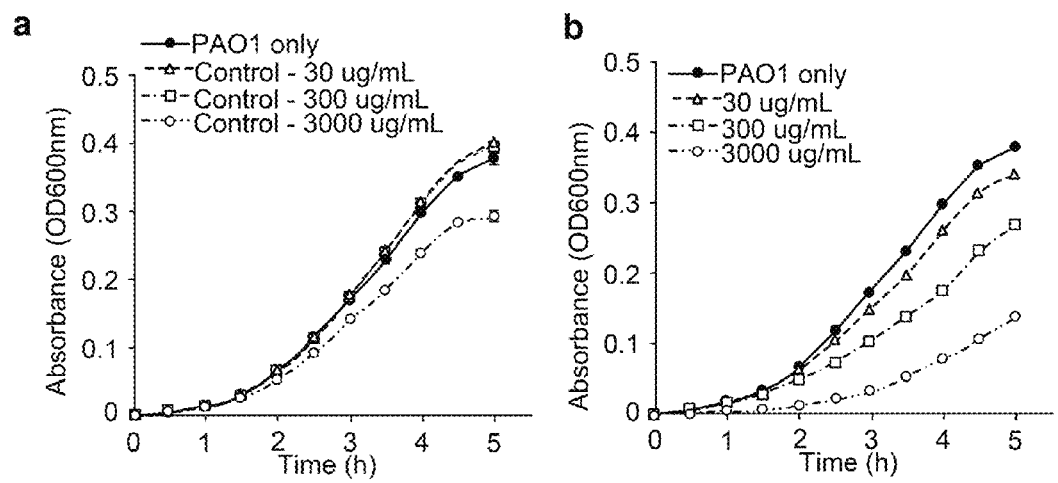
FIG. 11: Growth curves of *P. aeruginosa* PAO1 under different concentration of secreted YebF-MccS. A change in cell growth (OD600 value) of *P. aeruginosa* (PAO1) cells incubated with concentrated extracellular medium from (a) control or (b) YebF-MccS expressing *E. coli* cells was observed over 5 h.

Secretion of MccS was promoted by the fusion of a secretion tag, YebF, to the N-terminus of MccS. YebF is a small, soluble endogenous protein, which can carry fusion proteins in their active states to the medium, as early as 3 h after induced expression. The activity of fusion peptide, YebF-MccS, in extracellular medium after 3 h induction remained active against *P. aeruginosa* (PAO1) cells. The extracellular medium was collected and concentrated using molecular weight cut off (MWCO) filtration unit to selectively collect proteins within 5 kDa to 30 kDa range as the estimated YebF-MccS was approximately 25 kDa. The activity of the YebF-MccS in the extracellular medium was demonstrated against *P. aeruginosa* (PAO1) (FIG. 10c, FIG. 11). Approximate $IC_{50}$ of the secreted protein was 188 µg/mL, which indicates that the addition of the YebF to MccS resulted in approximately 10-fold increase in $IC_{50}$ value.

Example 3

Targeted Cell Killing by the Secreted Antimicrobial Peptide, Microcin S Upon the Detection of Quorum Sensing Molecules Naturally Secreted by *P. Aeruginosa*

Figure 12:
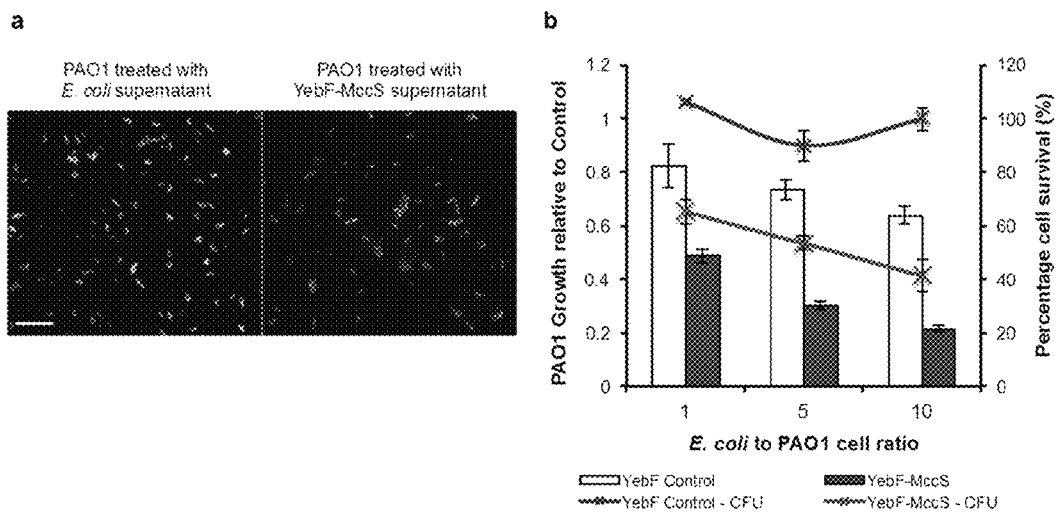
FIG. 12: Analysis of antimicrobial activity of Microcin S (MccS) against *P. aeruginosa* (a) *P. aeruginosa* (PAO1) cells expressing GFP after treatment with YebF-MccS were stained with PI dye to determine dead cells. The bar represents 10 µm. (b) YebF-MccS expressing *E. coli* was co-cultured with GFP expressing *P. aeruginosa* (PAO1) cells at the given relative cellular ratio and the resulting effect on growth rate and cell viability was evaluated. Growth relative to control after 12 h of incubation was calculated by taking the arbitrary GFP fluorescence intensity of co-cultured sample relative to untreated *P. aeruginosa* (PAO1) with GFP expression. YebF control refers to *E. coli* expressing YebF protein.

Further, cell killing by the MccS secreted by the reprogrammed *E. coli* has been verified by Live/Dead cell viability assay (FIG. 12a). *P. aeruginosa* (PAO1) cells treated with YebF-MccS showed significant proportion of cells stained with PI dye indicating cell death, whereas the cells treated with the control supernatant were mostly stained with SYTO 9 dye, which denotes that most cells are viable. Therefore, the extracellular medium containing secreted YebF-MccS remained active and caused significant inhibition against *P. aeruginosa* (PAO1) cell growth.

To further verify whether the killer cell construct could autonomously sense the presence of *P. aeruginosa* (PAO1) cells to initiate cell-killing, co-culture of the YebF-MccS secreting *E. coli* with *P. aeruginosa* (PAO1) was set up. *P. aeruginosa* (PAO1) constitutively expressing GFP was co-cultured with *E. coli* at the indicated starting cell ratio based on $OD_{600}$ value and subsequent GFP fluorescence and viable *P. aeruginosa* (PAO1) cells were measured after 12 h of incubation. Significant reduction in growth rate and cell viability of *P. aeruginosa* (PAO1) was achieved at equivalent starting $OD_{600}$ of *E. coli* cells (FIG. 12b).

Example 4

Figure 13:
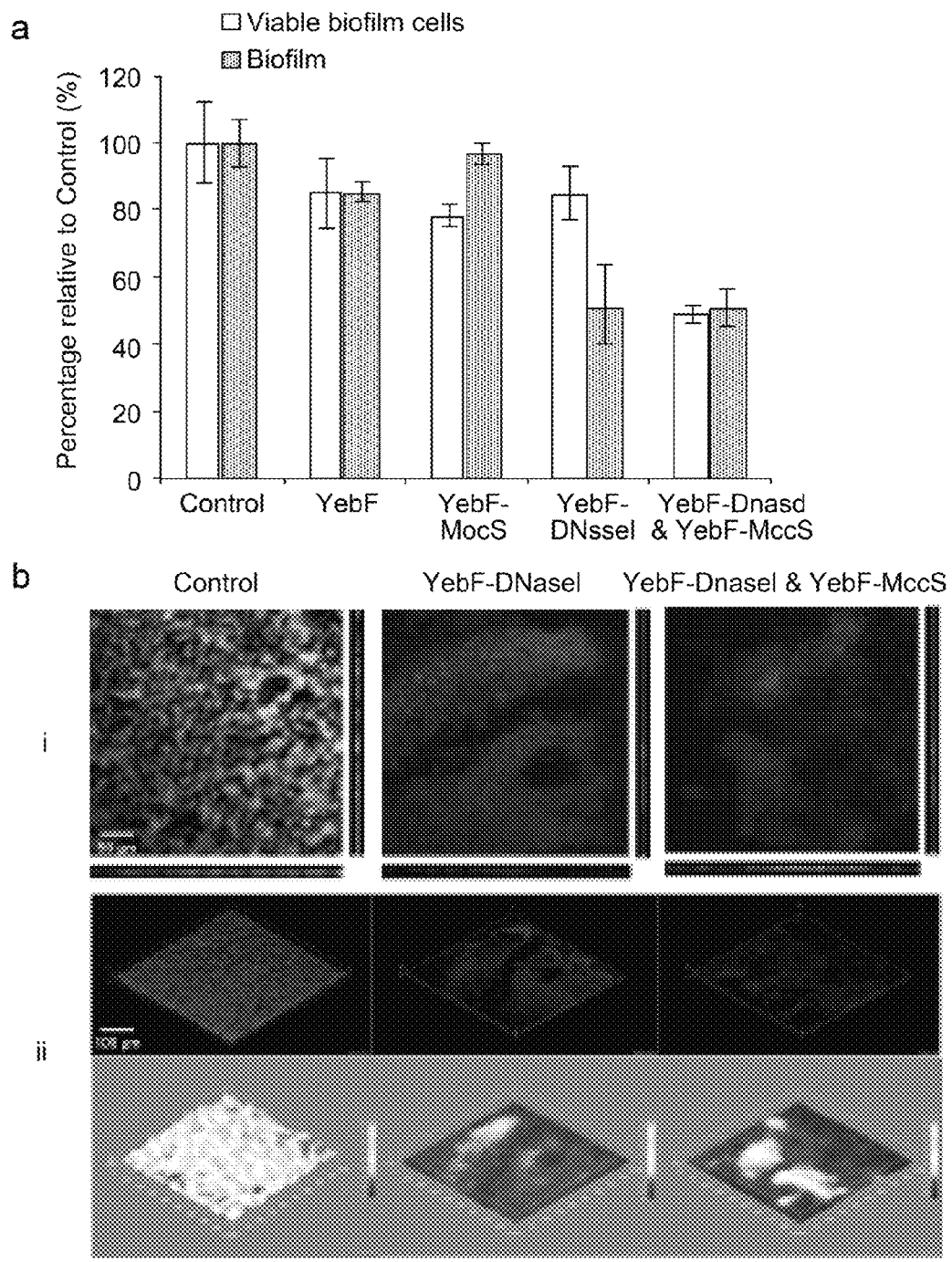
FIG. 13: Analysis of antibiofilm activity of DNaseI against *P. aeruginosa*. (a) The mature biofilm was incubated with the engineered *E. coli* cells for 16 h and the resulting biofilm was stained with crystal violet and quantified by taking absorbance reading at 595 nm. Viable biofilm cells were also determined by performing CFU counting after 16 h incubation of mature biofilm with *E. coli* cells. (b) Antibiofilm activity of DNaseI was observed under confocal laser scanning microscopy (CLSM). (i) *Pseudomonas* biofilm with green fluorescence was grown on 8-well chambered glass slide for 48 h and subsequently treated with the engineered *E. coli* for 16 h and visualized under CLSM. Scale bar represents 50 μm. (ii) Images were reconstructed from biofilm Z-stacks using Image J. Scale bar represents 100 μm.
Figure 14:
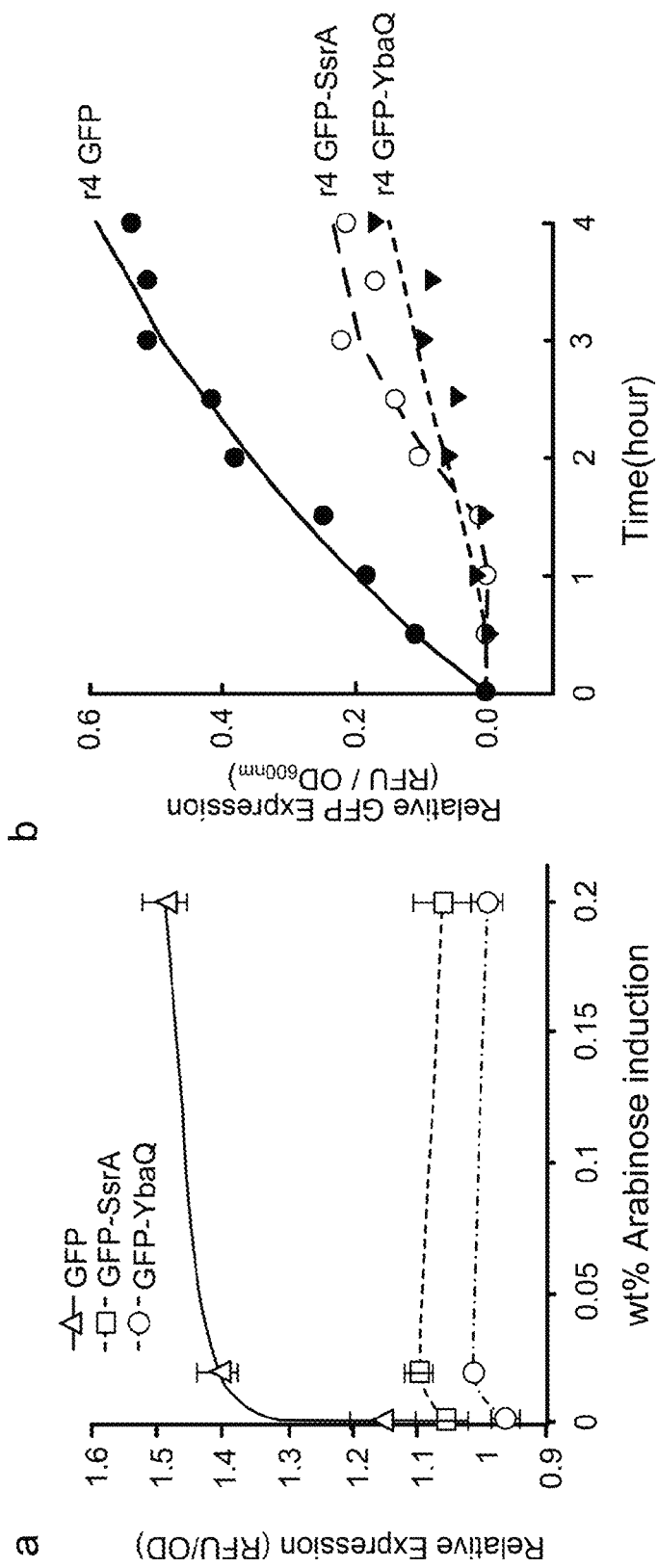
FIG. 14: Post-translational modulation by degron-fusion. To implement post-translational modulation of CheZ level via degron, GFP fused with SsrA or YbaQ was assayed for its fluorescence. (a) GFP expression induced by the different inducer concentration after 16 h with degradation tags showed lowered expression. (b) At 0.2% arabinose induction, GFP-YbaQ was more efficient in lowering the steady-state level of GFP over time.

Expression and Secretion of Antimicrobial Peptide Microcin S and Nuclease DnaseI Allowing the Degradation of Biofilm Matrix and Eradication of Biofilm-Encased Pathogens The reprogrammed cells were also designed to detect and target biofilm matrix of *P. aeruginosa* (PAO1) by secreting antibiofilm nuclease, bovine pancreatic DNaseI. When the YebF-DNaseI transformants were co-cultured with *P. aeruginosa* (PAO1) mature biofilm, the expression was sufficiently induced and consistent detachment of biofilm was observed (FIGS. 13a and 13b). The extent of biofilm detachment was not affected when the cell was expressing both YebF-DNaseI and YebF-MccS. When the viable biofilm cells were counted, only cells expressing both proteins significantly reduced biofilm mass as well as viable biofilm cells. However, YebF-MccS alone did not have any effect against biofilm or biofilm-encased *P. aeruginosa* (PAO1) cells. This result indicates that our reprogrammed cells secreting antimicrobial peptide (MccS) and DnaseI exerted significant biofilm degradation and cell killing that are autonomously induced in the presence of *P. aeruginosa* (PAO1) cells and mature biofilm.

Example 5

Directing Motility of Engineered *E. Coli* Towards the Pathogen Through Regulated Expression of CheZ When *E. coli* lacks cheZ, an integral member of the chemotaxis signaling pathway (ΔcheZ), the cells tumble incessantly and are essentially non-motile (Huang & Stewart, 1993). With this ΔcheZ strain, *P. aeruginosa* (PAO1) it was tested if -dependent motility could be re-established by expressing CheZ in response to AHL. Therefore, cheZ gene was introduced under the control of a LasR-AHL activator responsive promoter, pLasI, and expressed in *E. coli* (ΔcheZ mutant). As prior studies reported that over-expression of CheZ abolishes chemotaxis (Huang & Stewart, 1993; Scharf et al, 1998), a range of expression level required for motility needed to be carefully regulated. To this end, a degron was employed to destabilize CheZ to reduce basal activity and broaden the responsive range of inducer concentration. Degrons are short amino acid sequences that are specifically degraded by the ClpXP or ClpAP complexes, resulting in an efficient degradation of the fused protein (Flynn et al, 2003; Shin & Noireaux, 2010). The level of destabilization was first characterized with GFP (FIG.) and the degron sequences were subsequently fused to the C-terminus of CheZ.

Figure 15:
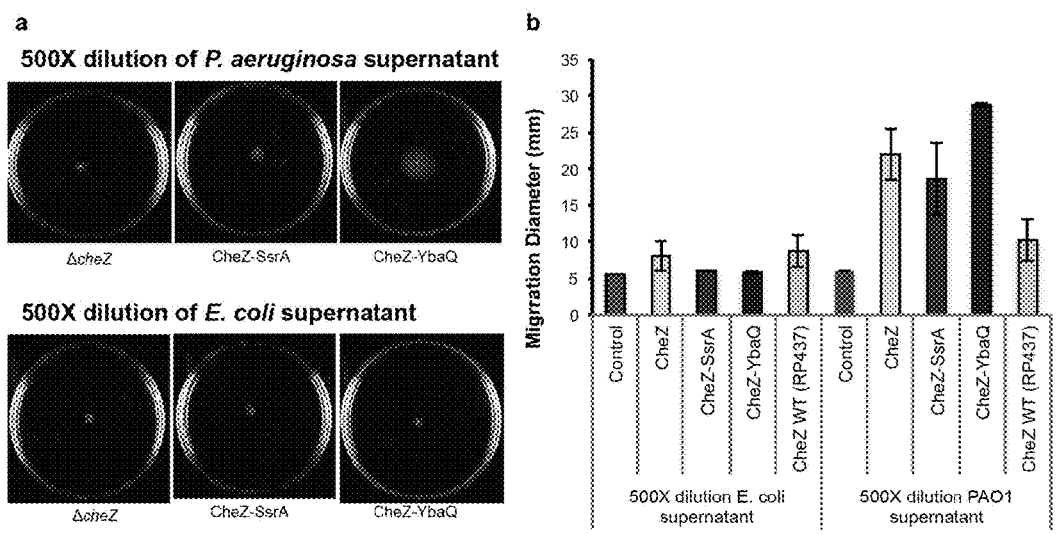
FIG. 15: Validation of specific response of *E. coli* cell motility to *P. aeruginosa*. (a) Image and (b) graph of distance migrated by the *E. coli* cell migration in the presence of *P. aeruginosa* (cellular supernatant). This migration was not observed in the supernatant of *E. coli* (AI-2), a known chemotactic factor for *E. coli*.
Figure 16:
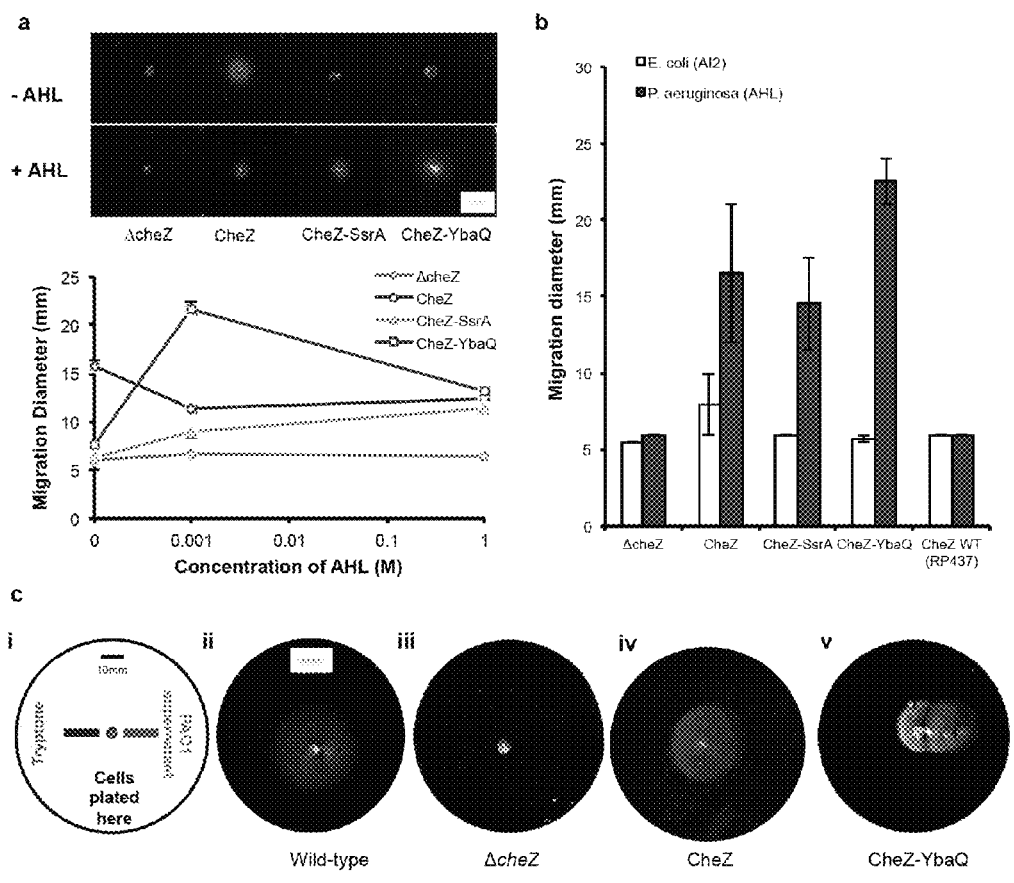
FIG. 16: Directed chemotaxis-guided motility of *E. coli* upon induction by quorum sensing molecule, AHL and by *P. aeruginosa*. (a) Migration of ΔcheZ cells expressing various CheZ variants on semi-solid media in the absence or presence of AHL (1 nM). The graph shows the average migration diameter of the cheZ-reconstituted cells as a function of AHL concentration when the cells were cultured at 30° C. for 16 h. (b) Migration of CheZ variants expressing cells in the presence of supernatant collected from *P. aeruginosa* PAO1 or *E. coli* cell cultures in exponential growth phase. CheZ deleted strain expressing: pLasI-CheZ, pLasI-CheZ-SsrA and pLasI-CheZ-YbaQ were compared to CheZ wild-type strain (RP437). (c) Directed cell motility of activated *E. coli* is specific to *P. aeruginosa*. (i) Diagram of plates containing semi-solid media spotted with *P. aeruginosa* PAO1 supernatant and Tryptone (growth media) as outlined. *E. coli* cells were plated at the center as shown and grown for 16 h at 30° C. (ii-v) Motility of wild-type *E. coli* strain (RP437), *E. coli* (ΔcheZ mutant), *E. coli* (ΔcheZ mutant) expressing CheZ, or CheZ-YbaQ.

Addition of the degron to CheZ resulted in a tight regulation on basal expression, while demonstrating specific motility upon AHL induction (FIG. 16a). The specificity of this motility was further confirmed by the preferential cell motility in the presence of *P. aeruginosa* (PAO1) supernatant (AHL) over *E. coli* supernatant (AI-2) (FIG. 15 & FIG. 16b). Furthermore, directed motility was demonstrated when the populations of CheZ-YbaQ expressing cells migrated towards the *P. aeruginosa* (PAO1) supernatant (FIG. 16c). Therefore, these results show that the reprogrammed chemotactic feature enabled the population of the cells to migrate up an AHL concentration, hence towards *P. aeruginosa* (PAO1).

Example 6

Figure 17:
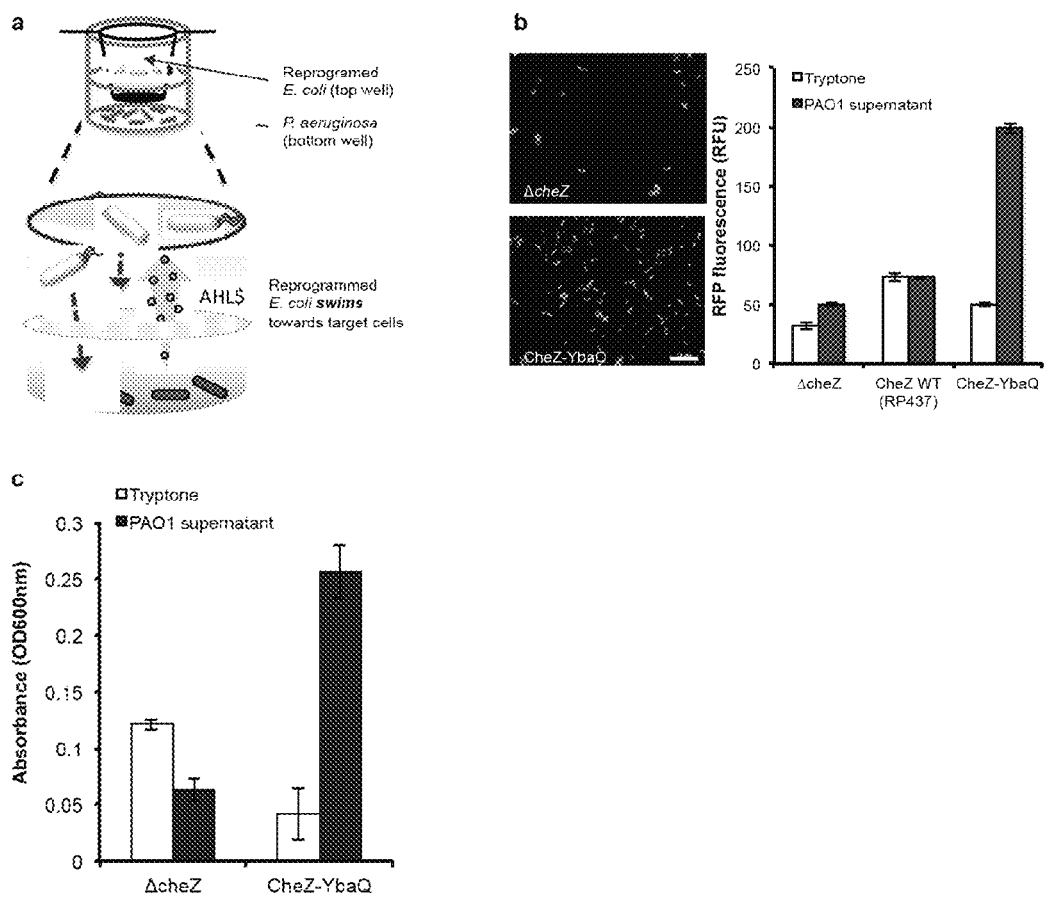
FIG. 17: Testing the final construct for efficient QS-mediated motility with biofilm-disrupting and cell killing— Seek and Kill system. (a) Schematic depicts AHL-directed cell motility of the reprogrammed *E. coli* (from the inverted transwell insert) towards the PAO1 cells initially seeded on the bottom of the transwell apparatus. Due to the diffused AHL across the insert, the activated *E. coli* begins to swim vertically towards PAO1 due to AHL-induced CheZ expression. Subsequently, the expression of MccS and DNaseI for secretion mediates cell killing and disrupt biofilm matrix. (b) Specific motility of reprogrammed *E. coli* (pLasI-CheZ-YbaQ) across the transwell shown by microscopic images and graph of RFP fluorescence or (c) OD collected from the bottom well.

Evaluation of a Construct for Efficient QS-Mediated Motility with Biofilm-Disrupting and Cell Killing—Seek and Kill System The results shown in FIGS. 9 to 16 demonstrate successful reprogramming of chemotaxis towards *P. aeruginosa* (PAO1) (motility module) and the efficacy of MccS and DNaseI secreting cells (killing module) against *P. aeruginosa* (PAO1) cells in a co-culture system. Hence, the two modules were integrated with QS device to create the 'Seek and Kill' system in *E. coli* against *P. aeruginosa* (PAO1). In FIG. 1A, the assembled system is depicted, comprising sensing and motile killer *E. coli* cells that (i) detect QS molecules emanating from *P. aeruginosa* (PAO1) cells in planktonic and biofilm states, (ii) migrate towards *P. aeruginosa* (PAO1) cells/biofilm while also expressing antimicrobial and antibiofilm enzymes, and (iii) mediate biofilm disruption and cell killing. In FIG. 17a, the *E. coli* with integrated 'Seek and Kill' system (CheZ-YbaQ, YebF-MccS and YebF-DNaseI) were placed at the top compartment of a transwell apparatus with agar medium. Specific bacterial migration towards the targeted pathogen by adding culture supernatant of *P. aeruginosa* (PAO1) cells by measuring RFP fluorescence and $OD_{600}$ (FIGS. 17b and 17c) was examined after 16 h incubation (time used to observe directed motility and both '2-hit killing' activities of the engineered *E. coli*). Specific migration of *E. coli* was observed with CheZ-YbaQ expressing cells in the presence of *P. aeruginosa* (PAO1) culture supernatant, while other controls have shown basal level of migration.

Figure 18:
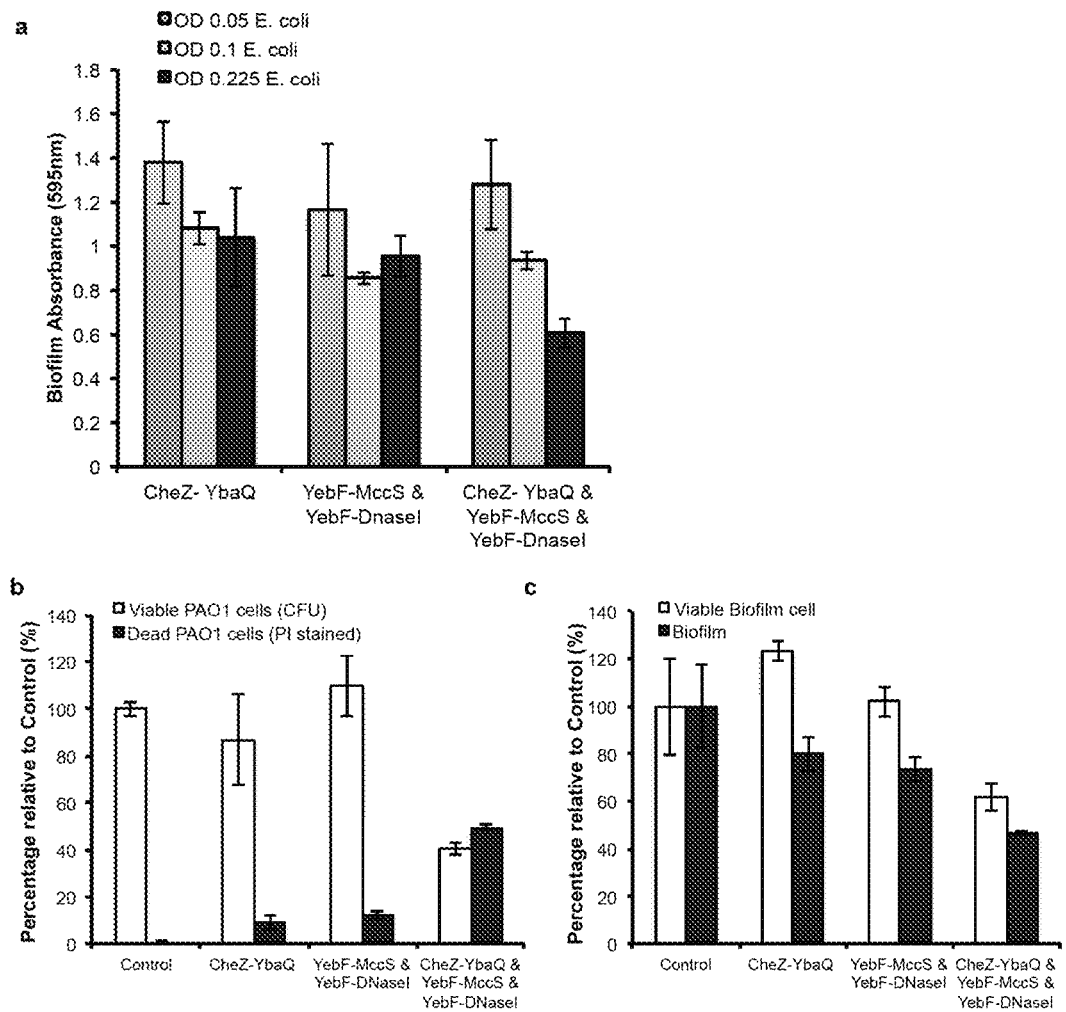
FIG. 18: Testing the final construct for efficient QS-mediated motility with biofilm-disrupting and cell killing— Seek and Kill system. (a) The transwell insert with reprogrammed *E. coli* was seeded on transwell containing *P. aeruginosa* PAO1. Different number of *E. coli* cells was seeded on transwell to determine effective biofilm degradation achieved after 16 h incubation. (b) The viability of PAO1 cells was measured after 16 h of incubation with reprogrammed *E. coli* on the transwell insert. Live/Dead BacLight kit was also used to determine cell death. The proportion of PI stained (dead) compared to SYTO9 stained (all) cells treated with *E. coli* expressing CheZ with MccS and DNaseI (pLasI-CheZ-YbaQ and McsI-pLasI-YebF-MccSH6-YebF-DNaseI) compared to non-motile MccS and DNaseI was compared (McsI-pLasI-YebF-MccSH6-YebF DNaseI). (c) The transwell insert with reprogrammed *E. coli* was seeded on the transwell containing mature PAO1 biofilm. After 16 h incubation, resulting biofilm and viable biofilm cells were determined using crystal violet staining and CFU counting respectively.

Once the *P. aeruginosa* (PAO1) responsive bacterial migration was established in this assay, the engineered *E. coli* with the integrated system was tested against *P. aeruginosa* (PAO1) cells and biofilm. Firstly, to determine the effective biofilm degradation to be achieved after 16 h incubation, different number of *E. coli* cells was seeded on the top compartment of the transwell insert. Subsequently reduction in biofilm matrix was assayed by crystal violet staining (FIG. 18a). The resulting viability of *P. aeruginosa* (PAO1) cells was tested by performing antibiotic-selective colony forming unit (CFU) counting once the most effect number of *E. coli* was seeded.

The *E. coli* with the integrated system showed approximately 60% reduction in survival cells while others with either motility (CheZ-YbaQ) or killing (YebF-MccS & YebF-DNaseI) module alone resulted in insignificant reduction in *P. aeruginosa* (PAO1) cell survival (FIG. 18b). This result was complemented with the highest percentage of dead cells (~50%) obtained from the Syto9-PI staining Therefore, with the fully integrated motility and killing system, the cells were able to achieve approximately 4-fold higher cell killing activity. Furthermore, when the integrated 'Seek and Kill' *E. coli* was tested against *P. aeruginosa* (PAO1) biofilm, 60% reduction in *P. aeruginosa* (PAO1) biofilm relative to the control was observed (FIG. 18c). Furthermore, complementary 40% reduction in viable *P. aeruginosa* (PAO1) biofilm cells was observed by the 'Seek and Kill' system. Taken together, the integrated system could respond to both planktonic and mature biofilm *P. aeruginosa* (PAO1) and exhibit cell migration and localization that accentuate cell killing activities of our engineered *E. coli*, which effectively resulted in reduction in *P. aeruginosa* (PAO1) cells and biofilm matrix.

Example 7

AHL-Reprogrammed 'Seek and Kill' System in *E. Coli*

Overall scheme of the strategic approach for this study is divided into 3 modules as outlined in FIG. 1A. The sensitivity of the quorum sensing (QS) device (sensing module) towards recognizing QS molecule (N-Acyl homoserine lactone; AHL) secreted by planktonic and biofilm *P. aeruginosa* cells and inducing the downstream expression is established. Therefore, in the presence of *P. aeruginosa*, the motility and killing modules are activated. The AHL-responsive chemotaxis is initiated to allow *E. coli* to swim up the concentration gradient of AHL, thereby localizing the cells closer to *P. aeruginosa* (motility module). Furthermore, the production and secretion of antimicrobial peptide, Microcin S (McCS) and antibiofilm enzyme (DNaseI) mediate '2-hit killing' by targeting both planktonic and biofilm-encased *P. aeruginosa* cells that are released by the biofilm degradation (killing module).

In summary, the engineered *E. coli* is able to integrate inputting signals from a target pathogen (quorum sensing molecules) into a programmed response, which comprised production and secretion of antimicrobial peptide and antibiofilm enzyme, and directed migration towards pathogenic *P. aeruginosa* cells for closer localization for concerted killing activity.

The biofilm formation plays a role in the pathogenesis of many chronic infections due to its resistance to conventional antimicrobial agents and host defenses. The strategy addressed this by utilizing antibiofilm enzyme (DNaseI), thus reducing the resistance provided by the biofilm structure. Concurrently, co-expression of antimicrobial peptide (MccS) by the engineered *E. coli* cells further eliminated the released dormant, resistant cells from the biofilm structure. Furthermore, never before has the killing activity of MccS been demonstrated against *P. aeruginosa*.

Example 8

Characterization of the Sensing Device

Figure 2A:
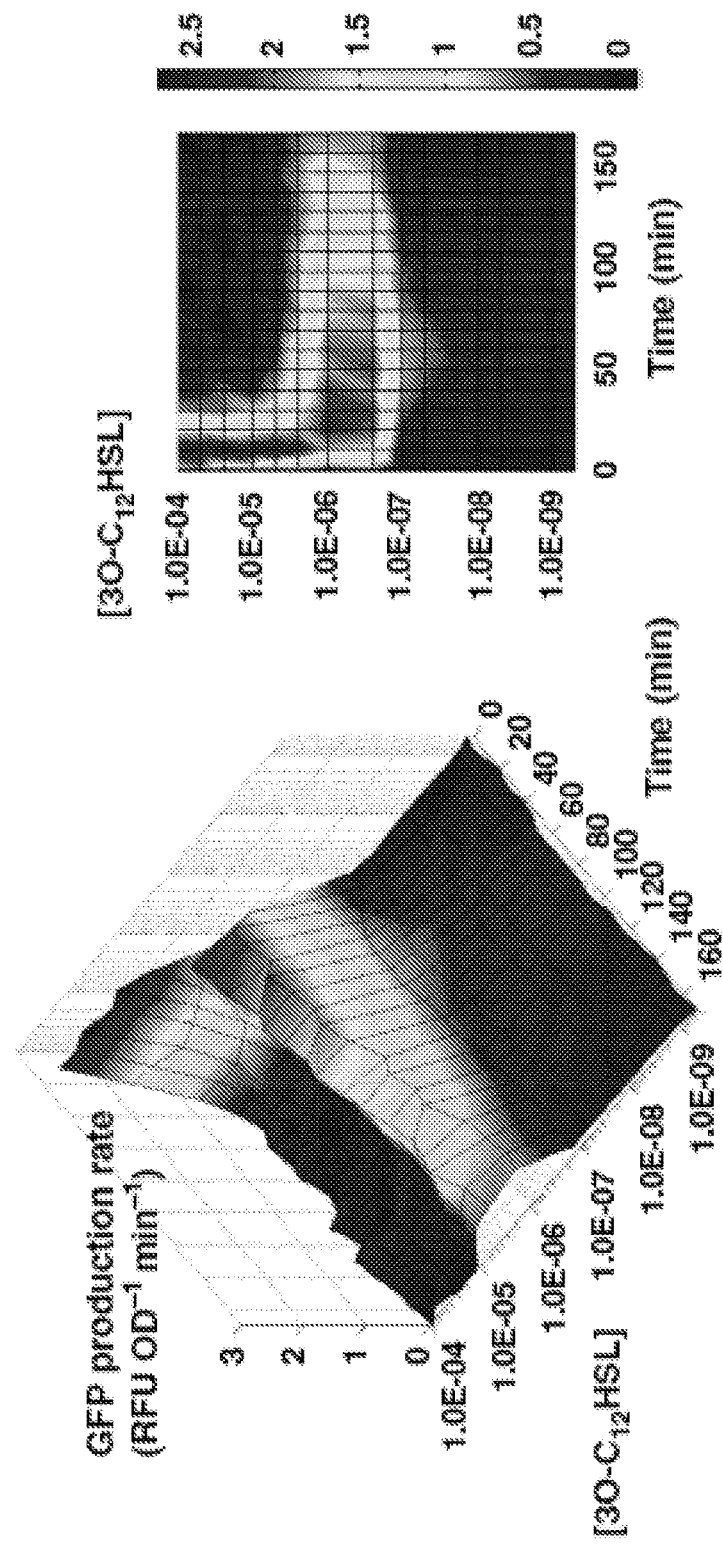
FIGS. 2A and 2B show the characterization of sensing device coupled with GFP reporter.
Figure 7B:
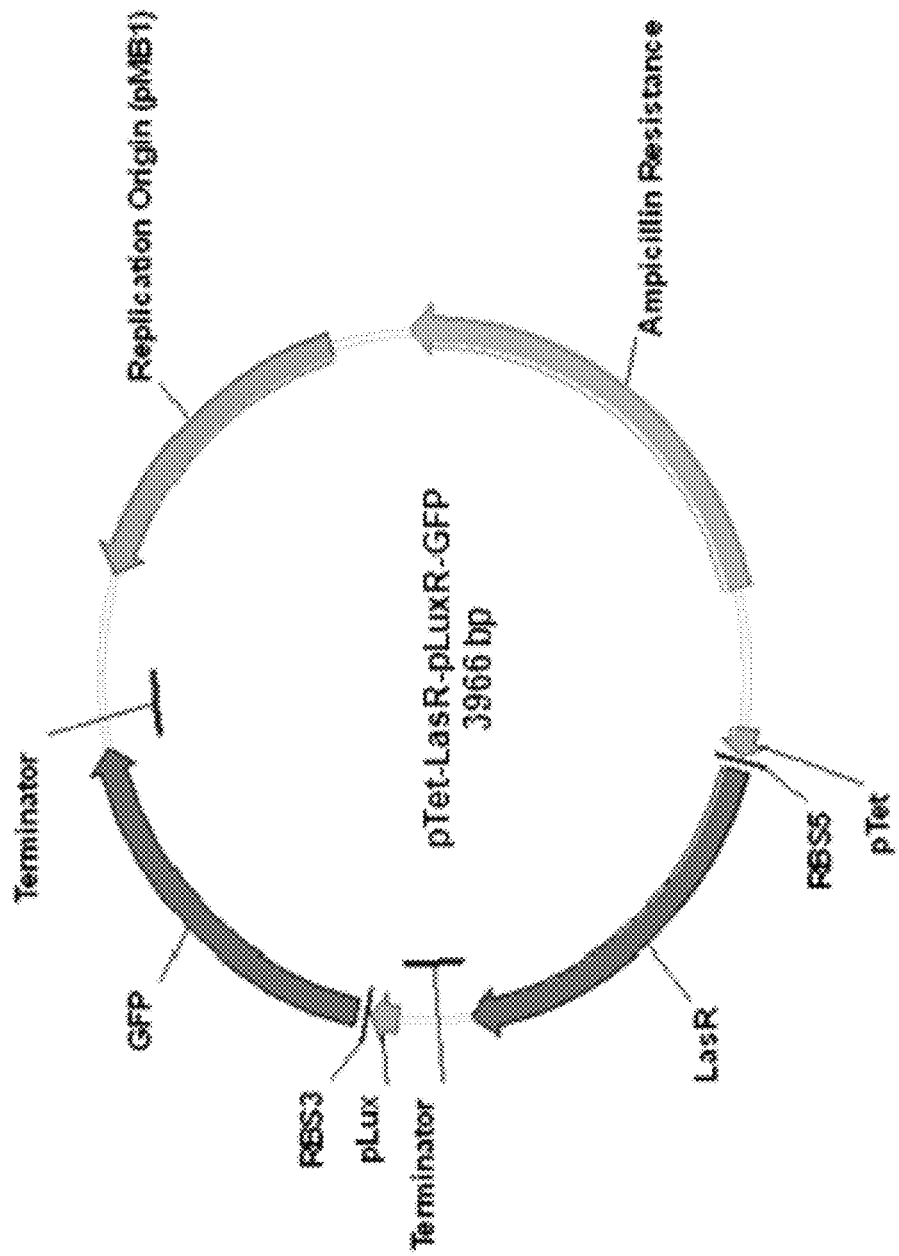

To evaluate and characterize the sensing device, the gene encoding the green fluorescent protein (GFP) was fused to the sensing device (i.e., pTetR-LasR-pLuxR-GFP; the plasmid map is shown in FIG. 7B) and the GFP expression was monitored at a range of concentrations of $3OC_{12}HSL$. From the measured GFP synthesis rates (FIG. 2A), a basal expression level of 0.216 RFU per OD per minute without induction, followed by a sharp increase in GFP production rate as the concentration of $3OC_{12}HSL$ was increased beyond 1.0E-7M was observed. This transition peaked at 1.0E-6M of $3OC_{12}HSL$ and exhibited a sharp decline afterward. The optimal detection range of the sensing device was between 1.0E-7 and 1.0E-6M $3OC_{12}HSL$. As a comparison, it has been estimated in the art extracellular concentration of $3OC_{12}HSL$ to be in the range of 1.0E-6 to 1.0E-4M within proximity to the site of *P. aeruginosa* infection.

Example 9

Transfer Function of the Sensing Device

Figure 2B:
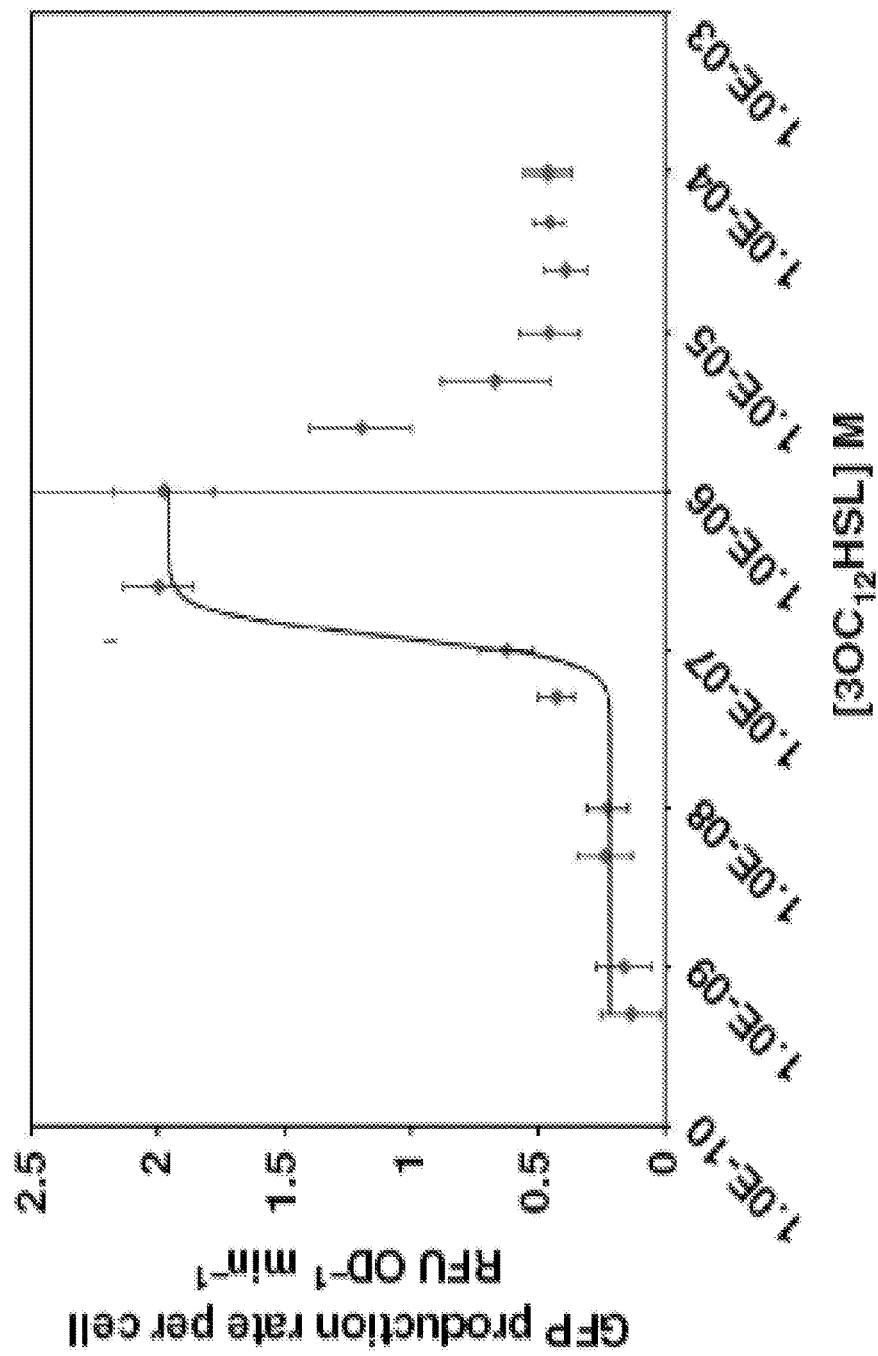

One important characteristic of the sensing device was the transfer function that describes the static relationship between the input ($3OC_{12}HSL$) and output (GFP production rate) of the sensing device. The transfer function was determined by fitting an empirical mathematical model (Hill equation) to the experimental data where the input $3OC_{12}HSL$ concentration is <1.0E-6M. The best fit model demonstrated that the static performance of the sensing device follows a Hill equation below the input concentration of 1.0E-6M $3OC_{12}HSL$ (FIG. 2B). The model showed that the sensing device saturated at a maximum output of 1.96 RFU per OD per minute at input concentration >3.3E-7M but <1.0E-6M $3OC_{12}HSL$, and the switch point for the sensing device was 1.2E-7M $3OC_{12}HSL$, the input concentration at which output is at half-maximal. Since this switch point concentration is smaller than the concentration of $3OC_{12}HSL$ present (1.0E-6 to 1.0E-4M) within proximity to the site of *P. aeruginosa* infection, the sensing device would be sensitive enough to detect the amount of $3OC_{12}HSL$ natively produced by *P. aeruginosa*.

Example 10

Detection of the Native Autoinducer Produced by *P. Aeruginosa*

The characterization of the sensing device as described herein above indicated that it produced an optimal output at 1.0E-7 to 1.0E-6M $3OC_{12}HSL$. To verify that the sensing device would be able to sense the amount of $3OC_{12}HSL$ natively produced by *P. aeruginosa*, the sensing device coupled with a GFP reporter (i.e., pTetR-LasR-pLuxR-GFP) was induced using the filtered culture of *P. aeruginosa* ln 7, a clinical isolate that is sensitive to pyocin S5. Measurements show that GFP synthesis rate for the isolate ln 7 was 1.375 RFU per OD per minute. This value was above the minimum synthesis rate and greater than the half-maximal of the sensing device. This confirmed that the sensing device was able to detect the natively produced $3OC_{12}HSL$. Further, the GFP synthesis rate measured and the model (Equation (1)) was used to gain an insight into the amount of $3OC_{12}HSL$ natively produced by the isolate. The average concentration of $3OC_{12}HSL$ in the liquid culture of the *P. aeruginosa* strain was estimated to be ~1.0E-6M $3OC_{12}HSL$. This measurement was coherent with the extracellular concentration of $3OC_{12}HSL$ estimated in the art which is between 1.0E-6 and 1.0E-4M.

Example 11

Characterization of the Lysing Device

Figure 1B:
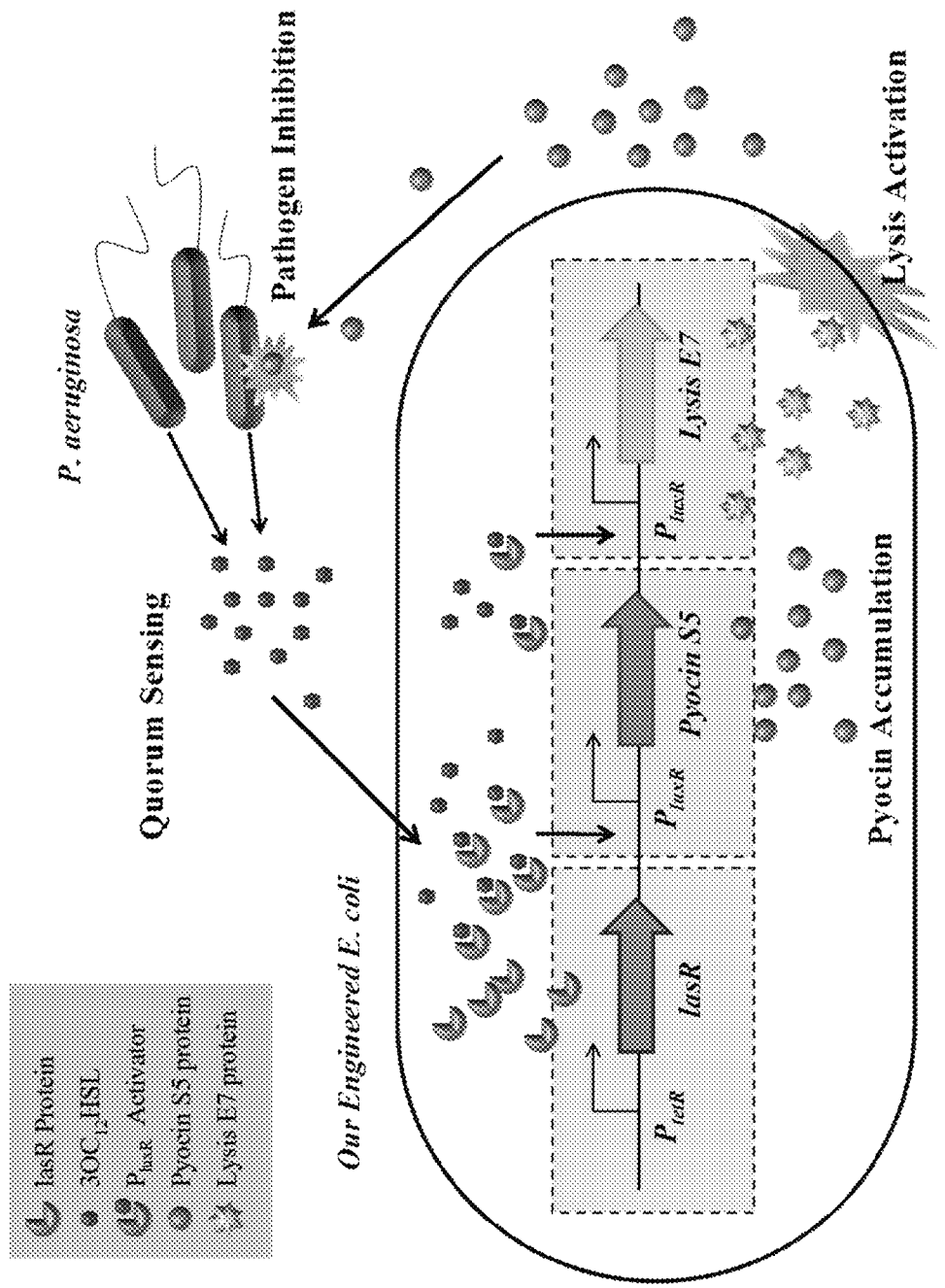
Figure 3A:
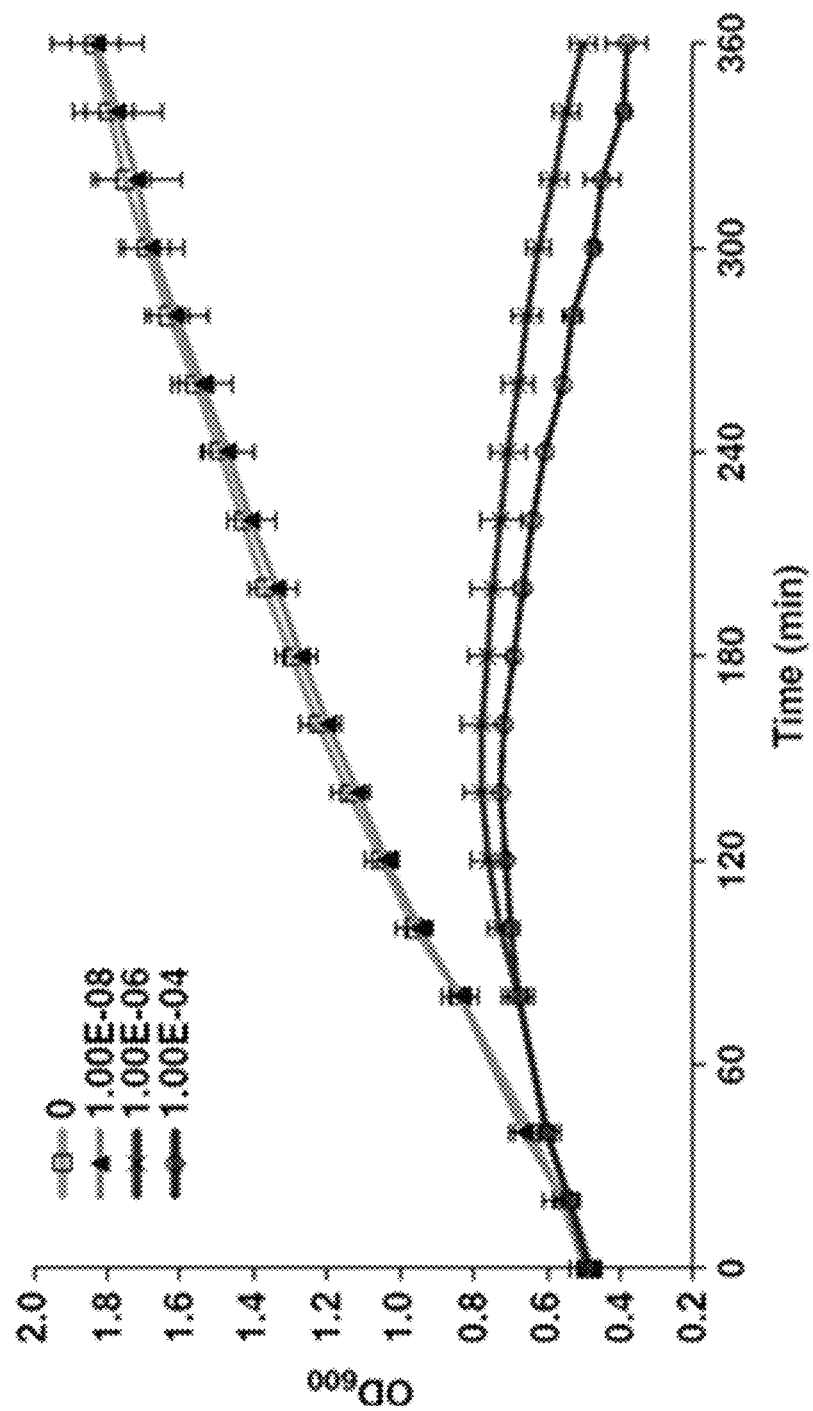
FIGS. 3A-3C show the characterization of a lysis device using $3OC_{12}HSL$.
Figure 3B:
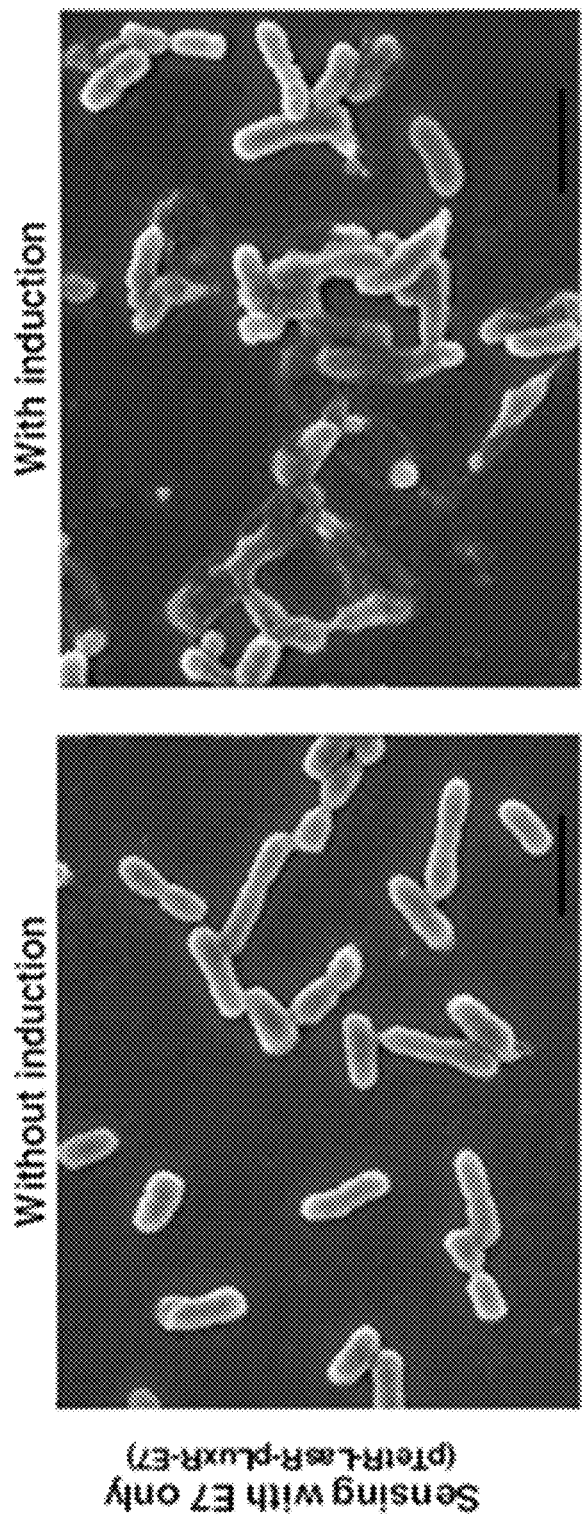
Figure 7C:
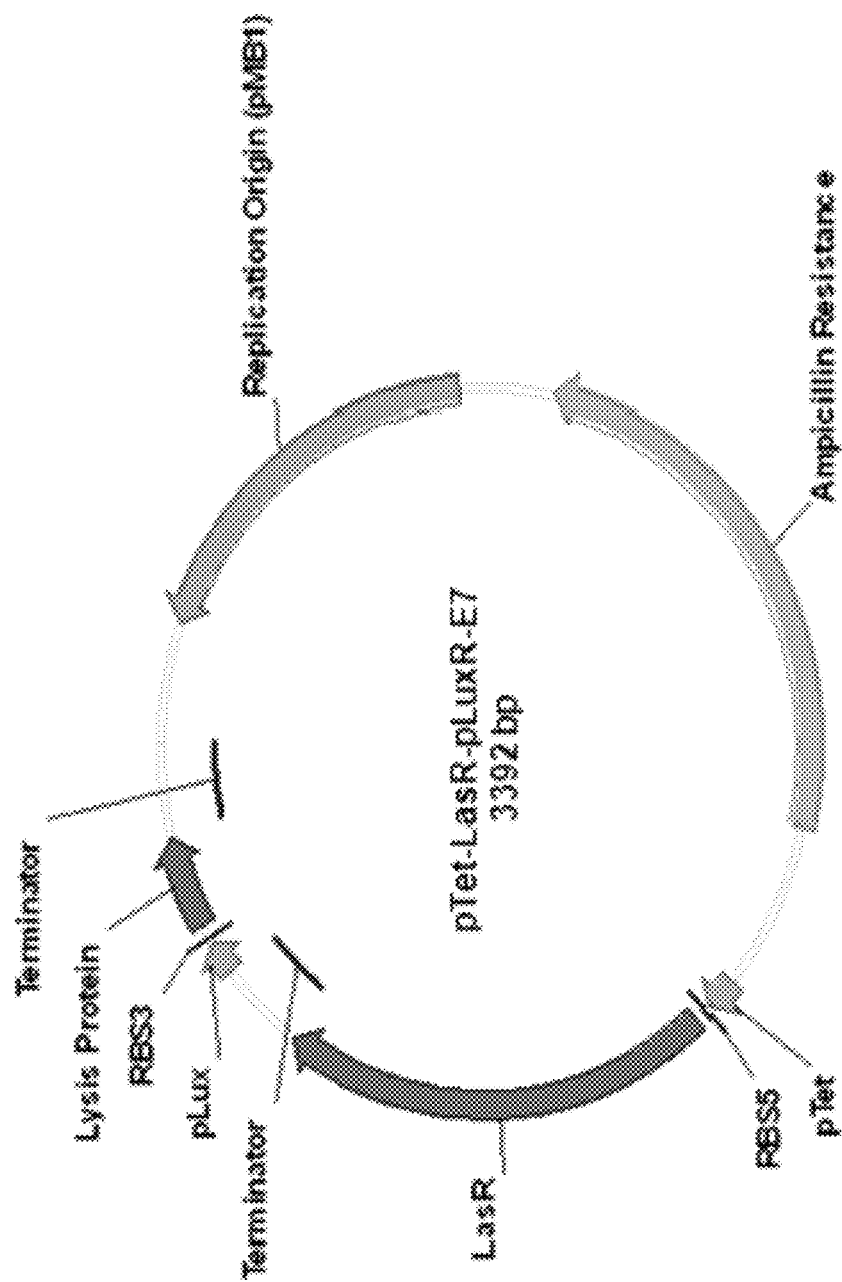

The system according to various embodiments was designed to release pyocin S5 through lysis upon detection of *P. aeruginosa*. To determine the lysis activity of the system, the behavior of the E7 lysis protein under the transcriptional control of the sensing device before integrating both the pyocin S5 and E7 genes into the system was characterized. The E7 lysis gene was ligated downstream to the sensing device (i.e., pTetR-LasR-pLuxR-E7; the plasmid map is shown in FIG. 7C) and its performance was evaluated in the *E. coli* chassis over time by measuring absorbance at $OD_{600}$ at a range of concentrations of $3OC_{12}HSL$. FIG. 3A shows that at 0 and 1.0E-8M $3OC_{12}HSL$, the growth rates of *E. coli* underwent no noticeable transition into a lysis state. However, at higher concentrations of $3OC_{12}HSL$ (i.e., 1.0E-6 and 1.0E-4M), the cells exhibited a significant reduction in optical density, likely due to the lysis activity. In this example, it is implied that 1.0E-6M or higher concentrations of $3OC_{12}HSL$ cause observable cell lysis with a delay of ~120 mins. To verify the effect of the lysis, cell integrity was examined with and without 1.0E-6M $3OC_{12}HSL$ using field emission scanning electron microscopy (FESEM). FIG. 3B shows that *E. coli* containing pTetR-LasR-pLuxR-E7 and induced with $3OC_{12}HSL$ appeared shriveled with corrugated surface morphology, in contrast to the distinct 'rod-like' features of the cells that were not induced with $3OC_{12}HSL$. To further confirm that the lysis activity may be sustained in the final system including pyocin S5, the morphology of *E. coli* containing the final system (i.e., pTetR-LasR-pLuxR-S5-pLuxR-E7; FIG. 1B) was monitored using FESEM.

Figure 3C:
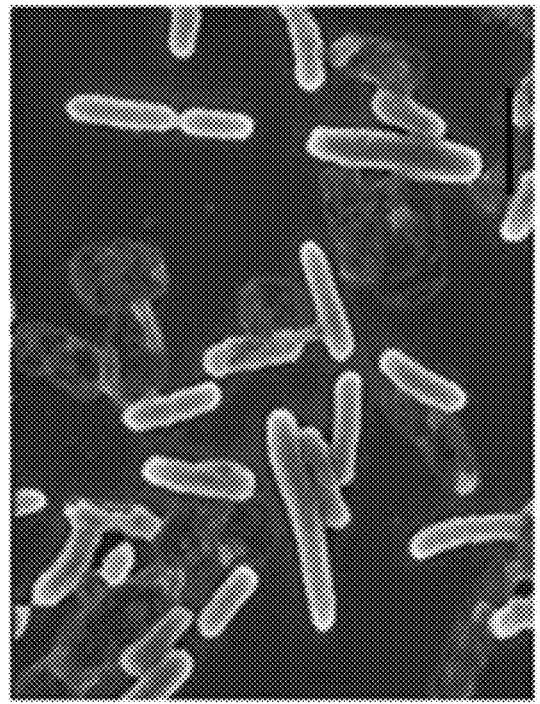
Figure 3C:
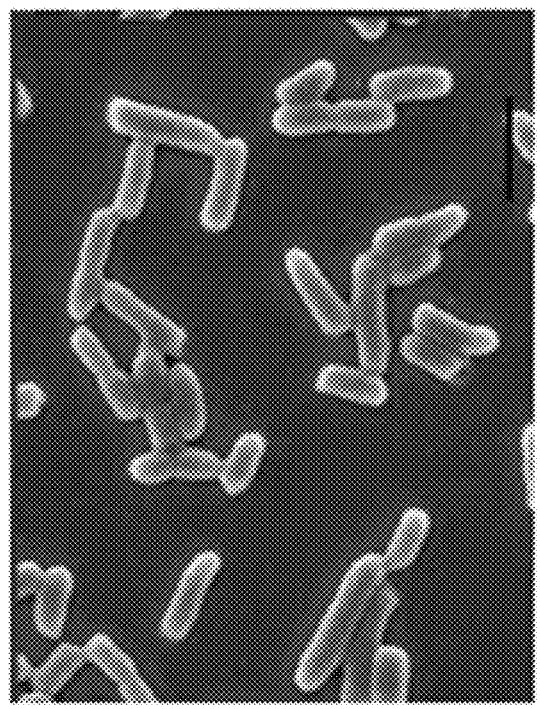

FIG. 3C shows that *E. coli* cells having the final system and induced with $3OC_{12}HSL$ also appeared shriveled with corrugated surface morphology, whereas *E. coli* cells having the final system but not induced with $3OC_{12}HSL$ remained 'rod-like' in shape. These observations were similar to that obtained in earlier examples with *E. coli* containing pTetR-LasR-pLuxR-E7. This suggests that $3OC_{12}HSL$ induced the lysis of the *E. coli* containing the final system.

Figure 4A:
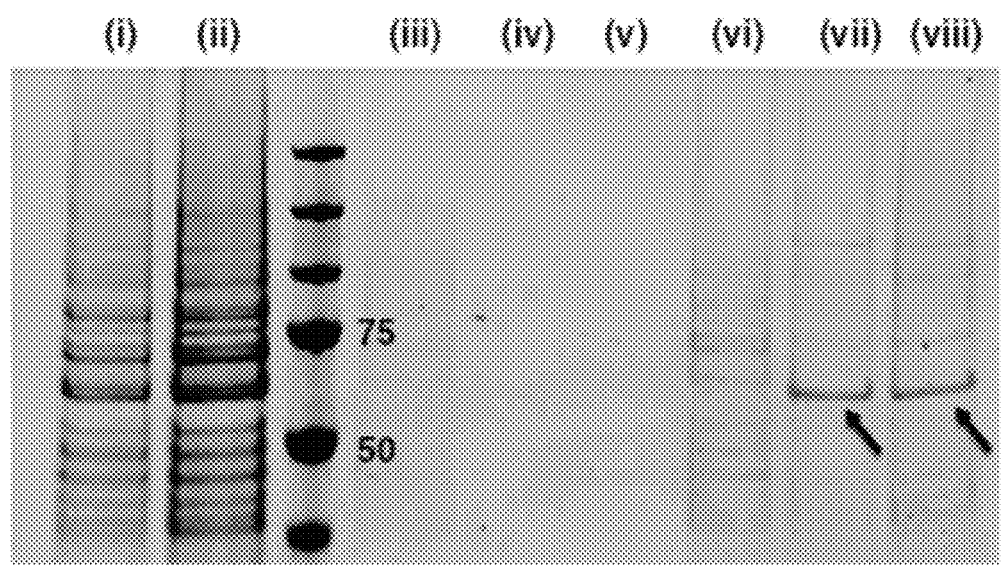
FIGS. 4A and 4B show the characterization of the lysis device in the final system using $3OC_{12}HSL$.
Figure 4B:
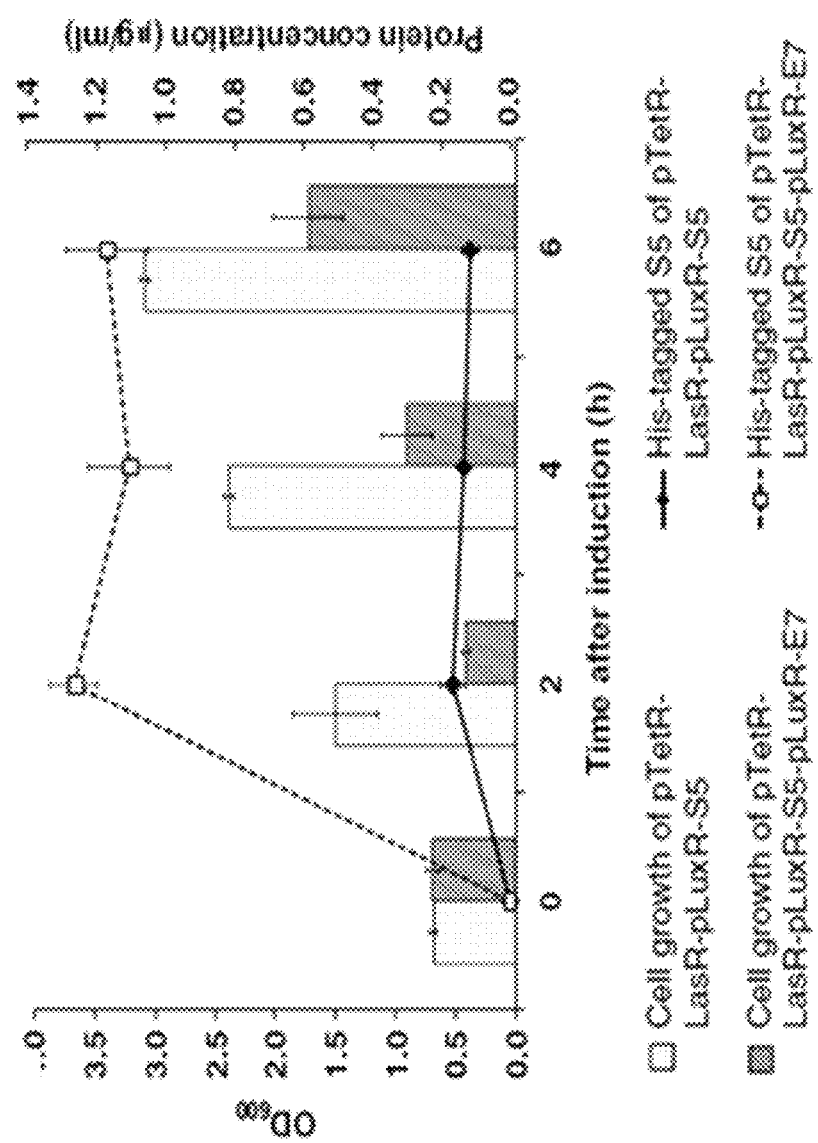
Figure 7D:
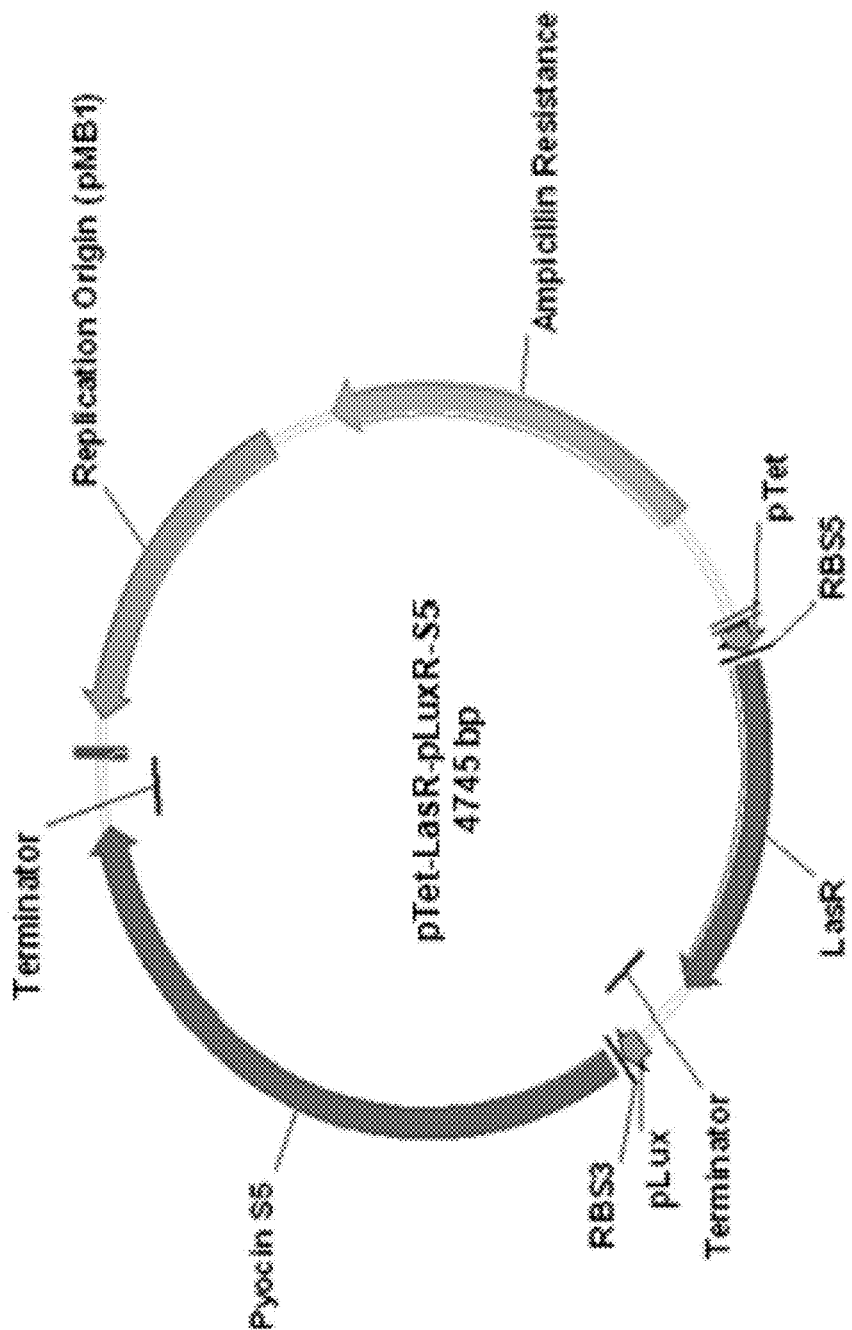

In line with the overall objective of the E7 lysis device in mediating the export of pyocin, the efficiency of the lysis device in the final system by measuring the amount of the released protein was studied. After induction with 1.0E-6M $3OC_{12}HSL$, histidine-tagged S5 protein was purified by immobilized metal affinity chromatography from the filtered supernatant and analyzed by SDS-PAGE and Bradford assay. FIG. 4A shows that distinct bands that corresponded to pyocin S5 were observed on the SDS-PAGE of the final system (i.e., pTetRLasR-pLuxR-S5-pLuxR-E7), while no bands were seen in lanes without the lysis device (i.e., pTetR-LasR-pLuxR-S5; the plasmid map is shown in FIG. 7D). The observations were validated by estimating the protein concentrations in the supernatant with Bradford assay and showed that the amount of pyocin released by the final system was eight times higher than the system without the lysis device (FIG. 4B). The dynamic performance of the lysis device in the final system was characterized by an impulse release of protein 2 hrs after induction, followed by a steady-state response.

Example 12

Verification of the Final System with the Sensing, Killing, and Lysing Devices

The engineered microbes according to various embodiments are able to sense natively produced AHL $3OC_{12}HSL$, which subsequently triggers cell lysis. To further determine whether the sensing of $3OC_{12}HSL$ also leads to the killing of P. aeruginosa designed, the growth of P. aeruginosa was monitored in the presence of the engineered E. coli containing the final system.

Figure 8A:
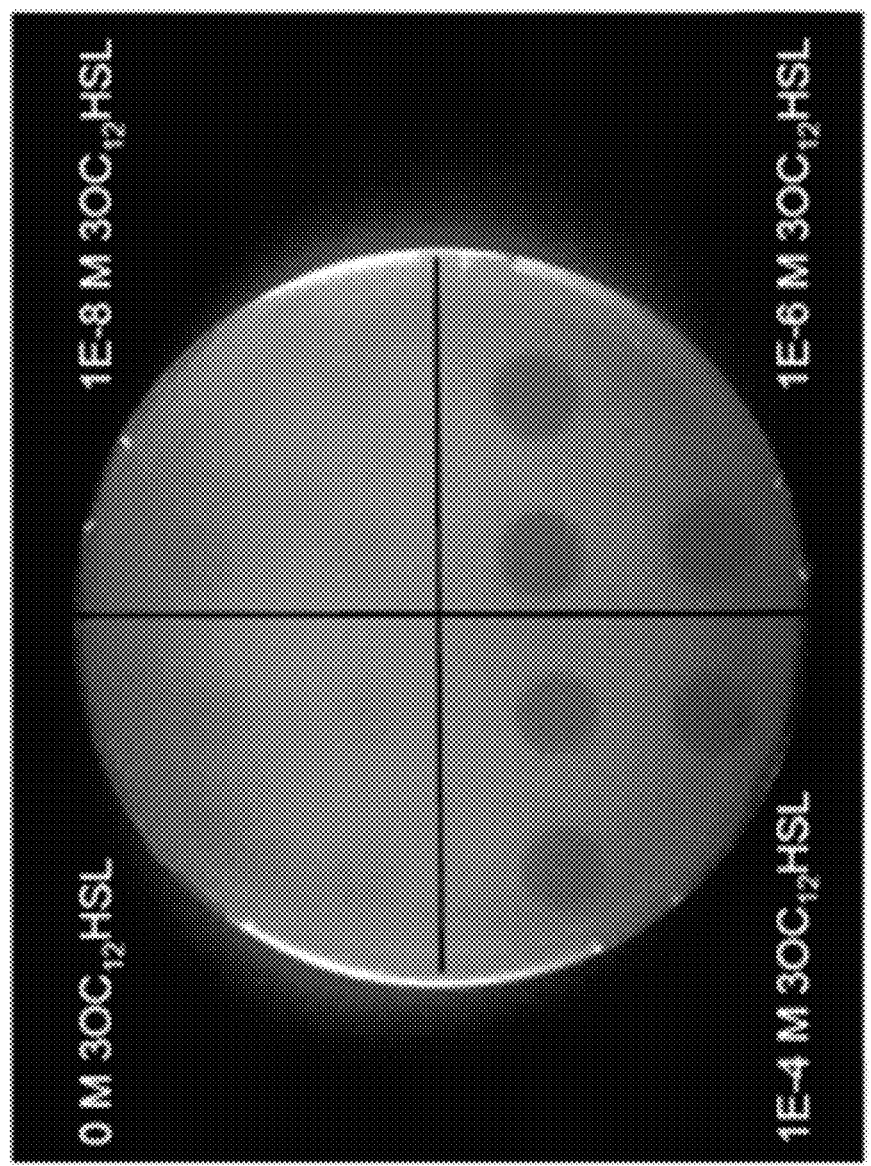
FIGS. 8A-8C show inhibition of *P. aeruginosa* by the engineered *E. coli* induced with $3OC_{12}HSL$.

First, to determine the concentration of $3OC_{12}HSL$ that causes a significant growth inhibition and confirm that the concentration falls within the range of concentrations of $3OC_{12}HSL$ naturally produced by P. aeruginosa, the engineered E. coli was exposed to commercial $3OC_{12}HSL$ at 0, 1.0E-8, 1.0E-6, and 1.0E-4M, and the filtered supernatants were added onto P. aeruginosa-grown agars. The growth of P. aeruginosa was clearly inhibited by the filtered supernatants of the E. coli cultures exposed to 1.0E-6 and 1.0E-4M $3OC_{12}HSL$, whereas very faint inhibition zones were observed at 0 and 1.0E-8M, likely due to the basal expression of pyocin S5 and E7 (FIG. 8A).

Figure 8B:
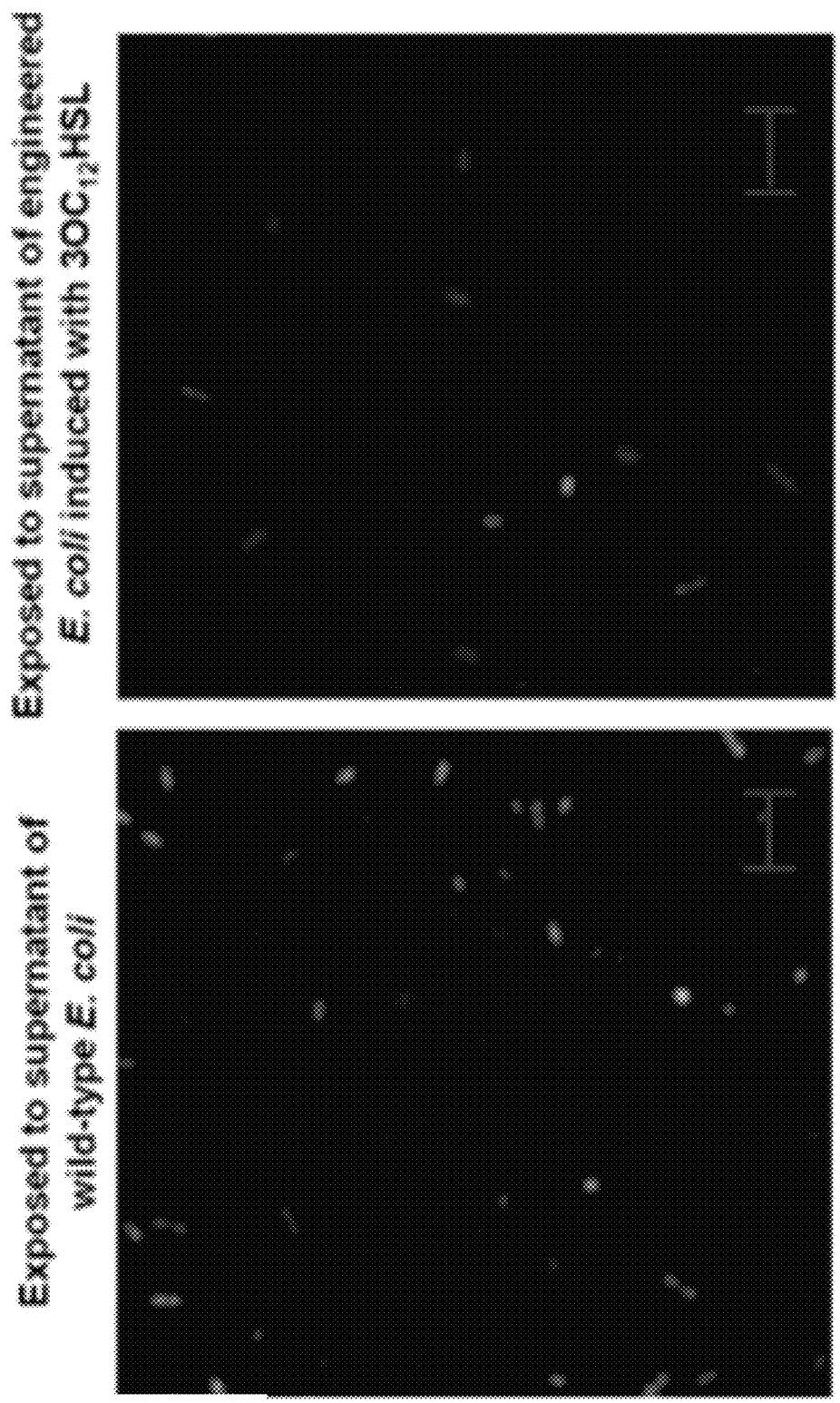

Second, to further confirm the inhibition effects, P. aeruginosa was examined upon exposure to the supernatant of the E. coli cultures with 1.0E-6M $3OC_{12}HSL$ using the LIVE/DEAD cell viability assay. As seen under microscope, many P. aeruginosa cells exposed to the supernatant of the engineered E. coli were stained with the PI dye, which stains a dead cell, whereas those that were incubated with the wild-type E. coli were mostly stained with the SYTO 9 dye, which stains a live cell (FIG. 8B). This suggests that the engineered E. coli in accordance to various embodiments carrying the final system can kill P. aeruginosa in response to as low as 1.0E-6M $3OC_{12}HSL$. Since earlier estimation indicated that the concentration of $3OC_{12}HSL$ natively produced by P. aeruginosa was ~1.0E-6M, this outcome may imply that this killing activity would be sustained against P. aeruginosa in response to its producing $3OC_{12}HSL$.

Figure 5A:
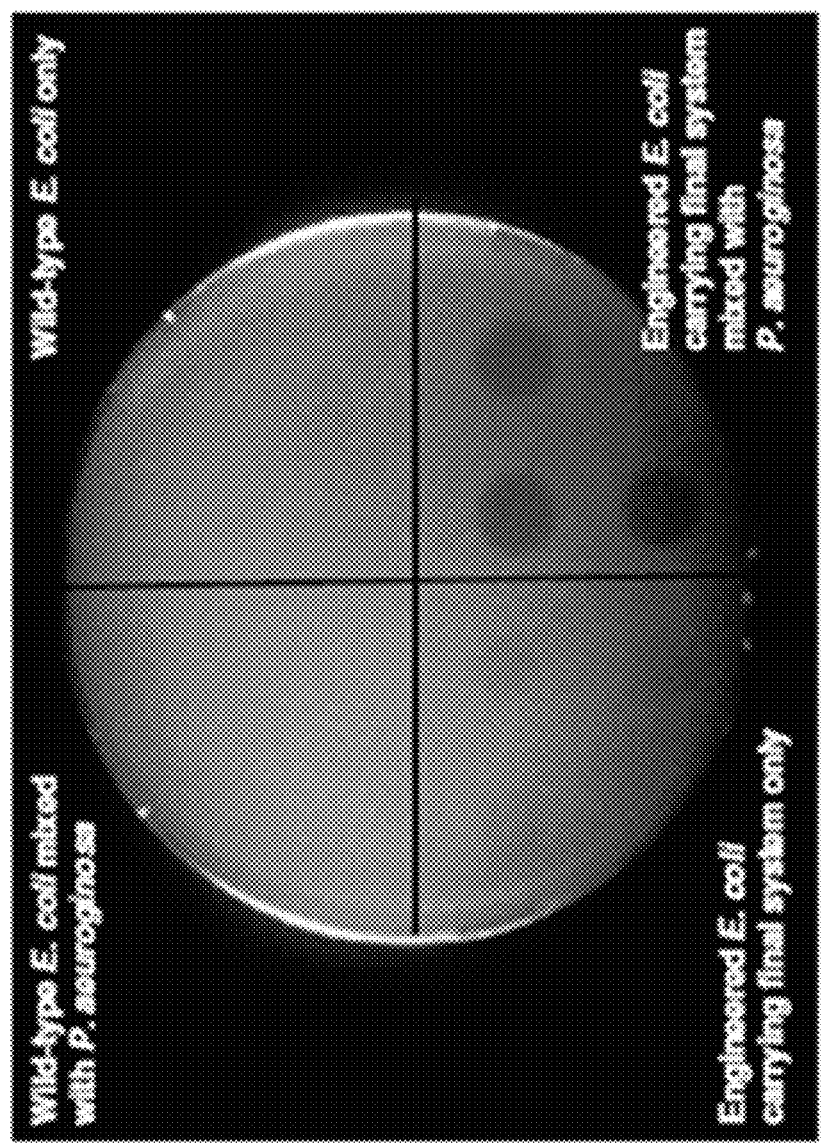
FIGS. 5A-5D show the inhibition of *P. aeruginosa* by the engineered *E. coli* induced with native $3OC_{12}HSL$ produced by *P. aeruginosa*.

Therefore, subsequently, to confirm the killing activity by the native $3OC_{12}HSL$ produced by P. aeruginosa, the filtered supernatant of P. aeruginosa cultures was mixed with the E. coli cultures, whose supernatant was then added to P. aeruginosa-grown agars. FIG. 5A shows that P. aeruginosa growth was significantly inhibited by the engineered E. coli cultures exposed to the supernatant of P. aerusinosa cultures, while neither with the wild-type E. coli cells nor without the P. aerusinosa supernatant led to growth inhibition. This indicates that the final system produces pyocin S5 and E7 in response to the $3OC_{12}HSL$ natively produced by P. aerusinosa, which resulted in the killing of P. aeruginosa.

Figure 5B:
Figure 5B:

To further visualize the inhibition effects on P. aerusinosa by the engineered E. coli in accordance to various embodiments, P. aerusinosa cells were stained using the LIVE/DEAD cell viability assay. FIG. 5B shows that many P. aerusinosa cells exposed to the supernatant of the engineered E. coli induced with native $3OC_{12}HSL$ were stained with the PI dye, whereas the cells incubated with the wild-type E. coli were mostly stained with the SYTO 9 dye (green). This suggests that the engineered E. coli in accordance to various embodiments carrying the final system can kill P. aerusinosa in the presence of native $3OC_{12}HSL$ produced by P. aeruginosa.

To verify that the engineered E. coli that contains the final system in accordance to various embodiments (e.g., pTetR-LasR-pLuxR-S5-pLuxR-E7) exerts a killing activity against P. aerusinosa in a mixed culture, the growth of P. aerusinosa co-cultured with the engineered E. coli in the ratio 1:4 was monitored.

Figure 5C:
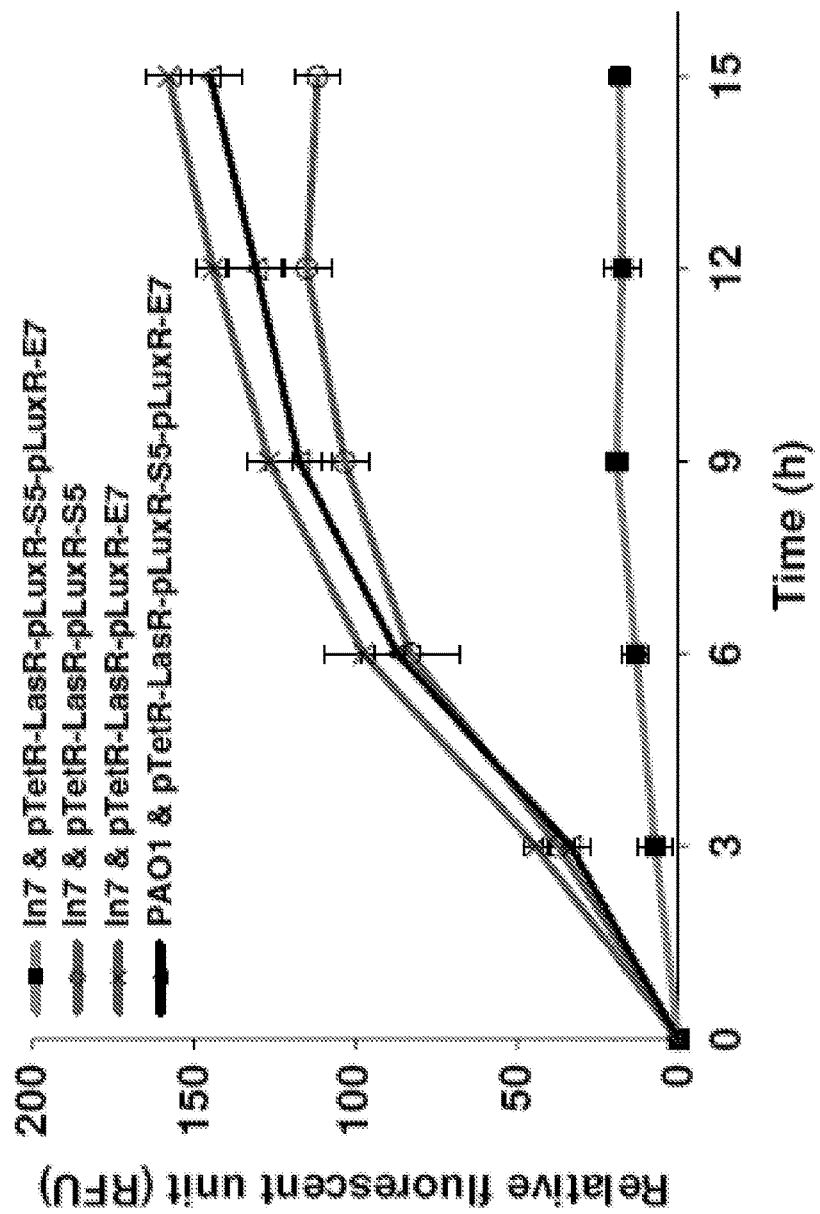

To determine the growth inhibition of P. aerusinosa in the mixed culture, P. aeruginosa that constitutively expresses GFP and E. coli that is without either the pyocin S5 or E7 lysis devices as negative controls was used. FIG. 5C shows that the GFP expression level of the P. aerusinosa co-cultured with the E. coli that carries the final system remained low and almost constant, whereas the GFP level underwent an exponentially increase when P. aerusinosa was cultured with the negative control E. coli systems.

Figure 5D:
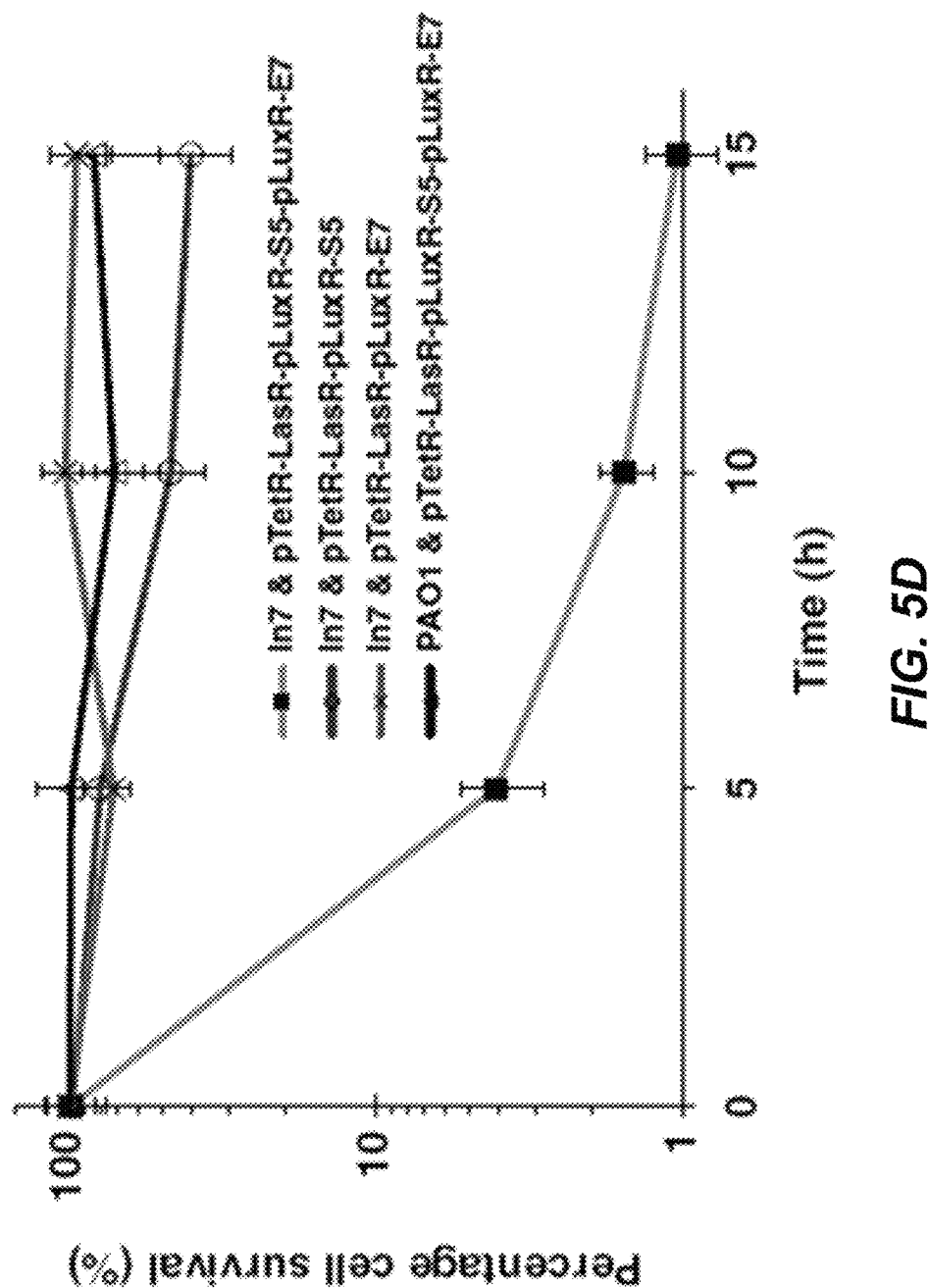

To verify the efficiency in growth inhibition, CFU count on mixed cultures using P. aerusinosa that was transformed with chloramphenicol-resistant plasmid was performed. FIG. 5D shows that the engineered E. coli inhibited the growth of P. aeruginosa by >99% while continuous growths were apparent in P. aerusinosa co-cultured with incomplete E. coli systems missing either the pyocin S5 or E7 lysis devices.

Figure 8C:
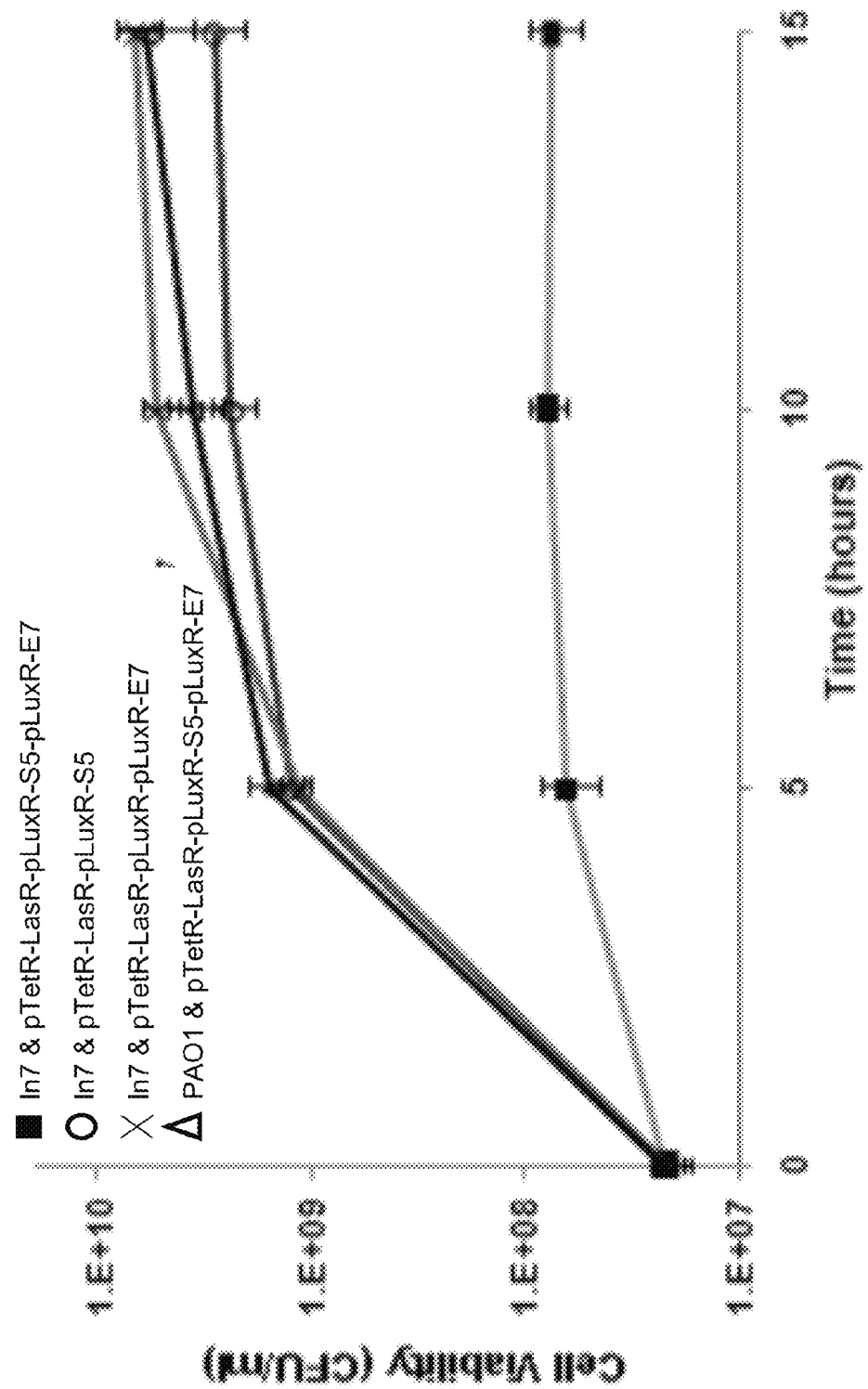
Figure 9A:
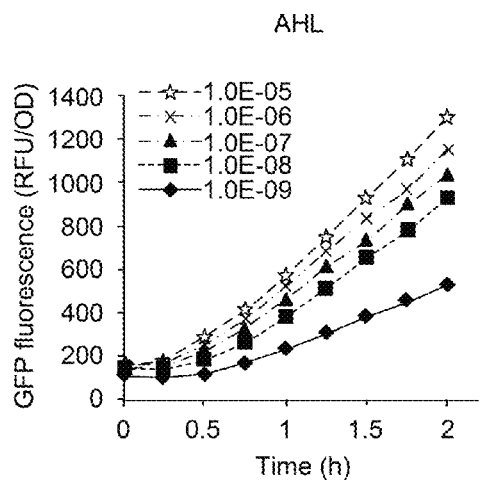
FIGS. 9A-9D: Testing the improved quorum sensing (QS) device against natively expressed quorum sensing molecules from *P. aeruginosa*. *E. coli* transformed with pE8k-pLasI-GFP was co-cultured with (a) AHL (b) culture supernatant of *P. aeruginosa* cells (OD 1.0) (c) or mature biofilm of *P. aeruginosa*, and assayed for GFP expression. (d) GFP expression in response to 1000-fold diluted supernatant (OD 1.0) is equivalent to ~10-8M AHL.
Figure 9B:
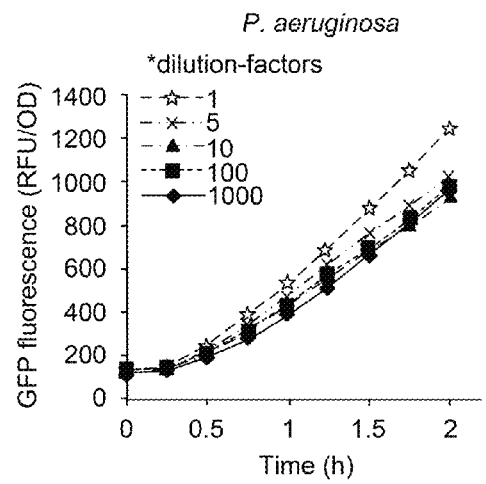
Figure 9C:
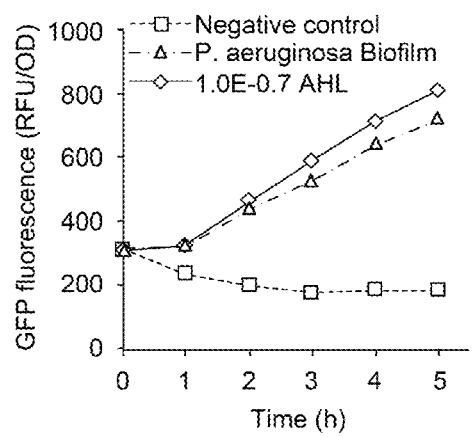
Figure 9D:
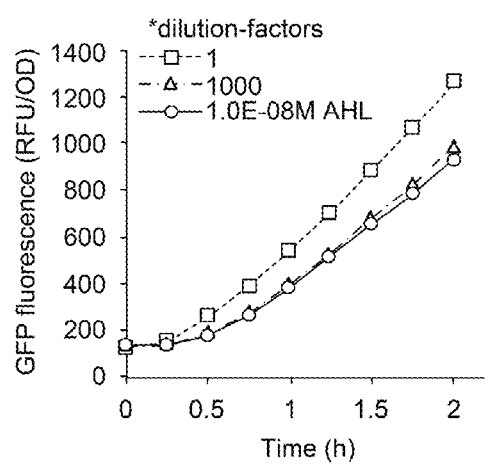

The example also implies that the engineered system in accordance to various embodiments was activated only after the pathogen entered the late exponential and stationary phase when the autoinducers were released (FIG. 8C).

Figure 6A:
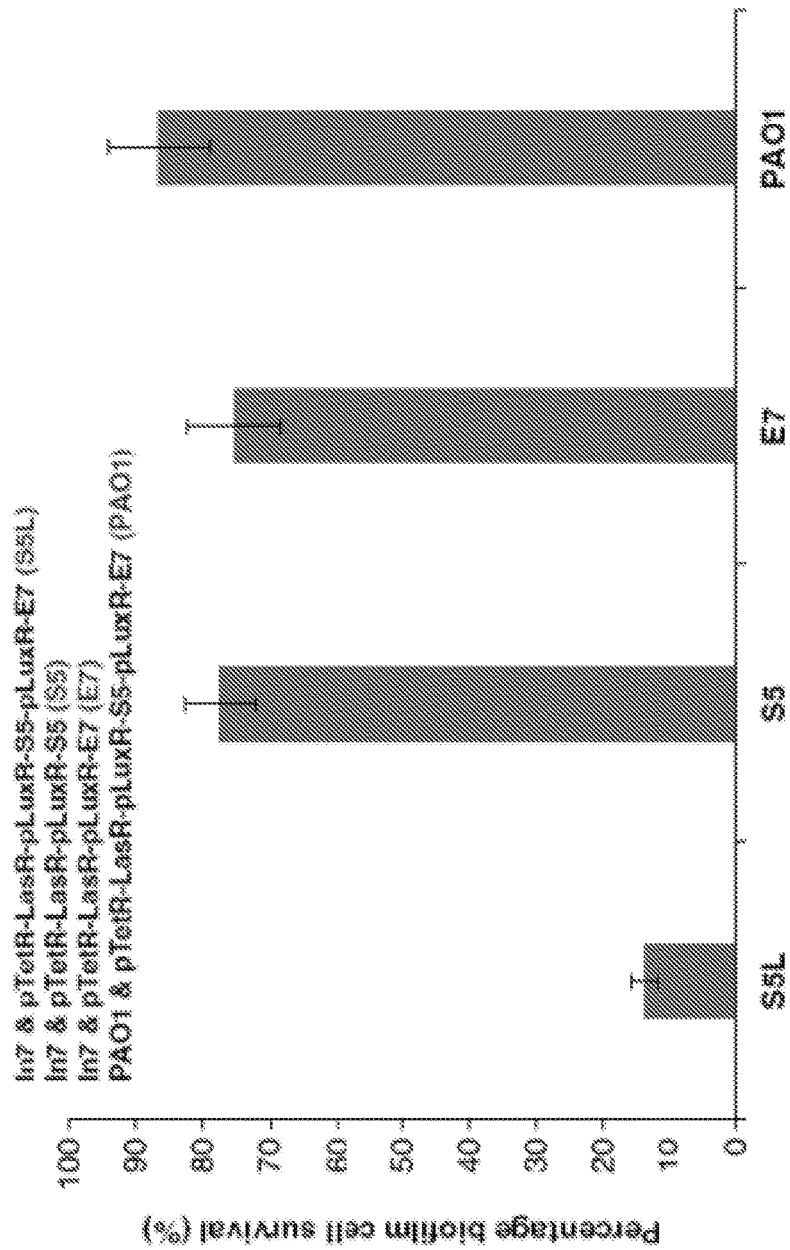
FIGS. 6A and 6B show biofilm inhibition assay with engineered *E. coli*.

To examine the potential application of the engineered system in accordance to various embodiments against a pseudo disease state of Pseudomonas, a static biofilm inhibition assay was performed by culturing P. aerusinosa carrying a chloramphenicol-resistance plasmid with the engineered E. coli. FIG. 6A shows that the engineered E. coli inhibited the formation of P. aeruginosa biofilm by close to 90%. This observation is in stark contrast to the pyocin-resistant control strain PAO1 and pyocin-sensitive clinical isolate ln 7 subjected to treatment with E. coli having the systems missing either the pyocin S5 or E7 lysis gene.

Figure 6B:
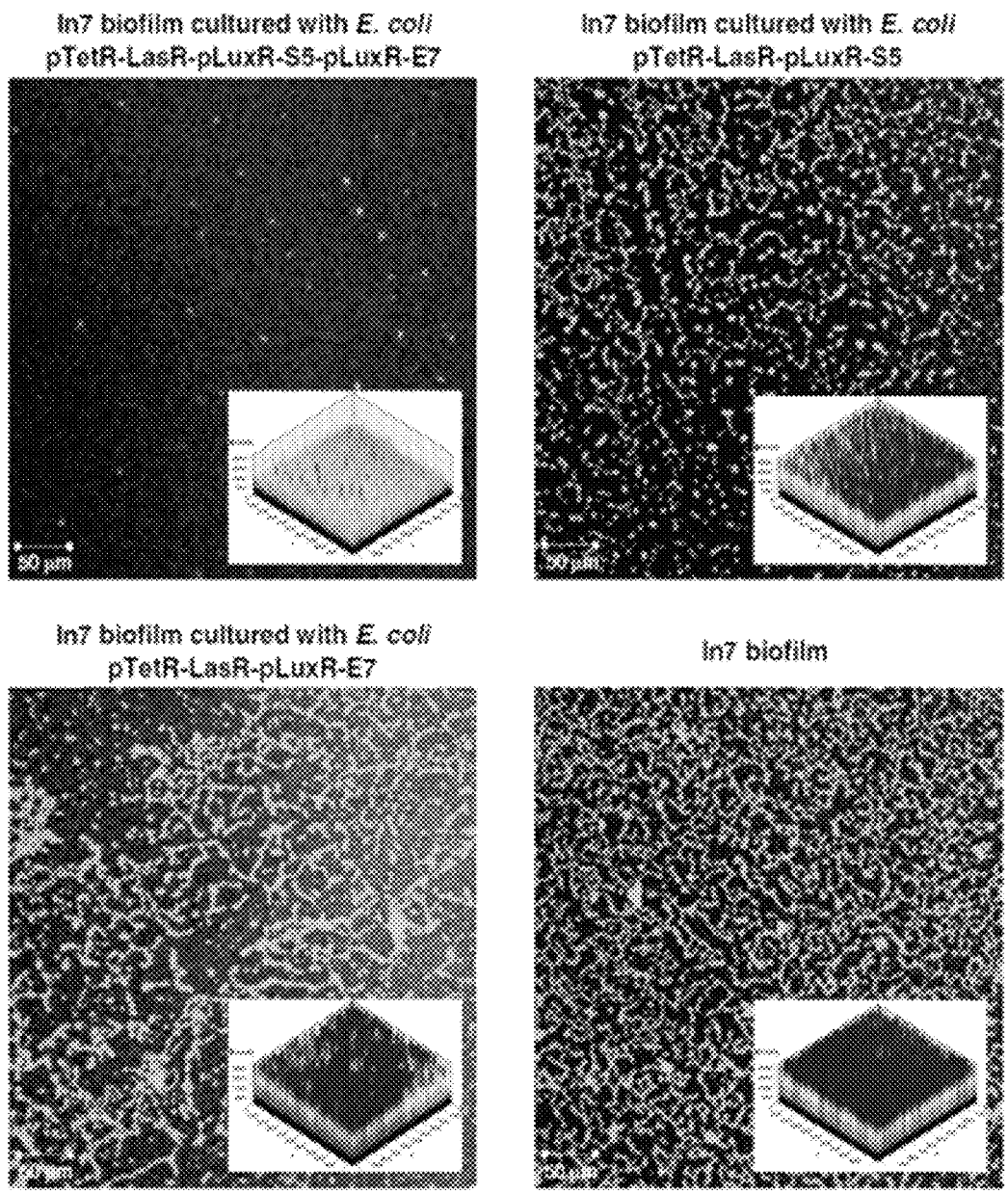

To visualize the extent of biofilm inhibition, biofilm cells with green fluorescence were grown in the presence of engineered E. coli on glass slide substrate and examined with confocal laser scanning microscopy (CLSM). FIG. 6B shows that the morphology of Pseudomonas biofilm treated with the engineered E. coli appeared sparse while elaborated honeycombed structures were apparent in the control examples. This observation implies that the engineered E. coli in accordance to various embodiments has the capability to inhibit biofilm formation during the initial attachment phase and prevent subsequent progression into mature microcolonies. Collectively, the examples suggest that the engineered E. coli carrying the final system, which contains the sensing, killing, and lysing devices, can effectively inhibit the growth of P. aerusinosa in both planktonic and sessile states, e.g. biofilm states when those two microbes were grown together.

*E. coli*, a natural inhabitant of the gastrointestinal tract, was chosen as the chassis in this example. It should be understood that the synthetic biology framework and genetic devices developed could potentially be transferred into other microbial chassis such as probiotics and residential microbes of the upper respiratory tract. Further, the possibility of engineering potentially beneficial microbiota into therapeutic bioagents to arrest *Pseudomonas* infection should be appreciated.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. An isolated nucleic acid molecule comprising:
  (a) a first nucleotide sequence encoding a protein that is able to form a complex with a quorum sensing molecule produced by a pathogenic microorganism;
  (b) one or more second nucleotide sequences, wherein the one or more second nucleotide sequences are under the control of a first inducible promoter that is induced by the complex of the protein encoded by the first nucleotide sequence and the quorum sensing molecule produced by the pathogenic microorganism and encoding
    (i) an antimicrobial peptide, wherein the antimicrobial peptide is effective against the pathogenic microorganism; and/or
    (ii) an antibiofilm enzyme, wherein the antibiofilm enzyme is effective against the pathogenic microorganism; and
  (c) a third nucleotide sequence under the control of a second inducible promoter, wherein the third nucleotide sequence encodes a protein that controls the motility of the host organism and directs the motility of the host organism towards the pathogenic microorganism; wherein the quorum sensing molecule is an acyl homoserine lactone (AHL), wherein the protein encoded by the first nucleotide sequence is a transcription factor, wherein the antimicrobial protein encoded by the second nucleotide sequence is a bacteriocin, and wherein the antibiofilm enzyme encoded by the second nucleotide sequence is a nuclease.

2. The isolated nucleic acid molecule of claim 1, wherein the first nucleotide sequence is under control of a constitutively active promoter.

3. The isolated nucleic acid molecule of claim 1, wherein the AHL comprises N-3-oxododecanoyl homoserine lactone ($3OC_{12}HSL$).

4. The isolated nucleic acid molecule of claim 1, wherein the protein encoded by the first nucleotide sequence is the transcription factor LasR and the quorum sensing molecule is AHL N-3-oxododecanoyl homoserine lactone ($3OC_{12}HSL$).

5. The isolated nucleic acid molecule of claim 1, wherein the first and second inducible promoter of the one or more second nucleotide sequences and the third nucleotide sequence is a luxR or pLasI promoter that is inducible by a complex of LasR and $3OC_{12}HSL$.

6. The isolated nucleic acid molecule of claim 1, wherein the bacteriocin is a microcin S.

7. The isolated nucleic acid molecule of claim 1, wherein the nuclease is DNaseI.

8. The isolated nucleic acid molecule of claim 1, wherein the antimicrobial peptide, the antibiofilm enzyme or both are fused to a secretion tag.

9. The isolated nucleic acid molecule of claim 8, wherein the secretion tag is YebF.

10. The isolated nucleic acid molecule of claim 1, wherein the protein encoded by the third nucleotide sequence comprises CheZ from *E. coli*.

11. The isolated nucleic acid molecule of claim 1, wherein the protein encoded by the third nucleotide sequence comprises a degron to decrease its stability.

12. The isolated nucleic acid molecule of claim 11, wherein the degron is SsrA or YbaQ.

13. The isolated nucleic acid molecule of claim 1, wherein the pathogenic microorganism is selected from the group consisting of *Pseudomonas aeruginosa, Clostridium difficile, Escherichia coli, Helicobacter pylori, Salmonella, Vibrio cholera* and *Yersinia*.

14. The isolated nucleic acid molecule of claim 1, wherein the first nucleotide sequence has the nucleotide sequence set forth in SEQ ID NO: 1.

15. The isolated nucleic acid molecule of claim 1, wherein the second nucleotide encoding an antimicrobial peptide sequence together with the first inducible promoter has the nucleotide sequence set forth in SEQ ID NO: 7.

16. The isolated nucleic acid molecule of claim 1, wherein the second nucleotide sequence encoding the antibiofilm enzyme together with the first inducible promoter has the nucleotide sequence set forth in SEQ ID NO: 8.

17. The isolated nucleic acid molecule of claim 1, wherein the third nucleotide sequence together with the second inducible promoter has the nucleotide sequence set forth in SEQ ID NO: 9.

18. The isolated nucleic acid molecule of claim 1 comprised in a vector.

19. A recombinant microorganism comprising the isolated nucleic acid molecule of claim 1.

20. The recombinant microorganism of claim 19, wherein the microorganism is *E. coli*.

21. A method of sensing and killing pathogenic microorganisms, the method comprising contacting a recombinant microorganism comprising the isolated nucleic acid molecule of claim 1 with the pathogenic microorganism.

22. The method of claim 21, wherein the method is a method of sensing and killing pathogenic microorganisms in a subject, the method comprising administering the recombinant microorganism to the subject.

23. The method of claim 21, wherein the pathogenic microorganism is a human pathogen.

24. The method of claim 21, wherein the pathogenic microorganism is selected from the group consisting of *Pseudomonas aeruginosa, Clostridium difficile, Escherichia coli, Helicobacter pylori, Salmonella, Vibrio cholera* and *Yersinia*.

* * * * *

SEQUENCE LISTING

```
<160> NUMBER OF SEQ ID NOS: 10

<210> SEQ ID NO 1
<211> LENGTH: 720
<212> TYPE: DNA
<213> ORGANISM: Pseudomonas aeruginosa

<400> SEQUENCE: 1
atggccttgg ttgacggttt tcttgagctg gaacgctcaa gtggaaaatt ggagtggagc      60
gccatcctcc agaagatggc gagcgacctt ggattctcga agatcctgtt cggcctgttg     120
cctaaggaca gccaggacta cgagaacgcc ttcatcgtcg caactaccc ggccgcctgg      180 cgcgagcatt acgaccgggc tggctacgcg cgggtcgacc cgacggtcag tcactgtacc     240
cagagcgtac tgccgatttt ctgggaaccg tccatctacc agacgcgaaa gcagcacgag     300
ttcttcgagg aagcctcggc cgccggcctg gtgtatgggc tgaccatgcc gctgcatggt     360
gctcgcggcg aactcggcgc gctgagcctc agcgtggaag cggaaaaccg ggccgaggcc     420
aaccgtttca tagagtcggt cctgccgacc ctgtggatgc tcaaggacta cgcactgcaa     480
agcggtgccg gactggcctt cgaacatccg gtcagcaaac cggtggttct gaccagccgg     540
gagaaggaag tgttgcagtg gtgcgccatc ggcaagacca gttgggagat atcggttatc     600
tgcaactgct cggaagccaa tgtgaacttc catatggaa atattcggcg gaagttcggt      660
gtgacctccc gccgcgtagc ggccattatg gccgttaatt tgggtcttat tactctctaa     720

<210> SEQ ID NO 2
<211> LENGTH: 1552
<212> TYPE: DNA
<213> ORGANISM: Artificial Sequence
<220> FEATURE:
<223> OTHER INFORMATION: pLuxR (Aliivibrio fischeri (Vibrio
      fischeri)) - Pyocin S5

<400> SEQUENCE: 2
acctgtagga tcgtacaggt ttacgcaaga aaatggtttg ttatagtcga ataaaatgag      60
caatgataat gaagttccgg gtagcatggt tattgttgca cagggtccgg atgatcagta     120
tgcatatgaa gttcctccga ttgatagcgc agcagttgcc ggtaatatgt ttggtgatct     180
gattcagcgc gaaatttatc tgcagaaaaa tatttattat ccggtgcgca gcattttga    240 acagggcacc aaagaaaaaa aagaaattaa taaaaagtg agcgatcagg ttgatggtct     300
gctgaaacaa attacccagg gtaaacgtga agcaacccgt caagaacgtg ttgatgttat     360
gagcgcagtg ctgcataaaa tggaaagcga tctggaaggc tataaaaaaa cctttacgaa     420
aggtccgttt attgattatg aaaaacagag cagcctgagc atttatgaag cctgggtgaa     480
aatttgggaa aaaaatagct gggaagaacg taaaaaatat ccgtttcagc agctggttcg     540
cgatgaactg gaacgtgcag tggcatatta taaacaggat agcctgagcg aagcagttaa     600
agttctgcgt caggaactga ataaacagaa agccctgaaa gaaaaagaag atctgagcca     660
```

```
actggaacgc gattatcgta cccgtaaagc caatctggaa atgaaagttc agagcgaact    720
ggatcaggca ggctctgcac tgcctccgct ggttagcccg acaccggaac agtggctgga    780
acgcgcaacc cgtctggtta cccaggcaat tgcagataaa aaacagctgc agaccaccaa    840 taatacctg attaaaaatt ctccgacacc gctggaaaaa cagaaagcga tttataatgg    900
tgaactgctg gttgatgaaa tcgcatcact gcaggcacgt ctggttaaac tgaatgcaga    960
aaccacccgt cgtcgtaccg aagcagaacg taaagcagca aagaacagg cactgcagga   1020 tgcaattaaa ttcaccgcag attttttataa agaagtgacc gaaaaatttg gtgcacgtac   1080
cagcgaaatg gcacgtcagc tggcagaagg tgcacgcgt aaaatattc gtagcagcgc   1140 agaagcaatt aaatcttttg aaaaacataa agatgccctg aataaaaaac tgagcctgaa   1200
agatcgtcag gcaattgcca aagcatttga ttccctggat aaacaaatga tggcaaaaag   1260
cctggaaaaa tttagcaaag gttttggtgt tgtgggtaaa gcaattgatg cagcaagcct   1320
gtatcaggaa tttaaaatta gcaccgaaac aggcgattgg aaaccgtttt ttgtgaaaat   1380
tgaaaccctg gcagccggtg cagcagcaag ctggctggtt ggtattgcat ttgcaaccgc   1440
aaccgccacc ccgattggta ttctgggttt tgcactggtt atggcagtta ccggtgcaat   1500
gattgatgaa gatctgctgg aaaaagccaa taatctggtg attagcattt aa           1552
```

<210> SEQ ID NO 3
<211> LENGTH: 199
<212> TYPE: DNA
<213> ORGANISM: Artificial Sequence
<220> FEATURE:
<223> OTHER INFORMATION: pLuxR (Aliivibrio fischeri (Vibrio
      fischeri)) - E7 protein

<400> SEQUENCE: 3

```
acctgtagga tcgtacaggt ttacgcaaga aaatggtttg ttatagtcga ataaaatgaa    60
aaaaataaca gggattattt tattgcttct tgcagccatt attcttgctg catgtcaggc   120
aaactatatc cgtgatgttc agggcgggac agtatcaccg tcgtcaactg ctgaactgac   180
cggagtggaa acgcagtaa                                                199
```

<210> SEQ ID NO 4
<211> LENGTH: 2471
<212> TYPE: DNA
<213> ORGANISM: Artificial Sequence
<220> FEATURE:
<223> OTHER INFORMATION: LasR-pLuxR (Aliivibrio fischeri (Vibrio
      fischeri))-Pyocin S5-pLuxR (Aliivibrio fischeri (Vibrio
      fischeri)) - E7 protein

<400> SEQUENCE: 4

```
atggccttgg ttgacggttt tcttgagctg gaacgctcaa gtggaaaatt ggagtggagc    60
gccatcctcc agaagatggc gagcgacctt ggattctcga agatcctgtt cggcctgttg   120
cctaaggaca gccaggacta cgagaacgcc ttcatcgtcg gcaactaccc ggccgcctgg   180
cgcgagcatt acgaccgggc tggctacgcg cgggtcgacc cgacggtcag tcactgtacc   240
cagagcgtac tgccgatttt ctgggaaccg tccatctacc agacgcgaaa gcagcacgag   300
ttcttcgagg aagcctcggc cgccggcctg gtgtatgggc tgaccatgcc gctgcatggt   360
gctcgcggcg aactcggcgc gctgagcctc agcgtggaag cggaaaaccg ggccgaggcc   420
aaccgtttca tagagtcggt cctgccgacc ctgtggatgc tcaaggacta cgcactgcaa   480
agcggtgccg gactggcctt cgaacatccg gtcagcaaac cggtggttct gaccagccgg   540
```

```
gagaaggaag tgttgcagtg gtgcgccatc ggcaagacca gttgggagat atcggttatc      600
tgcaactgct cggaagccaa tgtgaacttc catatgggaa atattcggcg aagttcggt       660
gtgacctccc gccgcgtagc ggccattatg gccgttaatt tgggtcttat tactctctaa     720
acctgtagga tcgtacaggt ttacgcaaga aaatggtttg ttatagtcga ataaaatgag     780
caatgataat gaagttccgg gtagcatggt tattgttgca cagggtccgg atgatcagta     840
tgcatatgaa gttcctccga ttgatagcgc agcagttgcc ggtaatatgt ttggtgatct     900
gattcagcgc gaaatttatc tgcagaaaaa tatttattat ccggtgcgca gcattttga     960
acagggcacc aaagaaaaaa aagaaattaa taaaaaagtg agcgatcagg ttgatggtct    1020
gctgaaacaa attacccagg gtaaacgtga agcaacccgt caagaacgtg ttgatgttat    1080
gagcgcagtg ctgcataaaa tggaaagcga tctggaaggc tataaaaaaa cctttacgaa    1140
aggtccgttt attgattatg aaaaacagag cagcctgagc atttatgaag cctgggtgaa    1200
aatttgggaa aaaaatagct gggaagaacg taaaaaatat ccgtttcagc agctggttcg    1260
cgatgaactg gaacgtgcag tggcatatta taaacaggat agcctgagcg aagcagttaa    1320
agttctgcgt caggaactga ataaacagaa agccctgaaa gaaaagaag atctgagcca    1380
actgaacgc gattatcgta cccgtaaagc caatctggaa atgaaagttc agagcgaact    1440
ggatcaggca ggctctgcac tgcctccgct ggttagcccg acaccggaac agtggctgga   1500
acgcgcaacc cgtctggtta cccaggcaat tgcagataaa aaacagctgc agaccaccaa   1560
taatacccctg attaaaaatt ctccgacacc gctggaaaaa cagaaagcga tttataatgg   1620
tgaactgctg gttgatgaaa tcgcatcact gcaggcacgt ctggttaaac tgaatgcaga   1680
aaccacccgt cgtcgtaccg aagcagaacg taaagcagca gaagaacagg cactgcagga   1740
tgcaattaaa ttcaccgcag attttttataa agaagtgacc gaaaaatttg gtgcacgtac   1800
cagcgaaatg gcacgtcagc tggcagaagg tgcacgcggt aaaaatattc gtagcagcgc   1860
agaagcaatt aaatcttttg aaaaacataa agatgccctg aataaaaaac tgagcctgaa   1920
agatcgtcag gcaattgcca aagcatttga ttccctggat aaacaaatga tggcaaaaag   1980
cctggaaaaa tttagcaaag gttttggtgt tgtgggtaaa gcaattgatg cagcaagcct   2040
gtatcaggaa tttaaaatta gcaccgaaac aggcgattgg aaaccgtttt ttgtgaaaat   2100
tgaaaccctg gcagccggtg cagcagcaag ctggctggtt ggtattgcat ttgcaaccgc   2160
aaccgccacc ccgattggta ttctgggttt tgcactggtt atggcagtta ccggtgcaat   2220
gattgatgaa gatctgctgg aaaaagccaa taatctggtg attagcattt aaacctgtag   2280
gatcgtacag gtttacgcaa gaaaatggtt tgttatagtc gaataaaatg aaaaaaataa   2340
cagggattat tttattgctt cttgcagcca ttattcttgc tgcatgtcag gcaaactata   2400
tccgtgatgt tcagggcggg acagtatcac cgtcgtcaac tgctgaactg accggagtgg   2460
aaacgcagta a                                                        2471
```

<210> SEQ ID NO 5
<211> LENGTH: 803
<212> TYPE: DNA
<213> ORGANISM: Artificial Sequence
<220> FEATURE:
<223> OTHER INFORMATION: TetR promoter-transcriptional regulator LasR

<400> SEQUENCE: 5

```
tccctatcag tgatagagat tgacatccct atcagtgata gagatactga gcactactag     60
agaaagagga gaaatactag atggccttgg ttgacggttt tcttgagctg gaacgctcaa    120
```

```
gtggaaaatt ggagtggagc gccatcctcc agaagatggc gagcgacctt ggattctcga      180
agatcctgtt cggcctgttg cctaaggaca gccaggacta cgagaacgcc ttcatcgtcg      240
gcaactaccc ggccgcctgg cgcgagcatt acgaccgggc tggctacgcg cgggtcgacc      300
cgacggtcag tcactgtacc cagagcgtac tgccgatttt ctgggaaccg tccatctacc      360
agacgcgaaa gcagcacgag ttcttcgagg aagcctcggc cgccggcctg gtgtatgggc      420
tgaccatgcc gctgcatggt gctcgcggcg aactcggcgc gctgagcctc agcgtggaag      480
cggaaaaccg ggccgaggcc aaccgtttca tagagtcggt cctgccgacc ctgtggatgc      540
tcaaggacta cgcactgcaa agcggtgccg gactggcctt cgaacatccg gtcagcaaac      600
cggtggttct gaccagccgg gagaaggaag tgttgcagtg gtgcgccatc ggcaagacca      660
gttgggagat atcggttatc tgcaactgct cggaagccaa tgtgaacttc catatgggaa      720
atattcggcg gaagttcggt gtgacctccc gccgcgtagc ggccattatg gccgttaatt      780
tgggtcttat tactctctaa taa                                              803
```

<210> SEQ ID NO 6
<211> LENGTH: 2902
<212> TYPE: DNA
<213> ORGANISM: Artificial Sequence
<220> FEATURE:
<223> OTHER INFORMATION: ptetR-LasR-Terminator-pLuxR-pyocin -
    S5-Terminator-pLuxR-E7

<400> SEQUENCE: 6

```
tccctatcag tgatagagat tgacatccct atcagtgata gagatactga gcactactag       60
agaaagagga gaaatactag atggccttgg ttgacggttt tcttgagctg gaacgctcaa      120
gtggaaaatt ggagtggagc gccatcctcc agaagatggc gagcgacctt ggattctcga      180
agatcctgtt cggcctgttg cctaaggaca gccaggacta cgagaacgcc ttcatcgtcg      240
gcaactaccc ggccgcctgg cgcgagcatt acgaccgggc tggctacgcg cgggtcgacc      300
cgacggtcag tcactgtacc cagagcgtac tgccgatttt ctgggaaccg tccatctacc      360
agacgcgaaa gcagcacgag ttcttcgagg aagcctcggc cgccggcctg gtgtatgggc      420
tgaccatgcc gctgcatggt gctcgcggcg aactcggcgc gctgagcctc agcgtggaag      480
cggaaaaccg ggccgaggcc aaccgtttca tagagtcggt cctgccgacc ctgtggatgc      540
tcaaggacta cgcactgcaa agcggtgccg gactggcctt cgaacatccg gtcagcaaac      600
cggtggttct gaccagccgg gagaaggaag tgttgcagtg gtgcgccatc ggcaagacca      660
gttgggagat atcggttatc tgcaactgct cggaagccaa tgtgaacttc catatgggaa      720
atattcggcg gaagttcggt gtgacctccc gccgcgtagc ggccattatg gccgttaatt      780
tgggtcttat tactctctaa taatactaga gccaggcatc aaataaaacg aaaggctcag      840
tcgaaagact gggcctttcg ttttatctgt tgtttgtcgg tgaacgctct ctactagagt      900
cacactggct caccttcggg tgggcctttc tgcgtttata tactagagac ctgtaggatc      960
gtacaggttt acgcaagaaa atggtttgtt atagtcgaat aaatactaga gtcacacagg     1020
aaagtactag atgagcaa tgataatgaa gttccgggta gcatggttat tgttgcacag     1080
ggtccggatg atcagtatgc atatgaagtt cctccgattg atagcgcagc agttgccggt     1140
aatatgtttg tgatctgat tcagcgcgaa atttatctgc agaaaatat ttattatccg     1200 gtgcgcagca ttttgaaca gggcaccaaa gaaaaaaaag aaattaataa aaagtgagc     1260 gatcaggttg atggtctgct gaaacaaatt acccagggta acgtgaagc aacccgtcaa     1320
```

```
gaacgtgttg atgttatgag cgcagtgctg cataaaatgg aaagcgatct ggaaggctat    1380
aaaaaaacct ttacgaaagg tccgtttatt gattatgaaa acagagcag cctgagcatt    1440 tatgaagcct gggtgaaaat ttgggaaaaa aatagctggg aagaacgtaa aaaatatccg    1500
tttcagcagc tggttcgcga tgaactggaa cgtgcagtgg catattataa acaggatagc    1560
ctgagcgaag cagttaaagt tctgcgtcag gaactgaata acagaaagc cctgaaagaa    1620 aaagaagatc tgagccaact ggaacgcgat tatcgtaccc gtaaagccaa tctggaaatg    1680
aaagttcaga gcgaactgga tcaggcaggc tctgcactgc ctccgctggt tagcccgaca    1740
ccggaacagt ggctggaacg cgcaacccgt ctggttaccc aggcaattgc agataaaaaa    1800
cagctgcaga ccaccaataa taccctgatt aaaaattctc cgacaccgct ggaaaaacag    1860
aaagcgattt ataatggtga actgctggtt gatgaaatcg catcactgca ggcacgtctg    1920
gttaaactga atgcagaaac cacccgtcgt cgtaccgaag cagaacgtaa agcagcagaa    1980
gaacaggcac tgcaggatgc aattaaattc accgcagatt tttataaaga agtgaccgaa    2040
aaatttggtg cacgtaccag cgaaatggca cgtcagctgg cagaaggtgc acgcggtaaa    2100
aatattcgta gcagcgcaga agcaattaaa tcttttgaaa aacataaaga tgccctgaat    2160
aaaaaactga gcctgaaaga tcgtcaggca attgccaaag catttgattc cctggataaa    2220
caaatgatgg caaaaagcct ggaaaaattt agcaaaggtt ttggtgttgt gggtaaagca    2280
attgatgcag caagcctgta tcaggaattt aaaattagca ccgaaacagg cgattggaaa    2340 ccgtttttg tgaaaattga aaccctggca gccggtgcag cagcaagctg gctggttggt    2400
attgcatttg caaccgcaac cgccaccccg attggtattc tgggtttgc actggttatg    2460 gcagttaccg gtgcaatgat tgatgaagat ctgctggaaa aagccaataa tctggtgatt    2520
agcatttaat actagagcca ggcatcaaat aaaacgaaag gctcagtcga agactgggc    2580 ctttcgtttt atctgttgtt tgtcggtgaa cgctctctac tagagtcaca ctggctcacc    2640
ttcgggtggg cctttctgcg tttatatact agagacctgt aggatcgtac aggtttacgc    2700
aagaaaatgg tttgttatag tcgaataaat actagagtca cacaggaaag tactagagat    2760
gaaaaaaata cagggattat ttttattgct tcttgcagcc attattcttg ctgcatgtca    2820
ggcaaactat atccgtgatg ttcagggcgg gacagtatca ccgtcgtcaa ctgctgaact    2880
gaccggagtg gaaacgcagt aa                                              2902
```

<210> SEQ ID NO 7
<211> LENGTH: 462
<212> TYPE: DNA
<213> ORGANISM: Artificial Sequence
<220> FEATURE:
<223> OTHER INFORMATION: constructed from microcin S sequence derived
      from AFH37358.1 with a promoter sequence.

<400> SEQUENCE: 7

```
ggttcaccga atctatctc atttgctagt tataaaatta tgaaatttgc ataaattctt      60
cagcttccta ttttactaga gaaagaggag aaaggatcta tgtcaaatat cagagaattg    120
agttttgatg aaattgcatt agtcagtggt ggcaacgcaa acagtaatta tgaaggaggc    180
ggaagtcgta gtcgtaacac cggagcccgt aactcactgg gacgaaatgc accgacacac    240
atttacagtg acccgagcac agttaaatgt gctaatgctg tctttagtgg aatggttggt    300
ggtgccatta aaggtggtcc tgtaggaatg accagaggaa ctattggtgg gcagttatc     360 ggccagtgtc tctccggtgg aggaaatggt aacggaggcg gaaacagagc tggttccagt    420
```

```
aattgttcag gaagtaacgt cggtggtacc tgtagtcgat aa                          462
```

<210> SEQ ID NO 8
<211> LENGTH: 948
<212> TYPE: DNA
<213> ORGANISM: Artificial Sequence
<220> FEATURE:
<223> OTHER INFORMATION: DnaseI sequence derived from NM_174534.2 and
      was codon optimized for E. coli expression with a promoter
      sequence

<400> SEQUENCE: 8

```
ggttcaccga atctatctc atttgctagt tataaaatta tgaaatttgc ataaattctt        60
cagcttccta ttttactaga gaaagaggag aaaggatcta tgcgtggcac ccgtctgatg      120
ggtctgctgc tggcactggc tggcctgctg cagctgggtc tgagcctgaa aattgcagca      180
tttaacattc gtaccttcgg cgaaaccaaa atgagcaatg caaccctggc aagctatatt      240
gttcgtattg tgcgtcgtta tgatatcgtg ctgattcaag aagttcgcga tagccatctg      300
gttgcagttg gtaaactgct ggattatctg aatcaggatg atccgaacac ctatcattat      360
gttgttagcg aaccgctggg tcgcaatagc tataaagaac gttacctgtt tctgtttcgt      420
ccgaataaag ttagcgttct ggatacctat cagtatgatg atggttgtga agctgtggc       480
aatgatagct ttagccgtga accggcagtt gtgaattttt caagccatag caccaaagtg      540
aaagaatttg caattgttgc actgcatagc gcaccgagtg atgcagttgc agaaattaac      600
agcctgtatg atgtttatct ggacgttcag cagaaatggc atctgaatga tgttatgctg      660
atgggcgatt caatgccga ttgtagctat gttaccagca gccagtggtc aagcattcgt       720
ctgcgtacca gcagtacctt tcagtggctg attccggata cgcagatac caccgcaacc      780
agcaccaatt gtgcatatga tcgtattgtt gttgcaggta gtctgctgca gagcagcgtt      840
gttccgggta gtgcagcacc gtttgatttc caggcagcat atggtctgag caatgaaatg      900
gccctggcaa ttagcgatca ttatccggtt gaagttaccc tgacctaa                   948
```

<210> SEQ ID NO 9
<211> LENGTH: 743
<212> TYPE: DNA
<213> ORGANISM: Artificial Sequence
<220> FEATURE:
<223> OTHER INFORMATION: modified from U00096.3, AAC74951.1 with a
      promoter sequence

<400> SEQUENCE: 9

```
ggttcaccga atctatctc atttgctagt tataaaatta tgaaatttgc ataaattctt        60
cagcttccta tttggatctt cacacaggac tactagagat gatgcaacca tcaatcaaac      120
ctgctgacga gcattcagct ggcgatatca ttgcgcgcat cggcagcctg acgcgtatgc      180
tgcgcgacag tttgcgggaa ctggggctgg atcaggccat tgccgaagcg gcggaagcca      240
tccccgatgc gcgcgatcgt ttgtactatg ttgtgcagat gaccgcccag gctgcggagc      300
gggcgctgaa cagtgttgag gcgtcacaac cgcatcagga tcaaatggag aaatcagcaa      360
aagcgttaac ccaacgttgg gatgactggt tgccgatcc gattgacctt gccgacgccc       420
gtgaactggt aacagataca cgacaatttc tggcagatgt acccgcgcat accagcttta      480
ctaacgcgca actgctggaa atcatgatgg cgcaggattt tcaggatctc accgggcagg      540
tcattaagcg gatgatggat gtcattcagg agatcgaacg ccagttgctg atggtgctgt      600
tggaaaacat ccccggaaca gagtcgcgtc caaaacgtga aaaccagagt ttgcttaatg      660
```

```
gacctcaggt cgataccagc aaagccggtg tggtagccag tcaggatcag gtggacgatt    720
tgttggatag tcttggattt tga                                           743

<210> SEQ ID NO 10
<211> LENGTH: 357
<212> TYPE: DNA
<213> ORGANISM: Artificial Sequence
<220> FEATURE:
<223> OTHER INFORMATION: modified from NC_000913.3

<400> SEQUENCE: 10
atgaaaaaaa gaggggcgtt tttagggctg ttgttggttt ctgcctgcgc atcagttttc     60
gctgccaata atgaaaccag caagtcggtc actttcccaa agtgtgaaga tctggatgct    120
gccggaattg ccgcgagcgt aaaacgtgat tatcaacaaa atcgcgtggc gcgttgggca    180
gatgatcaaa aaattgtcgg tcaggccgat cccgtggctt gggtcagttt gcaggacatt    240
cagggtaaag atgataaatg gtcagtaccg ctaaccgtgc gtggtaaaag tgccgatatt    300
cattaccagg tcagcgtgga ctgcaaagcg ggaatggcgg aatatcagcg gcgttaa      357
```